US006673917B1

(12) United States Patent
Korneluk et al.

(10) Patent No.: US 6,673,917 B1
(45) Date of Patent: Jan. 6, 2004

(54) ANTISENSE IAP NUCLEIC ACIDS AND USES THEREOF

(75) Inventors: Robert G. Korneluk, Ottawa (CA); Eric LaCasse, Ottawa (CA); Stephen Baird, Ottawa (CA); Martin Holcik, Ottawa (CA); Sean Young, Ottawa (CA)

(73) Assignee: University of Ottawa, Ottawa (CA)

( * ) Notice: Subject to any disclaimer, the term of this patent is extended or adjusted under 35 U.S.C. 154(b) by 126 days.

(21) Appl. No.: 09/672,717

(22) Filed: Sep. 28, 2000

(51) Int. Cl.$^7$ .......................... C07H 21/04; C12P 19/34
(52) U.S. Cl. .................... 536/24.5; 536/23.1; 536/24.3; 536/24.31; 536/24.33; 435/91.31
(58) Field of Search ............................... 536/24.5, 23.1, 536/24.3, 24.33, 24.31; 435/325, 375, 455, 458, 91.31

(56) References Cited

U.S. PATENT DOCUMENTS

| | | | |
|---|---|---|---|
| 5,510,239 A | * | 4/1996 | Baracchini et al. |
| 5,665,550 A | | 9/1997 | Roninson et al. |
| 5,919,912 A | | 7/1999 | Korneluk et al. |
| 5,958,771 A | | 9/1999 | Bennett et al. |
| 5,958,772 A | | 9/1999 | Bennett et al. |
| 6,087,173 A | | 7/2000 | Bennett et al. |
| 6,107,041 A | | 8/2000 | Korneluk et al. |
| 6,133,437 A | * | 10/2000 | Korneluk et al. |
| 6,187,557 B1 | | 2/2001 | Rothe et al. |

FOREIGN PATENT DOCUMENTS

| | | |
|---|---|---|
| WO | WO 94/06814 | 3/1994 |
| WO | WO 95/19431 | 7/1995 |
| WO | WO 96/12016 | 4/1996 |
| WO | WO 97/06182 | 2/1997 |
| WO | WO 97/06255 | 2/1997 |
| WO | WO 97/26331 | 7/1997 |
| WO | WO 98/22131 | 5/1998 |
| WO | WO 98/35693 | 8/1998 |
| WO | WO 00/32816 | 6/2000 |
| WO | WO 00/32818 | 6/2000 |

OTHER PUBLICATIONS

Andrea D. Branch, A good antisense molecule is hard to find, TIBS, 47–48, 1998.*

C. A. Stein Is irrelevant cleavage the price of antisense efficacy? Pharmacology & Therapeutics vol. 85, pp. 231–236, 2000.*

Andreeff et al., "Inhibitor–of–apoptosis (IAP) Proteins XIAP and Survivin in Primary Acute Myelogenous Leukemias (AML): Regulation and Therapeutic Targets," Proceedings Annual Meeting of the American Association for Cancer Research, Abstract 41:739–740 (2000).

Branch, "A Good Antisense Molecule Is Hard To Find," TIBS p. 45–50 (1998).

Birnbaum et al., "An Apoptosis–inhibiting Gene From a Nuclear Polyhedrosis Virus Encoding a Polypeptide with Cys/His Sequence Motifs," J. Virol., 68:2521–2528, (1994).

Cheng et al., "Staurosporine, K–252a, And K–252b Stabilize Calcium Homeostasis and Promote Survival of CNS Neurons in the Absence of Glucose," J. Neurochem., 62:1319–1329, (1994).

Clem et al., "Anti–apoptotic genes of baculoviruses," Cell Death and Differentiation, 3:9–16, (1996).

Clem et al., "Induction and Inhibition of Apoptosis By Insect Viruses," Apoptosis II: The Molecular Basis of Apoptosis in Disease, Cold Spring Harbor Laboratory Press, p. 89–110, (1994).

Clem et al., "Prevention of Apoptosis by a Baculovirus Gene During Infection of Insect Cells," Science 254:1388–1390, (1991).

Clem et al., "Control of Programmed Cell Death by the Baculovirus Genes p35 And iap," Mol. and Cell. Biology, 14:5212–5222 (1994).

Crook et al., "An apoptosis–inhibiting baculovirus gene with a zinc finger–like motif," J. Virol., 67:2168–2174, (1993).

Dhein et al., "Autocrine T–cell Suicide Mediated by APO–1/(Fas/CD95)," Nature, 373:438–441, (1995).

Duckett et al., "A Conserved Family of Cellular Genes Related to the Baculovirus IAP Gene and Encoding Apoptosis Inhibitors," EMBO J., 15:2685–2694, (1996).

Erl et al., "Nuclear Factor–kappa B Regulates Induction of Apoptosis and Inhibitor of Apoptosis Protein–1 Expression in Vascular Smooth Muscle Cells," Cir. Res. 84:668–677 (1999).

Fernandez et al., "Differential Sensitivity of Normal and Ha–ras–transformed C3H Mouse Embryo Fibroblasts to Tumor Necrosis Factor: Induction of bcl–2, c–myc, and Manganese Superoxide Dismutase in Resistant Cells," Oncogene 9:2009–2017, (1994).

Ferrari et al., "N–acetylcysteine (D– and L–stereoisomers) Prevents Apoptotic Death of Neuronal Cells," J. Neurosci., 15:2857–2866, (1995).

Fisher et al., "Dominant Interfering Fas Gene Mutations Impair Apoptosis in a Human Autoimmune Lymphoproliferative Syndrome," Cell, 81:935–946, (1995).

Francis et al., "The Response Of GABAergic and Cholinergic Neurons to Transient Cerebral Ischemia," Brain Res., 243:271–278, (1982).

(List continued on next page.)

Primary Examiner—Sean McGarry
Assistant Examiner—Janet Epps-Ford
(74) Attorney, Agent, or Firm—Kristina Bieker-Brady; Clark & Elbing LLP

(57) ABSTRACT

The present invention feature antisense IAP nucleic acids and other negative regulators of the IAP anti-apoptotic pathway, and methods for using them to enhance apoptosis.

22 Claims, 67 Drawing Sheets

OTHER PUBLICATIONS

Gibellini et al., "Tat–expressing Jurkat Cells Show an Increased Resistance to Different Apoptotic Stimuli, Including Acute Human Immunodeficiency Virus–type 1 (HIV–1) Infection," Br. J. Haematol., 89:24–33, (1995).

Glicksman et al., "K–252a and Staurosporine Promote Choline Acetyltransferase Activity in Rat Spinal Cord Cultures," J. Neurochem., 61:210–221, (1993).

Glicksman et al., "A K–252a Analog Prevents Developmentally Programmed Motoneuron Death and the Loss of Chat Activity in Adult Motoneurons In Vivo," Soc. Neuro. Abst., 441, (1994).

Glicksman et al., "K–252a Promotes Survival and Choline Acetyltransferase Activity in Striatal and Basal Forebrain Neuronal Cultures," J. Neurochem., 64:1502–1512, (1995).

Golstein et al., "Homology Between Reaper and the Cell Death Domains of Fas and TNFR1," Cell 81:185–186, (1995).

Goruppi et al., "Dissection of c–myc Domains Involved in S Phase Induction of NIH3T3 Fibroblasts," Oncogene, 9:1537–1544 (1994).

Harrington et al., "c–Myc–induced Apoptosis in Fibroblasts is Inhibited by Specific Cytokines," EMBO J. 13:3286–3295, (1994).

Itoh et al., "A Novel Protein Required for Apoptosis. Mutational analysis of human Fas antigen," J. Biol. Chem., 268:10932–10937, (1993).

Katsikis et al., "Fas Antigen Stimulation Induces Marked Apoptosis of T Lymphocytes In Human Immunodeficiency Virus–infected Individuals," J. Exp. Med., 181:2029–2036, (1995).

Kerr, "Neglected Opportunities in Apoptosis Research," Trends in Cell Biology, 5:55–57 (1995).

Korneluk et al., USSN 09/617,053, filed Jul. 14, 2000.

Korsmeyer, "Regulators of Cell Death," TIG 11:101–105, (1995).

Li et al., "Induction of Apoptosis in Uninfected Lymphocytes by HIV–1 Tat Protein," Science, 268:429–431, (1995).

Li et al., "Pleiotropic Cell–division Defects and Apoptosis Induced by Interference with Survivin Function," Nat. Cell Biol. 1:461–466 (1999).

Liston et al., "Suppression of Apoptosis in Mammalian Cells by NAIP and a Related Family of IAP Genes," Nature, 379:349–353, (1996).

Martin et al., "HIV–1 Infection of Human CD4+ T Cells In Vitro. Differential Induction Of Apoptosis In These Cells," J. Immunol., 152:330–342, (1994).

Melino et al., "Tissue Transglutaminase and Apoptosis: Sense and Antisense Transfection Studies with Human Neuroblastoma Cells," Mol. Cell. Biol., 14:6584–6596, (1994).

Murayama et al., "Immunocytochemical and Ultrastructural Studies of Werdnig–Hoffmann Disease," Acta Neuropathol., 81:408–417, (1991).

Muro–Cacho et al., "Analysis Of Apoptosis in Lymph Nodes Of HIV–infected Persons. Intensity of Apoptosis Correlates with the General State of Activation of the Lymphoid Tissue and not with Stage of Disease or Viral Burden," J. Immunol., 154:5555–5566, (1995).

Nakanishi et al., "K–252a, a Novel Microbial Product, Inhibits Smooth Muscle Myosin Light Chain Kinase," J. Biol. Chem., 263:6215–6219, (1988).

Norris et al., "Design and Testing of Ribozymes for Cancer Gene therapy," Cancer Gene Therapy: Past Achievements and Future Challenges, Kluwer Academic/Plenum Publishers, New York, pp. 293–301 (2000).

Nũnez et al., "The Bcl–2 Family of Proteins: Regulators of Cell Death and Survival," Trends in Cell Biology, 4:399–403, (1994).

Osborne et al., "Essential Genes that Regulate Apoptosis," Trends in Cell Biology, 4:394–398, (1994).

Peterson et al., "Loss Of GABAergic neurons in Medial Septum After Fimbria–fornix Transection," Neurosci. Lett., 76:140–144, (1987).

Pulsinelli et al., "Temporal Profile of Neuronal Damage in a Model of Transient Forebrain Ischemia," Ann. Neurol., 11:491–498, (1982).

Rabizadeh et al., "Expression of the Baculovirus p35 Gene Inhibits Mammalian Neural Cell Death," J. Neurochem., 61:2318–2321, (1993).

Ridoux et al., "The Use of Adenovirus Vectors for Intracerebral Grafting of Transfected Nervous Cells," NeuroReport., 5:801–804, (1994).

Ridoux et al., "Adenoviral Vectors as Functional Retrograde Neuronal Tracers," Brain Res., 648:171–175, (1994).

Ridoux et al., "Ex Vivo Culture of Adult Microglial Cells from Previously Lesioned Rat Brains," C.R. Acad. Sci. Paris/Sciences Neurobiology, 317:217–224, (1994).

Rieux–Laucat et al., "Mutations in Fas Associated with Human Lymphoproliferative Syndrome and Autoimmunity," Science, 268:1347–1349, (1995).

Rosenbaum et al., "Evidence For Hypoxia–induced, Programmed Cell Death Of Cultured Neurons," Ann. Neurol., 36:864–870, (1994).

Rothe et al., "The TNFR2–TRAF Signaling Complex Contains Two Novel Proteins Related to Baculoviral Inhibitor of Apoptosis Proteins," Cell, 83:1243–1252, (1995).

Roy et al., "The Gene for Neuronal Apoptosis Inhibitory Protein is Partially Deleted in Individuals with Spinal Muscular Atrophy," Cell, 80:167–178, (1995).

Sato et al., "Neuronal Differentiation Of PC12 Cells as a Result of Prevention of Cell Death by bcl–2," J. Neurobiol., 25:1227–1234, (1994).

Sauer et al., "Progressive Degeneration of Nigrostriatal Dopamine Neurons Following Intrastriatal Terminal Lesions with 6–hydroxydopamine: A Combined Retrograde Tracing An Immunocytochemical Study in the Rat," Neuroscience, 59:401–405, (1994).

Smith–Swintosky et al., "K252A, K252B and Staurosporine Increase Hippocampal Neuron Survival and Improve Water Maze Performance After Kainate Lesion," Soc. Neuro. Abst., 2130, (1995).

Steiman et al., "Infantile Neuronal Degeneration Masquerading as Werdnig–Hoffmann Disease," Ann. Neurol., 8:317–324, (1980).

Steller, "Mechanisms and Genes of Cellular Suicide," Science, 267:1445–1455, (1995).

Talley et al., "Tumor Necrosis Factor Alpha–induced Apoptosis in Human Neuronal Cells: Protection by the Antioxidant N–acetylcysteine and the Genes bcl–2 and crmA," Mol. Cell. Biol., 15:2359–2366, (1995).

Terai et al., "Apoptosis as a Mechanism of Cell Death in Cultured T lymphoblasts Acutely Infected with HIV–1," J. Clin. Invest., 87:1710–1715, (1991).

Tetzlaff et al., "Changes in Cytoskeletal Proteins in the Rat Facial Nucleus Following Axotomy," J. Neurosci. 8:3181–3189, (1988).

Towfighi et al., "Is Werdnig–Hoffman Disease a Pure Lower Motor Neuron Disorder?," Acta Neuropathol. (Berl), 65:270–280, (1985).

Turner et al., "Ribozymes: Their Design and Use in Cancer," Cancer Gene Therapy: Past Achievements and Future Challenges, Kluwer Academic/Plenum Publishers, New York, pp. 303–318 (2000).

Vossbeck et al., "Direct Transforming Activity of TGG–beta on Rat Fibroblasts," Int. J. Cancer, 61:92–97 (1995).

Walkinshaw et al., "Induction of Apoptosis in Catecholaminergic PC12 Cells by L–DOPA. Implications for the Treatment of Parkinson's Disease," J. Clin. Invest. 95:2458–2464, (1995).

Westendorp et al., "Sensitization of T Cells to CD95–mediated Apoptosis by HIV–1 Tat And gp120," Nature, 375:497–499, (1995).

White et al., "Genetic Control of Programmed Cell Death in Drosophila," Science, 264:677–683, (1994).

Williams et al., "Apoptosis: Final Control Point in Cell Biology," Trends in Cell Biology 2:263–267, (1992).

Wyllie, "Death Gets A Brake," Nature, 369:272–273, (1994).

Xu et al., "Elevation Of Neuronal Expression Of NAIP Reduces Ischemic Damage In The Rat Hippocampus," Nature Medicine 3:997–1004, (1997).

Xu et al., "Distribution Of Neuronal Apoptosis Inhibitory Protein–Like Immunoreactivity in the Rat Central Nervous System," The Journal of Comparative Neurology 382:247–259, (1997).

Holcik. et al., "Translational Upregulation of X–Linked Inhibitor of Apoptosis (XIAP) increases Resistance to Radiation Induced Cell Death," *Oncogene* 19:4174–4177 (2000).

Lacasse, et al., "The Inhibitors of Apoptosis (IAPs) and Their Emerging Role In Cancer," *Oncogene* 17:3247–3259 (1998).

Olie, et al., "A Novel Antisense Oligonucleotide Targeting Survivin Expression Induces Apoptosis and Sensitizes Lung Cancer Cells to Chemotherapy," *Cancer Research* 60:2805–2809 (2000).

Sesaki, et al., "Down–regulation of X–Linked Inhibitor of Apoptosis Protein Induces Apoptosis in Chemoresistant Human Ovarian Cancer Cells," *Cancer Research* 60:5659–5666 (2000).

Stein, "How to Design an Antisense Oligodeoxynucleotide Experiment: A Consensus Approach," *Antisense & Nucleic Acid Drug Development* 8:129–132 (1998).

* cited by examiner

HUMAN xiap

```
1   gaaaaggtggacaagtcctaattcaagagaagaagatgacttttaacagtttgaaggatct    60
                                          M  T  F  N  S  F  E  G  S 61  aaaacttgtacctgcagacatcaataaggaagaagaatttgtagaagagtttaataga     120
    K  T  C  V  P  A  D  I  N  K  E  E  E  F  V  E  E  F  N  R 121 ttaaaaactttgctaatttccaagtggtagtcctgtttcagcatcaacactggcacga     180
    L  K  T  F  A  N  F  P  S  G  S  P  V  S  A  S  T  L  A  R 181 gcaggtttctcttatactggtgaaggagataccgtgcggtgcttagttgtcatgcagct     240
    A  G  F  L  Y  T  G  E  G  D  T  V  R  C  F  S  C  H  A  A 241 gtagatagatggcaatatggagactcagcagttggaagacacaggaaagtatccccaaat   300
    V  D  R  W  Q  Y  G  D  S  A  V  G  R  H  R  K  V  S  P  N 301 tgcagatttatcaacggcttttatcttgaaaatagtgccacgcagtctacaaattctggt   360
    C  R  F  I  N  G  F  Y  L  E  N  S  A  T  Q  S  T  N  S  G
```

FIG. 1 (PAGE 1 OF 7)

HUMAN xiap

```
361  atccagaatggtcagtacaaagttgaaaactatctgggaagcagagatcatttgcctta
     ---------+---------+---------+---------+---------+---------+  420
      I  Q  N  G  Q  Y  K  V  E  N  Y  L  G  S  R  D  H  F  A  L 421  gacaggccatctgagacacatgcagactatcttgagaactgggcaggttgtagatata
     ---------+---------+---------+---------+---------+---------+  480
      D  R  P  S  E  T  H  A  D  Y  L  L  R  T  G  Q  V  V  D  I 481  tcagacaccatatacccgagaaccctgccatgtattgtgaagaagctagattaaagtcc
     ---------+---------+---------+---------+---------+---------+  540
      S  D  T  I  Y  P  R  N  P  A  M  Y  C  E  E  A  R  L  K  S 541  tttcagaactggccagactatgctcacctaacccaagagagtagcaagtgctggactc
     ---------+---------+---------+---------+---------+---------+  600
      F  Q  N  W  P  D  Y  A  H  L  T  P  R  E  L  A  S  A  G  L 601  tactacacaggtattggtgaccaagtgcagtgcttttgtgttggtggaaaactgaaaaat
     ---------+---------+---------+---------+---------+---------+  660
      Y  Y  T  G  I  G  D  Q  V  Q  C  F  C  C  G  G  K  L  K  N 661  tgggaacctgtgatcgtgctgtcagaacacaggcgacacttcctaattgcttcttt
     ---------+---------+---------+---------+---------+---------+  720
      W  E  P  C  D  R  A  W  S  E  H  R  R  H  F  P  N  C  F  F
```

FIG. 1 (PAGE 2 OF 7)

HUMAN xiap

```
      gtttgggccggaatcttaatattcgaagtgaatctgatgctgtgagttctgataggaat
721   ------------------------------------------------------------  780
       V  L  G  R  N  L  N  I  R  S  E  S  D  A  V  S  S  D  R  N ttcccaaattcaacaaatcttccaagaaatccatgcagattatgaagcacggatc
781   ------------------------------------------------------------  840
       F  P  N  S  T  N  L  P  R  N  P  S  M  A  D  Y  E  A  R  I tttactttgggacatggatatactcagtgttaacaaggagcagcttgcaagagctggattt
841   ------------------------------------------------------------  900
       F  T  F  G  T  W  I  Y  S  V  N  K  E  Q  L  A  R  A  G  F tatgcttaggtgaaggtgataaagtaaagtgcttcactgtggaggagggctaactgat
901   ------------------------------------------------------------  960
       Y  A  L  G  E  G  D  K  V  K  C  F  H  C  G  G  G  L  T  D tggaagcccagtgaagacccttgggaacaacatgctaaatgtatccagggtgcaaatat
961   ------------------------------------------------------------  1020
       W  K  P  S  E  D  P  W  E  Q  H  A  K  W  Y  P  G  C  K  Y ctgttagaacagaagggacaagaatatataaacaatattcattaactcattcacttgag
1021  ------------------------------------------------------------  1080
       L  L  E  Q  K  G  Q  E  Y  I  N  N  I  H  L  T  H  S  L  E
```

FIG. 1 (PAGE 3 OF 7)

HUMAN xiap

```
1081  gagtgtctggtaagaactactgagaaacaccatcaactactagaagaattgatgatacc  1140
      ---------+---------+---------+---------+---------+---------+
      E  C  L  V  R  T  T  E  K  T  P  S  L  T  R  R  I  D  D  T 1141  atcttccaaatcctatggtacaagaagctatacgaatggggttcagtttcaaggacatt  1200
      ---------+---------+---------+---------+---------+---------+
      I  F  Q  N  P  M  V  Q  E  A  I  R  M  G  F  S  F  K  D  I 1201  aagaaaataatggaggaaaaaattcagatatctgggagcaactataaatcactgaggtt  1260
      ---------+---------+---------+---------+---------+---------+
      K  K  I  M  E  E  K  I  Q  I  S  G  S  N  Y  K  S  L  E  V 1261  ctggttgcagatctagtgaatgctcagaaagacagtatgcaagatgagtcaagtcagact  1320
      ---------+---------+---------+---------+---------+---------+
      L  V  A  D  L  V  N  A  Q  K  D  S  M  Q  D  E  S  S  Q  T 1321  tcattacagaaagagattagtactgaagagcagctaaggcctgcaagaggagaagctt  1380
      ---------+---------+---------+---------+---------+---------+
      S  L  Q  K  E  I  S  T  E  E  Q  L  R  R  L  Q  E  E  K  L 1381  tgcaaatctgtatggatagaaatattgctatcgttttgtccttgtggacatctagtc  1440
      ---------+---------+---------+---------+---------+---------+
```

FIG. 1 (PAGE 4 OF 7)

HUMAN xiap

```
         C  K  I  C  M  D  R  N  I  A  I  V  F  V  P  C  G  H  L  V
      acttgtaaacaatgtgctgaagcagttgacaagtgtccccatgtgtgctacacagtcattact
1441  ------+---------+---------+---------+---------+---------+------ 1500
      tgaacattgttacacgacttcgtcaactgttcacaggtacacacgatgtgtcagtaatga  a T  C  K  Q  C  A  E  A  V  D  K  C  P  M  C  Y  T  V  I  T
      ttcaagcaaaaatttttatgtcttaatctctatagtaggcatgttatgttgttct
1501  ------+---------+---------+---------+---------+---------+------ 1560
      aagttcgtttttaaaaatacagaattagagatatcatccgtacaataacaagaaga  a F  K  Q  K  I  F  M  S  *
      tattaccctgattgatgtgtgaactgactttaagtaatcaggattgaattccat
1561  ------+---------+---------+---------+---------+---------+------ 1620
      ataatgggactaactacacacttgactgaaattcattagtcctaacttaaggta  a tagcattgctaccaagtaggaaaaaaatgtacatggcagtgttttagttggcaatata
1621  ------+---------+---------+---------+---------+---------+------ 1680
      atcgtaacgatggttcatcctttttttacatgtaccgtcacaaaatcaaccgttatat  a atctttgaattcttgattttcagggtattagctgtattatccattttttttactgtta
1681  ------+---------+---------+---------+---------+---------+------ 1740
      tagaaacttaagaactaaaagtcccataatcgacataataggtaaaaaaaatgacaat  a tttaattgaaaccatagactaagaataagaagcatcatactataactgaacacaatgtgt
1741  ------+---------+---------+---------+---------+---------+------ 1800
      aaattaacttttggtatctgattcttattcttcgtagtatgatattgacttgtgttacaca  a
```

FIG. 1 (PAGE 5 OF 7)

HUMAN xiap

```
     attcatagtatactgatttaattctaagtgtaagtgaattaatcatctgatttttat
1801 ---------+---------+---------+---------+---------+---------+ 1860
     a tcttttcagataggcttaacaaatggagctttctgtatataaatgtggagattagagtta
1861 ---------+---------+---------+---------+---------+---------+ 1920
     a atctccccaatcacataatttgttttgtgtgaaaaggaataaattgttccatgctggtg
1921 ---------+---------+---------+---------+---------+---------+ 1980
     a gaaagatagagattgttttagaggttggttgttgtgttttaggattctgtccattttct
1981 ---------+---------+---------+---------+---------+---------+ 2040
     a tgtaaagnnataaacacgnacntgtgcgaaatatnttgtaaagtgattgccattnttg
2041 ---------+---------+---------+---------+---------+---------+ 2100
     a aaagcgtattaatgatagaatactatcgagccaacatgtactgacatggaaagatgtca
2101 ---------+---------+---------+---------+---------+---------+ 2160
     a
```

FIG. 1 (PAGE 6 OF 7)

HUMAN xiap

```
2161  nagatatgttaagtgtaaaatgcaagtggcnnacactatgtatagtctgagccagatca
      ------------------------------+------------------------------+  2220
                                                                      a 2221  aagtatgtatgttnttaatatgcatagaacnanagatttggaaagatatacaccaaactg
      ------------------------------+------------------------------+  2280
                                                                      a 2281  ttaaatgtggtttctctcttcggggaggggggattggggagggcccagagggggttta
      ------------------------------+------------------------------+  2340
                                                                      a 2341  naggggcctttcacttttcnactttttcattttgttctgttcgnattttttataagtat
      ------------------------------+------------------------------+  2400
                                                                      a 2401  gtanacccnaagggtttatgnaactaacatcagtaaccccgtgactatcct
      ------------------------------+------------------------------+  2460
                                                                      a 2461  gtnctcttcctaggagctgtnttgttcccaccaccccttccctctgaacaaatgc
      ------------------------------+------------------------------+  2520
                                                                      a 2521  ctgagtgctggggcacttn
      ------------+  2540
                     a
```

FIG. 1 (PAGE 7 OF 7)

HUMAN hiap-1

```
    TCCTTGAGATGTATCAGTATATAGGATTTAGGATCTCCATGTTGGAACTCTAAATGCATAGA
  1 ------+---------+---------+---------+---------+---------+    60
        C

AATGGAAATAATGGAAATTTTCATTTTGGCTTTTCAGCCTAGTATTAAAACTGATAAAA
 61 ------+---------+---------+---------+---------+---------+   120
        C

GCAAAGCCATGCACAAAACTACCTCCCTAGAGAAAGGCTAGTCCCTTTCTTCCCCATTC
121 ------+---------+---------+---------+---------+---------+   180
        C

ATTTCATTATGAACATAGTAGAAAACAGCATATTCTTATCAAATTTGATGAAAAGCGCCA
181 ------+---------+---------+---------+---------+---------+   240
        C   M  N  I  V  E  N  S  I  F  L  S  N  L  M  K  S  A  N  -

ACACGTTTGAACTGAAATACGACTTGTCATGTGAACTGTACCGAATGTCTACGTATTCCA
241 ------+---------+---------+---------+---------+---------+   300
        C  T  F  E  L  K  Y  D  L  S  C  E  L  Y  R  M  S  T  Y  S  T  -

CTTTTCCTGCTGGGGTTCCTGTCTTCAGAAAGGAGTCTTGCTGTCGTGTTCTATTACA
301 ------+---------+---------+---------+---------+---------+   360
        C  F  P  A  G  V  P  V  S  E  R  S  L  A  R  A  G  F  Y  Y  T  -
```

FIG. 2 (PAGE 1 OF 8)

HUMAN hiap-1

```
       CTGGTGTGAATGACAAGGTCAAATGCTTCTGTTGTGGCCTGATGCTGGATAACTGGAAAA
361    ------------+---------+---------+---------+---------+---------+  420
         G  V  N  D  K  V  K  C  F  C  C  G  L  M  L  D  N  W  K  R  -

GAGGAGACAGTCCTACTGAAAAGCATAAAAGTTGTATCCTAGCTGCAGATTCGTTCAGA
421    ------------+---------+---------+---------+---------+---------+  480
         G  D  S  P  T  E  K  H  K  K  L  Y  P  S  C  R  F  V  Q  S  -

GTCTAAATTCCGTTAACAACTTGGAAGCTACCTCTCAGCCTACTTTTCCTTCTTCAGTAA
481    ------------+---------+---------+---------+---------+---------+  540
         L  N  S  V  N  N  L  E  A  T  S  Q  P  T  F  P  S  S  V  T  -

CACATTCCACACACTCATTACTTCCGGGTACAGAAAACACAGTGGATATTCCGTGGCTCTT
541    ------------+---------+---------+---------+---------+---------+  600
         H  S  T  H  S  L  L  P  G  T  E  N  S  G  Y  F  R  G  S  Y  -

ATTCAAACTCTCCATCAAATCCTGTAAACTCCAGAGCAAATCAAGAATTTTCTGCCTTGA
601    ------------+---------+---------+---------+---------+---------+  660
         S  N  S  P  S  N  P  V  N  S  R  A  N  Q  E  F  S  A  L  M  -

TGAGAAGTTCCTACCCCTGTCCAATGAATAACGAAAATGCCAGATTACTTTTCAGA
661    ------------+---------+---------+---------+---------+---------+  720
         R  S  S  Y  P  C  P  M  N  N  E  N  A  R  L  L  T  F  Q  T  -
```

FIG. 2 (PAGE 2 OF 8)

HUMAN hiap-1

```
721  CATGGCCATTGACTTTTCTGTCGCCAACAGATCTGGCACGAGCAGGCTTTTACTACATAG  780
       H  G  H  *  L  F  C  R  Q  Q  S  G  T  S  R  L  L  L  H  R
     c   W  P  L  T  F  L  S  P  T  D  L  A  R  A  G  F  Y  Y  I  G  -

781  GACCTGGAGACAGAGTGGCTTGCTTTGCCTGTGGTGAAATTGAGCAATTGGGAACCGA    840
     c   P  G  D  R  V  A  C  F  A  C  G  G  K  L  S  N  W  E  P  K  -

841  AGGATAAATGCTATGTCAGAACACCTGAGACATTTTCCCAAATGCCCATTTATAGAAAATC  900
     c   D  N  A  M  S  E  H  L  R  H  F  P  K  C  P  F  I  E  N  Q  -

901  AGCTTCAAGACACTTCAAGATATACACAGTTTCTAATCTGAGCATGCAGACACATGCAGCCC  960
     c   L  Q  D  T  S  R  Y  T  V  S  N  L  S  M  Q  T  H  A  A  R  -

961  GCTTTAAAACATTCTTTAACTGGCCCTCTAGTGTTCTAGTAATCCTGAGCAGCTTGCAA  1020
     c   F  K  T  F  F  N  W  P  S  S  V  L  V  N  P  E  Q  L  A  S  -

1021 GTGCGGGTTTTATTATGTGGTAACAGTGATGATGTCAAATGCTTTTGCTGTGATGGTG  1080
     c   A  G  F  Y  Y  V  G  N  S  D  D  V  K  C  F  C  C  D  G  G  -
```

FIG. 2 (PAGE 3 OF 8)

HUMAN hiap-1

```
     GACTCAGGTGTGTTGGGAATCTGGAGATGATCCATGGGTTCAACATGCCAAGTGGTTCCAA
1081 ------+---------+---------+---------+---------+---------+---- 1140
       L  R  C  W  E  S  G  D  D  P  W  V  Q  H  A  K  W  F  P  R  -

GGTGTGAGTACTTGATAAGAATTAAAGGACAGGAGTTCATCCGTCAAGTTCAAGCCAGTT
1141 ------+---------+---------+---------+---------+---------+---- 1200
       C  E  Y  L  I  R  I  K  G  Q  E  F  I  R  Q  V  Q  A  S  Y  -

ACCCTCATCTACTTGAACAGCTGCTATCCACATCAGACAGCCCAGGAGATGAAAATGCAG
1201 ------+---------+---------+---------+---------+---------+---- 1260
       P  H  L  L  E  Q  L  L  S  T  S  D  S  P  G  D  E  N  A  E  -

AGTCATCAATTATCCATTGGAACCTGGAGAAGACCATTCAGAAGATGCAATCATGATGA
1261 ------+---------+---------+---------+---------+---------+---- 1320
       S  S  I  H  L  E  P  G  E  D  H  S  E  D  A  I  M  M  N  -

ATACTCCTGTGATTAATGCTGCCGTGGAAATGGGCTTTAGTAGAAGCCTGGTAAAACAGA
1321 ------+---------+---------+---------+---------+---------+---- 1380
       T  P  V  I  N  A  A  V  E  M  G  F  S  R  S  L  V  K  Q  T  -

CAGTTCAGAGAAAAATCCTAGCAACTGGAGAGAATTATAGACTAGTCAATGATCTTGTGT
1381 ------+---------+---------+---------+---------+---------+---- 1440
       V  Q  R  K  I  L  A  T  G  E  N  Y  R  L  V  N  D  L  V  L  -
```

FIG. 2 (PAGE 4 OF 8)

HUMAN hiap-1

```
       TAGACTTACTCAATGCAGAAGATGAAATAAGGAAGAGGAGAGAAGAGCAACTGAGG
1441   ------+---------+---------+---------+---------+---------+  1500
        D  L  L  N  A  E  D  E  I  R  E  E  E  E  R  A  T  E  E  -

AAAAGAATCAAATGATTTATTATTAATCCGGAAGAATAGAATGGCACTTTTTCAACATT
1501   ------+---------+---------+---------+---------+---------+  1560
        K  E  S  N  D  L  L  L  I  R  K  N  R  M  A  L  F  Q  H  L  -

TGACTTGTGTAATTCCAATCCTGGATAGTCTCTACTAACTGCCGGAATTATTAATGAACAAG
1561   ------+---------+---------+---------+---------+---------+  1620
        T  C  V  I  P  I  L  D  S  L  L  T  A  G  I  I  N  E  Q  E  -

AACATGATGTTATTAAACAGAAGACACAGACGTCTTTTACAAGCAAGAGAACTGATTGATA
1621   ------+---------+---------+---------+---------+---------+  1680
        H  D  V  I  K  Q  K  T  Q  T  S  L  Q  A  R  E  L  I  D  T  -

CGATTTTTAGTAAAAGGAAATATTGCAGCCACTGTATTCAGAAACTCTCTGCAAGAAGCTG
1681   ------+---------+---------+---------+---------+---------+  1740
        I  L  V  K  G  N  I  A  A  T  V  F  R  N  S  L  Q  E  A  E  -

AAGCTGTGTTATATGAGCATTTATTGTGCAACAGGACATAAATATATTCCCACAGAAG
1741   ------+---------+---------+---------+---------+---------+  1800
        A  V  L  Y  E  H  L  F  V  Q  Q  D  I  K  Y  I  P  T  E  D  -
```

FIG. 2 (PAGE 5 OF 8)

HUMAN hiap-1

```
      ATGTTTCAGATCTACCAGTGGAAGAACAATTGCGGAGACTACCAGAAGAAAGAACATGTA
1801  ------------------------------------------------------------  1860
       V  S  D  L  P  V  E  E  Q  L  R  R  L  P  E  E  R  T  C  K

AAGTGTGTATGGACAAAGAAGTGTCCATAGTGTTTATTCCTTGTGGTCATCTAGTAGTAT
1861  ------------------------------------------------------------  1920
       V  C  M  D  K  E  V  S  I  V  F  I  P  C  G  H  L  V  V  C

GCAAAGATTGTGCTCCTTCTTTAAGAAGTGTCCTATTTGTAGGAGTACAATCAAGGGTA
1921  ------------------------------------------------------------  1980
       K  D  C  A  P  S  L  R  K  C  P  I  C  R  S  T  I  K  G  T

CAGTTCGTACATTCTTTCATGAAGAAGAACCAAAACATCGTCTAAACTTTAGAATTAAT
1981  ------------------------------------------------------------  2040
       V  R  T  F  L  S  *

TTATTAAATGTATTATAACTTTAACTTTTATCCTAATTTGGTTTCCTTAAAATTTTATT
2041  ------------------------------------------------------------  2100

TATTTACAACTCAAAAACATTGTTTTGTGTAACATATTTATATATGTATCTAAACCATA
2101  ------------------------------------------------------------  2160
```

FIG. 2 (PAGE 6 OF 8)

HUMAN hiap-1

```
      TGAACATATATTTTTAGAAACTAAGAGAATGATAGGCTTTTGTTCTTATGAACGAAAAA
2161  ------------------------------------------------------------  2220
                                                                    |
      GAGGTAGCACTACAAACACACAATATTCAATTCAAATTTCAGCATTATTGAAATTGTAAGTG
2221  ------------------------------------------------------------  2280
                                                                    |
      AAGTAAAACTTAAGATATTTGAGTTAACCTTTAAGAATTTTAAATATATTTTGGCATTGTAC
2281  ------------------------------------------------------------  2340
                                                                    |
      TAATACCGGGAACATGAAGCCAGGTGTGGTGGTATGTACCTGTAGTCCCAGGCTGAGGCA
2341  ------------------------------------------------------------  2400
                                                                    |
      AGAGAATTACTTGAGCCCAGGAGTTTGAATCCATCCTGGGCAGCATACTGAGACCCTGCC
2401  ------------------------------------------------------------  2460
                                                                    |
      TTTAAAAACXAACAGXACCAAAXCCAAACACCAGGGACACATTTCTCTGTCTTTTTGAT
2461  ------------------------------------------------------------  2520
                                                                    |
``` c    c    c    c    c    c

FIG. 2  (PAGE 7 OF 8)

HUMAN hiap-1

```
2521 CAGTGTCCTATACATCGAAGGTGTGCATATATGTTGAATCACATTTTAGGGACATGGTGT 2580
2581 TTTTATAAAGAATTCTGTGAGXAAAAATTTAATAAAGCAACCXAAATTACTCTTAAAAAA 2640
2641 AAAAAAAAAAAAAAACTCGAGGGGCCCGTACCAAT 2676
```

FIG. 2 (PAGE 8 OF 8)

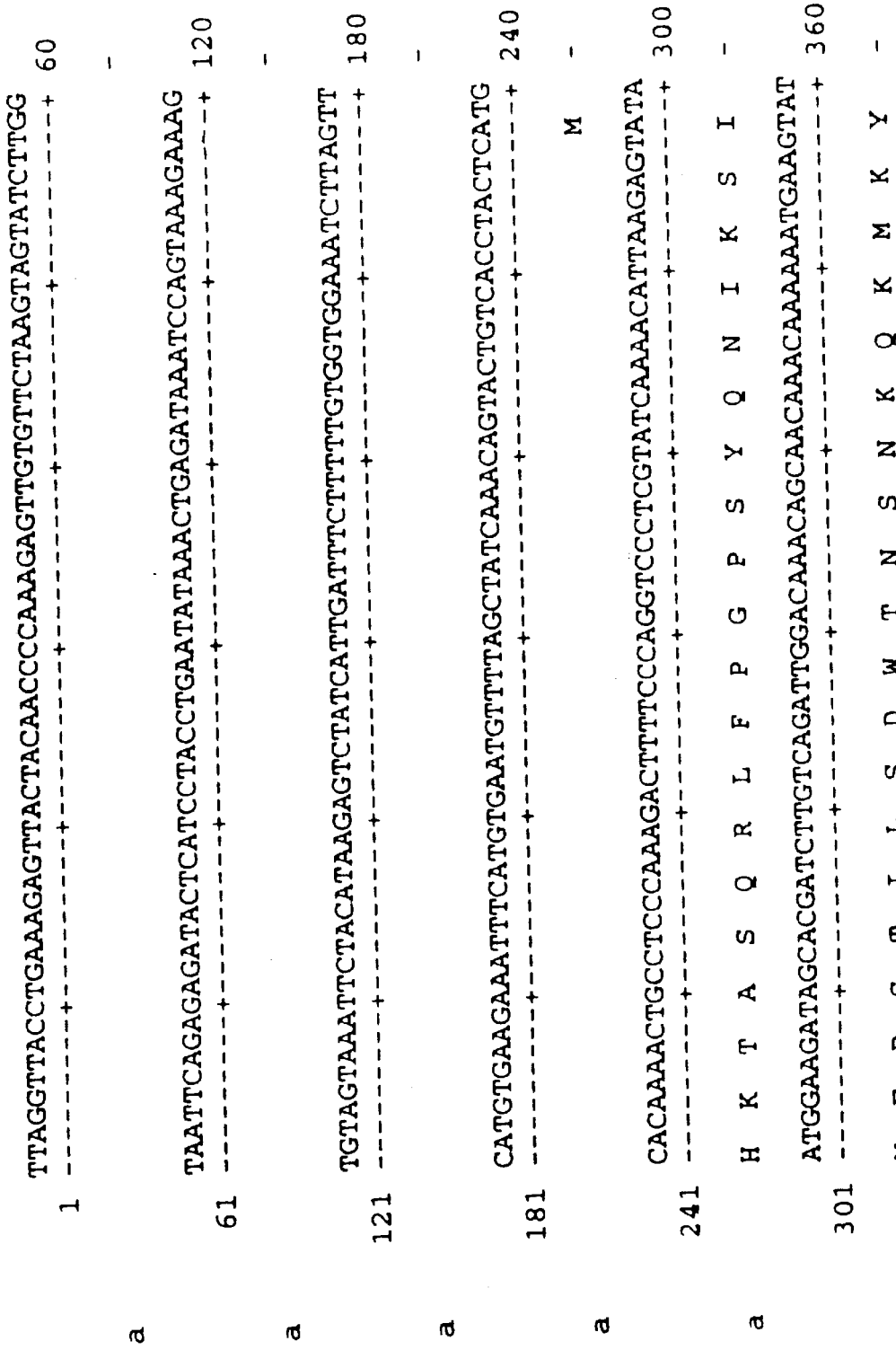
FIG. 3 (PAGE 1 OF 7)

HUMAN hiap-2

```
     GACTTTCCTGTGAACTCTACAGAATGTCTACATATTCAACTTTCCCGCCGGGGTGCCT
361  ---------+---------+---------+---------+---------+---------+  420
      D  F  S  C  E  L  Y  R  M  S  T  Y  S  T  F  P  A  G  V  P

GTCTCAGAAAGGAGTCTTGCTCGTGCTGGTTTTTATTATACTGGTGTGAATGACAAGGTC
421  ---------+---------+---------+---------+---------+---------+  480
      V  S  E  R  S  L  A  R  A  G  F  Y  Y  T  G  V  N  D  K  V

AAATGCTTCTGTGTTGCCTGATGCTGGATAACTGGAAACTAGGAGACAGTCCTATTCAA
481  ---------+---------+---------+---------+---------+---------+  540
      K  C  F  C  C  G  L  M  L  D  N  W  K  L  G  D  S  P  I  Q

AAGCATAAACAGTTGTATCCTAGCTGTAGTTTCATTCAGAATCTGGTTTCAGTAGTCTG
541  ---------+---------+---------+---------+---------+---------+  600
      K  H  K  Q  L  Y  P  S  C  S  F  I  Q  N  L  V  S  A  S  L

GGATCCACCTCTAAGAATACGTCTCCAATGAGAAACAGTTTTGCACATTCATTATCTCCC
601  ---------+---------+---------+---------+---------+---------+  660
      G  S  T  S  K  N  T  S  P  M  R  N  S  F  A  H  S  L  S  P

ACCTTGGAACATAGTAGTCTTGTTCAGTGGTTCTTACTCCAGCCTTCCTCCAAACCCTCTT
661  ---------+---------+---------+---------+---------+---------+  720
      T  L  E  H  S  S  L  F  S  G  S  Y  S  S  L  P  P  N  P  L
```

FIG. 3 (PAGE 2 OF 7)

HUMAN hiap-2

```
721  AATTCTAGAGCAGTTGAAGACATCTCTTCATCGAGGACTAACCCCTACAGTTATGCAATG  780
   a   N  S  R  A  V  E  D  I  S  S  S  R  T  N  P  Y  S  Y  A  M

781  AGTACTGAAGAAGCCAGATTTCTTACCTACCATATGTGGCCATTAACTTTTTTGTCACCA  840
   a   S  T  E  E  A  R  F  L  T  Y  H  M  W  P  L  T  F  L  S  P

841  TCAGAATTGGCAAGAGCTGGTTTTATTATATAGGACCTGGAGATAGGGTAGCCTGCTTT   900
   a   S  E  L  A  R  A  G  F  Y  Y  I  G  P  G  D  R  V  A  C  F

901  GCCTGTGTGGGAAGCTCAGTAACTGGGAACCAAAGGATGATGCTATGTCAGAACACCGG   960
   a   A  C  G  G  K  L  S  N  W  E  P  K  D  D  A  M  S  E  H  R

961  AGGCATTTTCCCAACTGTCCATTTTTGGAAAATTCTCTAGAAACTCTGAGGTTTAGCATT 1020
   a   R  H  F  P  N  C  P  F  L  E  N  S  L  E  T  L  R  F  S  I

1021 TCAAATCTGAGCATGCAGACACATGAGAACATTTATGTACTGGCCATCT           1080
   a   S  N  L  S  M  Q  T  H  A  A  R  M  R  T  F  M  Y  W  P  S
```

FIG. 3 (PAGE 3 OF 7)

HUMAN hiap-2

```
1081  AGTGTTCCAGTTCAGCCTGAGCAGCTTGCAAGTGCTGGTTTTATTATGTGGGTCGCAAT  1140
      ---------+---------+---------+---------+---------+---------+
       S  V  P  V  Q  P  E  Q  L  A  S  A  G  F  Y  Y  V  G  R  N

1141  GATGATGTCAAATGCTTTGGTTGTGATGGTGGCTTGAGGTGTTGGGAATCTGGAGATGAT  1200
      ---------+---------+---------+---------+---------+---------+
       D  D  V  K  C  F  G  C  D  G  G  L  R  C  W  E  S  G  D  D

1201  CCATGGGTAGAACATGCCAAGTGGTTTCCAAGGTGTGAGTTCTTGATACGAATGAAAGGC  1260
      ---------+---------+---------+---------+---------+---------+
       P  W  V  E  H  A  K  W  F  P  R  C  E  F  L  I  R  M  K  G

1261  CAAGAGTTTGTTGATGAGATTCAAGGTAGATATCCTCATCTTCTTGAACAGCTGTTGTCA  1320
      ---------+---------+---------+---------+---------+---------+
       Q  E  F  V  D  E  I  Q  G  R  Y  P  H  L  L  E  Q  L  L  S

1321  ACTTCAGATACCACTGGAGAAGAAAATGCTGACCCACCAATTATTCATTTTGGACCTGGA  1380
      ---------+---------+---------+---------+---------+---------+
       T  S  D  T  T  G  E  E  N  A  D  P  P  I  I  H  F  G  P  G

1381  GAAAGTTCTTCAGAAGATGCTGTCATGATGAATACACCTGTGGTTAAATCTGCCTTGAA  1440
      ---------+---------+---------+---------+---------+---------+
       E  S  S  S  E  D  A  V  M  M  N  T  P  V  V  K  S  A  L  E
```

FIG. 3 (PAGE 4 OF 7)

HUMAN hiap-2

```
1441  ATGGGCTTTAATAGAGACCTGGTGAAACAAACAGTTCTAAGTAAAATCCTGACAACTGGA  1500
      ------+---------+---------+---------+---------+---------+---------+
       M  G  F  N  R  D  L  V  K  Q  T  V  L  S  K  I  L  T  T  G

1501  GAGAACTATAAAACAGTTAATGATATTGTGTCAGCACTTCTTAATGCTGAAGATGAAAAA  1560
      ------+---------+---------+---------+---------+---------+---------+
       E  N  Y  K  T  V  N  D  I  V  S  A  L  L  N  A  E  D  E  K

1561  AGAGAAGAGGAGAAGGAAAAACAAGCTGAAGAAATGGCATCAGATGATTTGTCATTAATT  1620
      ------+---------+---------+---------+---------+---------+---------+
       R  E  E  E  K  E  K  Q  A  E  E  M  A  S  D  D  L  S  L  I

1621  CGGAAGAACAGAATGGCTCTCTTCAACAATTGACATGTGTGCTTCCTATCCTGGATAAT  1680
      ------+---------+---------+---------+---------+---------+---------+
       R  K  N  R  M  A  L  F  Q  Q  L  T  C  V  L  P  I  L  D  N

1681  CTTTTAAAGGCCAATGTAATTAATAAACAGGAACATGATATTATTAAACAAAAAACACAG  1740
      ------+---------+---------+---------+---------+---------+---------+
       L  L  K  A  N  V  I  N  K  Q  E  H  D  I  I  K  Q  K  T  Q

1741  ATACCTTTACAAGCGAGAGAACTGATTGATACCATTTGGGTTAAAGGAAAATGCTGCGCC  1800
      ------+---------+---------+---------+---------+---------+---------+
       I  P  L  Q  A  R  E  L  I  D  T  I  W  V  K  G  N  A  A  A
```

FIG. 3 (PAGE 5 OF 7)

HUMAN hiap-2

```
1801 AACATCTTCAAAAACTGTCTAAAGAAATTGACTCTACATTGTATAAGAACTTATTTGTG 1860
     ----+----+----+----+----+----+----+----+----+----+----+----+
      N  I  F  K  N  C  L  K  E  I  D  S  T  L  Y  K  N  L  F  V

1861 GATAAGAATATGAAGTATATTCCAACAGAAGATGTTTCAGGTCTGTCACTGGAAGAACAA 1920
     ----+----+----+----+----+----+----+----+----+----+----+----+
      D  K  N  M  K  Y  I  P  T  E  D  V  S  G  L  S  L  E  E  Q

1921 TTGAGGAGGTTGCAAGAAGAACGAACTTGTAAAGTGTATGGACAAAGAAGTTTCTGTT 1980
     ----+----+----+----+----+----+----+----+----+----+----+----+
      L  R  R  L  Q  E  E  R  T  C  K  V  C  M  D  K  E  V  S  V

1981 GTATTTATTCCTTGTGGTCATCTGGTAGTATGCCAGGAATGTGCCCCTTCTCTAAGAAAA 2040
     ----+----+----+----+----+----+----+----+----+----+----+----+
      V  F  I  P  C  G  H  L  V  V  C  Q  E  C  A  P  S  L  R  K

2041 TGCCCTATTTGCAGGGGTATAATCAAGGGTACTGTTCGTACATTTCTCTCTTAAAGAAAA 2100
     ----+----+----+----+----+----+----+----+----+----+----+----+
      C  P  I  C  R  G  I  I  K  G  T  V  R  T  F  L  S  *

2101 ATAGTCTATATTTTAACCTGCATAAAAAGGTCTTTAAAATATTGTTGAACACTTGAAGCC 2160
     ----+----+----+----+----+----+----+----+----+----+----+----+
```

FIG. 3 (PAGE 6 OF 7)

HUMAN hiap-2

```
      ATCTAAAGTAAAAAGGAATTATGAGTTTTTCAATTAGTAACATTCATGTTCTAGTCTGC
2161  ------+---------+---------+---------+---------+---------+  2220
                                                                    a

TTTGGTACTAATAATCTTGTTTCTGAAAAGATGGTATCATATATTTAATCTTAATCTGTT
2221  ------+---------+---------+---------+---------+---------+  2280
                                                                    a

TATTTACAAGGAAGATTTATGTTTGGTGAACTATATATTAGTATGTATGTGTACCTAAGGG
2281  ------+---------+---------+---------+---------+---------+  2340
                                                                    a

AGTAGCGTCXCTGCTTGTTATGCATCATTTCAGGAGTTACTGGATTTGTTGTTCTTTCAG
2341  ------+---------+---------+---------+---------+---------+  2400
                                                                    a

AAAGCTTTGAAXACTAAATTATAGTGTAGAAAAGAACTGGAAACCAGGAACTCTGGAGTT
2401  ------+---------+---------+---------+---------+---------+  2460
                                                                    a

CATCAGAGTTATGTGCCGAATTGTCTTTGGTGCTTTTCACTTGTGTTTTAAAATAAGGA
2461  ------+---------+---------+---------+---------+---------+  2520
                                                                    a

TTTTTCTCTTATTTCTCCCCCTAGTTTGTGAGAAACATCTCAATAAAGTGCTTTAAAAAG
2521  ------+---------+---------+---------+---------+---------+  2580
                                                                    a
```

FIG. 3 (PAGE 7 OF 7)

MOUSE xiap

```
    1 GACACTCTGCTGGGGGGCGGGCCGCCCTCCTCCCCTCGGGACCCTCCCCCTCGGGAACCGTGCCCC     60
                                                                        -

61 GCGGCGCTTAGTTAGGACTGAGTGCTTGGCGCGAAAAGGTGGACAAGTCCTATTTTCCA          120
                                                                        -

121 GAGAAGAGATGACTTTTAACAGTTTTGAAGGAACTAGAACTTTTGTACTTGCAGACACCAAT       180
           M  T  F  N  S  F  E  G  T  R  T  F  V  L  A  D  T  N          -

181 AAGGATGAAGAATTTGTAGAAGAGTTTAATAGATTAAAAACATTTGCTAACTTCCCAAGT         240
       K  D  E  E  F  V  E  E  F  N  R  L  K  T  F  A  N  F  P  S        -

241 AGTAGTCCTGTTTCAGCATCAACATTGGCGCGAGCTGGTTTCTTTATACCGGTGAAGGA          300
       S  S  P  V  S  A  S  T  L  A  R  A  G  F  L  Y  T  G  E  G        -

301 GACACCGTGCAATGTTTCAGTTGTCATGCGGCAATAGATAGATGGCAGTATGGAGACTCA         360
       D  T  V  Q  C  F  S  C  H  A  A  I  D  R  W  Q  Y  G  D  S        -
```

FIG. 4 (PAGE 1 OF 6)

MOUSE xiap

```
     GCTGTTGGAAGACACAGGAGAATATCCCCAAATTGCAGATTATCAATGGTTTTATTTT
361  ------+---------+---------+---------+---------+---------+  420
     A  V  G  R  H  R  R  I  S  P  N  C  R  F  I  N  G  F  Y  F

GAAAATGGTGCTGCACAGTCTACAAATCCTGGTATCCAAAATGGCCAGTACAAATCTGAA
421  ------+---------+---------+---------+---------+---------+  480
     E  N  G  A  A  Q  S  T  N  P  G  I  Q  N  G  Q  Y  K  S  E

AACTGTGTGGGAAATAGAAATCCTTTTGCCCCTGACAGGCCACCTGAGACTCATGCTGAT
481  ------+---------+---------+---------+---------+---------+  540
     N  C  V  G  N  R  N  P  F  A  P  D  R  P  P  E  T  H  A  D

TATCTCTTGAGAACTGGACAGGTTGTAGATATTTCAGACACCATATACCCGAGGAACCCT
541  ------+---------+---------+---------+---------+---------+  600
     Y  L  L  R  T  G  Q  V  V  D  I  S  D  T  I  Y  P  R  N  P

GCCATGTGTAGTGAAGAAGCCAGATTGAAGTCATTTCAGAACTGGCCCGACTATGCTCAT
601  ------+---------+---------+---------+---------+---------+  660
     A  M  C  S  E  E  A  R  L  K  S  F  Q  N  W  P  D  Y  A  H

TTAACCCCCAGAGAGTTAGCTAGTGCTGGCCTCTACTACACAGGGGCTGATGATCAAGTG
661  ------+---------+---------+---------+---------+---------+  720
     L  T  P  R  E  L  A  S  A  G  L  Y  Y  T  G  A  D  D  Q  V
```

FIG. 4 (PAGE 2 OF 6)

MOUSE xiap

```
      CAATGCTTTTGTTGTGGGGGAAAACTGAAAAATTGGAACCCTGTGATCGTGCCTGGTCA
721   ------+---------+---------+---------+---------+---------+  780
    a  Q  C  F  C  C  G  G  K  L  K  N  W  E  P  C  D  R  A  W  S

GAACACAGGAGACACTTTCCCAATTGCTTTTTTGTTTTGGGCCGGAACGTTAATGTTCGA
781   ------+---------+---------+---------+---------+---------+  840
    a  E  H  R  R  H  F  P  N  C  F  F  V  L  G  R  N  V  N  V  R

AGTGAATCTGGTGTGAGTTCTGATAGGAATTTCCCAAATTCAACAAACTCTCCAAGAAAT
841   ------+---------+---------+---------+---------+---------+  900
    a  S  E  S  G  V  S  S  D  R  N  F  P  N  S  T  N  S  P  R  N

CCAGCCATGGCAGAATATGAAGCACGGATCGTTACTTTTGGAACATGGATATACTCAGTT
901   ------+---------+---------+---------+---------+---------+  960
    a  P  A  M  A  E  Y  E  A  R  I  V  T  F  G  T  W  I  Y  S  V

AACAAGGAGCAGCTTGCAAGAGCTGGATTTTATGCTTTAGGTGAAGGCGATAAAGTGAAG
961   ------+---------+---------+---------+---------+---------+  1020
    a  N  K  E  Q  L  A  R  A  G  F  Y  A  L  G  E  G  D  K  V  K

TGCTTCCACTGTGGAGGAGGGCTCACGGATTGGAAGCCAAGTGAAGACCCCTGGGACCAG
1021  ------+---------+---------+---------+---------+---------+  1080
    a  C  F  H  C  G  G  G  L  T  D  W  K  P  S  E  D  P  W  D  Q
```

FIG. 4 (PAGE 3 OF 6)

MOUSE xiap

```
1081  CATGCTAAGTGCTACCCAGGGTGCAAATACCTATTGGATGAGAAGGGCAAGAATATATA
      ----+----+----+----+----+----+----+----+----+----+----+----+ 1140
  a    H  A  K  C  Y  P  G  C  K  Y  L  L  D  E  K  G  Q  E  Y  I

1141  AATAATATTCATTTAACCCATCCACTTGAGGAATCTTTGGGAAGAACTGCTGAAAAAACA
      ----+----+----+----+----+----+----+----+----+----+----+----+ 1200
  a    N  N  I  H  L  T  H  P  L  E  E  S  L  G  R  T  A  E  K  T

1201  CCACCGCTAACTAAAAAAATCGATGATACCATCTTCCAGAATCCTATGGTGCAAGAAGCT
      ----+----+----+----+----+----+----+----+----+----+----+----+ 1260
  a    P  P  L  T  K  K  I  D  D  T  I  F  Q  N  P  M  V  Q  E  A

1261  ATACGAATGGGATTTAGCTTCAAGGACCTTGAGGTCCTGATTGCAGATCTTGTGAGTGCTCAGAAA
      ----+----+----+----+----+----+----+----+----+----+----+----+ 1320
  a    I  R  M  G  F  S  F  K  D  L  K  K  T  M  E  E  K  I  Q  T

1321  TCCGGGAGCAGCTATCTATCACTTGAGGTCCTGATTGCAGATCTTGTGAGTGCTCAGAAA
      ----+----+----+----+----+----+----+----+----+----+----+----+ 1380
  a    S  G  S  S  Y  L  S  L  E  V  L  I  A  D  L  V  S  A  Q  K

1381  GATAATACGGAGGATGAGTCAAGTCAAACTTCATTGCAGAAAGACATTAGTACTGAAGAG
      ----+----+----+----+----+----+----+----+----+----+----+----+ 1440
  a    D  N  T  E  D  E  S  S  Q  T  S  L  Q  K  D  I  S  T  E  E
```

FIG. 4 (PAGE 4 OF 6)

MOUSE xiap

```
1441  CAGCTAAGGCGCCTACAAGAGAGAAGCTTTCCAAATCTGTATGGATAGAAATATTGCT  1500
       Q  L  R  R  L  Q  E  E  K  L  S  K  I  C  M  D  R  N  I  A

1501  ATCGTTTTTTTTCCTGTGGACATCTGGCCACTTGTAAACAGTGTGCAGAAGCAGTTGAC  1560
       I  V  F  F  P  C  G  H  L  A  T  C  K  Q  C  A  E  A  V  D

1561  AAATGTCCCATGTGCTACACCGTCATTACGTTCAACCAAAAAATTTTATGTCTTAGTGG  1620
       K  C  P  M  C  Y  T  V  I  T  F  N  Q  K  I  F  M  S  *

1621  GGCACCACATGTTATAGTTCTTCTTGCTCTAATTGAATGTGTAATGGGAGCGAACTTTAAG  1680

1681  TAATCCCTGCATTTGCATTCCATTAGCATCCTGCTGTTTCCAAATGGAGAGACCAATGCTAAC  1740

1741  AGCACTGTTTCCGTCTAAACATTCAATTTCTGGATCTTTCGAGTTATCAGCTGTATCATT  1800
```

FIG. 4 (PAGE 5 OF 6)

MOUSE xiap

```
1801 TAGCCAGTGTTTACTCGATTGAAACCTTAGACAGAGAAGCATTTTATAGCTTTTCACAT
     ---------+---------+---------+---------+---------+---------+ 1860

1861 GTATATTGGTAGTACACTGACTTGATTTCTATATGTAAGTGAATTCATCACCTGCATGTT
     ---------+---------+---------+---------+---------+---------+ 1920

1921 TCATGCCTTTTGCATAAGCTTAACAAATGGAGTGTTCTGTATAAGCATGGAGATGTGATG
     ---------+---------+---------+---------+---------+---------+ 1980

1981 GAATCTGCCCAATGACTTTAATTGGCTTATTGTAAACACGGAAAGAACTGCCCCACGCTG
     ---------+---------+---------+---------+---------+---------+ 2040

2041 CTGGGAGGATAAAGATTGTTTTAGATGCTCACTTCTGTGTTTTAGGATTCTGCCCATTTA
     ---------+---------+---------+---------+---------+---------+ 2100
```

FIG. 4 (PAGE 6 OF 6)

M-hiap-1

```
     GAATTCCGGGAGACCTACACCCCGGAGATCAGAGGTCATTGCTGGCGTTCAGAGCCTAG
  1  ----+----+----+----+----+----+----+----+----+----+----+----+  60
     GAAGTGGGCTGCGGTATCAGCCTAGCAGTAAAACCGACCAGAAGCCATGCACAAAACTAC
 61  ----+----+----+----+----+----+----+----+----+----+----+----+ 120
     ATCCCCAGAGAAAGACTTGTCCCTCCCCTGTCATCTCACCATGAACATGGTTCAA
121  ----+----+----+----+----+----+----+----+----+----+----+----+ 180
                                                M  N  M  V  Q
     GACAGGCGCCTTTCTAGCCAAGCTGATGAAGAGTGCTGACACCTTTGAGTTGAAGTATGAC
181  ----+----+----+----+----+----+----+----+----+----+----+----+ 240
      D  S  A  F  L  A  K  L  M  K  S  A  D  T  F  E  L  K  Y  D
     TTTTCCTGTGAGCTGTACCGATTGTCCACGTATTCAGCTTTTCCAGGGGAGTTCCTGTG
241  ----+----+----+----+----+----+----+----+----+----+----+----+ 300
      F  S  C  E  L  Y  R  L  S  T  Y  S  A  F  P  P  R  G  V  P  V
     TCAGAAAGGAGTCTGGCTCGTGTGCTGGCTTTTACTACACTGGTGCCAATGACAAGGTCAAG
301  ----+----+----+----+----+----+----+----+----+----+----+----+ 360
      S  E  R  S  L  A  R  A  G  F  Y  Y  T  G  A  N  D  K  V  K
     TGCTTCTGCTGTGGCCTGATGCTAGACAACTGGAAACAAGGGGACAGTCCCATGGAGAAG
361  ----+----+----+----+----+----+----+----+----+----+----+----+ 420
      C  F  C  C  G  L  M  L  D  N  W  K  Q  G  D  S  P  M  E  K
```

FIG. 5 (PAGE 1 OF 6)

M-hiap-1

```
421  CACAGAAAGTTGTACCCCAGCTGCAACTTTGTACAGACTTTGAATCCAGCCAACAGTCTG  480
      H  R  K  L  Y  P  S  C  N  F  V  Q  T  L  N  P  A  N  S  L

481  GAAGCTAGTCCTCGGCCTTCTCTTCCTTCCACGGGCGATGAGCACCATGCCTTTGAGCTTT  540
      E  A  S  P  R  P  S  L  P  S  T  A  M  S  T  M  P  L  S  F

541  GCAAGTTCTGAGAATACTGGCTATTTCAGTGGCTCTTACTCGAGCTTTCCCTCAGACCCT  600
      A  S  S  E  N  T  G  Y  F  S  G  S  Y  S  S  F  P  S  D  P

601  GTGAACTTCCGAGCAAATCAAGATTGTCCTGCTTTGAGCACAAGTCCCTACCACTTTGCA  660
      V  N  F  R  A  N  Q  D  C  P  A  L  S  T  S  P  Y  H  F  A

661  ATGAACACAGAAGGCCAGATTACTCACCTATGAAACATGGCCATTGTCTTTTCTGTCA  720
      M  N  T  E  K  A  R  L  L  T  Y  E  T  W  P  L  S  F  L  S

721  CCAGCAAAGCTGGCCAAAGCAGGCTTCTACTACATAGGACCTGGAGATAGAGTGGCCTGC  780
      P  A  K  L  A  K  A  G  F  Y  Y  I  G  P  G  D  R  V  A  C
```

FIG. 5 (PAGE 2 OF 6)

M-hiap-1

```
781  TTTGCGTGCGATGGGAAACTGAGCAACTGGGAACGTAAGGATGATGCTATGTCAGAGCAC  840
      F  A  C  D  G  K  L  S  N  W  E  R  K  D  D  A  M  S  E  H

841  CAGAGGCATTTCCCCAGCTGTCCGTTCTTAAAAGACTTGGGTCAGTCTGCTTCGAGATAC  900
      Q  R  H  F  P  S  C  P  F  L  K  D  L  G  Q  S  A  S  R  Y

901  ACTGTCTCTAACCTGAGCATGCAGACACACGCAGCCCGTATTAGAACATTCTCTAACTGG  960
      T  V  S  N  L  S  M  Q  T  H  A  A  R  I  R  T  F  S  N  W

961  CCTTCTAGTGCACTAGTTCATTCCCAGGAACTTGCAAGTGCGGGCTTTTATTATACAGGA  1020
      P  S  S  A  L  V  H  S  Q  E  L  A  S  A  G  F  Y  Y  T  G

1021 CACAGTGATGATGTCAAGTGTTTATGCTGTGATGGTGGGCTGAGGTGCTGGGAATCTGGA  1080
      H  S  D  D  V  K  C  L  C  C  D  G  G  L  R  C  W  E  S  G

1081 GATGACCCCTGGGTGGAACATGCCAAGTGGTTTCCAAGGTGTGAGTACTTGCTCAGAATC  1140
      D  D  P  W  V  E  H  A  K  W  F  P  R  C  E  Y  L  L  R  I

1141 AAAGGCCAAGAATTTGTCAGCCAAGTTCAAGCCTGCTATCCTCATCTACTTGAGCAGCTA  1200
      K  G  Q  E  F  V  S  Q  V  Q  A  G  Y  P  H  L  L  E  Q  L
```

FIG. 5 (PAGE 3 OF 6)

M-hiap-1

```
       TTATCTAGTCAGACTCCCCAGAGATGAGAATGCAGACGCAGCAATCGTGCATTTTGGC
1201   ---------+---------+---------+---------+---------+---------+  1260
        L  S  T  S  D  S  P  E  D  E  N  A  D  A  A  I  V  H  F  G

CCTGGAGAAAGTTCGGAAGATGTCGTCATGATGAGCACGCCCTGTGGTTAAAGCAGCCTTG
1261   ---------+---------+---------+---------+---------+---------+  1320
        P  G  E  S  S  E  D  V  V  M  M  S  T  P  V  V  K  A  A  L

GAAATGGGCTTCAGTAGGAGCCTGGTGAGACAGACGGTTCAGTGGCAGATCCTGGCCACT
1321   ---------+---------+---------+---------+---------+---------+  1380
        E  M  G  F  S  R  S  L  V  R  Q  T  V  Q  W  Q  I  L  A  T

GGTGAGAACTACAGGACCGTCAGTGACCTCGTTATAGGCTTACTCGATGCAGAAGACGAG
1381   ---------+---------+---------+---------+---------+---------+  1440
        G  E  N  Y  R  T  V  S  D  L  V  I  G  L  L  D  A  E  D  E

ATGAGAGAGCAGATGGAGCAGGCCCAGAGGAGGAGTCAGATGATCTAGCACTA
1441   ---------+---------+---------+---------+---------+---------+  1500
        M  R  E  E  Q  M  E  Q  A  A  E  E  E  E  S  D  D  L  A  L

ATCCGGAAGAACAAAATGGTGCTTTTCCAACATTTGACGTGTGTGACACCAATGCTGTAT
1501   ---------+---------+---------+---------+---------+---------+  1560
        I  R  K  N  K  M  V  L  F  Q  H  L  T  C  V  T  P  M  L  Y
```

FIG. 5 (PAGE 4 OF 6)

M-hiap-1

```
      TGCCTCCTAAGTGCAAGGGCCATCACTGAACAGGAGTGCAATGCTGTGAAACAGAAACCA
1561  ------+---------+---------+---------+---------+---------+  1620
       C  L  L  S  A  R  A  I  T  E  Q  E  C  N  A  V  K  Q  K  P

CACACCTTACAAGCAAGCACACTGATTGATACTGTGTTAGCAAAAGGAAACACTGCAGCA
1621  ------+---------+---------+---------+---------+---------+  1680
       H  T  L  Q  A  S  T  L  I  D  T  V  L  A  K  G  N  T  A  A

ACCTCATTCAGAAACTCCCTTCGGGAAATTGACCCTGCGTTATACAGAGATATATTTGTG
1681  ------+---------+---------+---------+---------+---------+  1740
       T  S  F  R  N  S  L  R  E  I  D  P  A  L  Y  R  D  I  F  V

CAACAGGACATTAGGAGTCTTCCCACAGATGACATTGCAGCTCTACCAATGGAAGAACAG
1741  ------+---------+---------+---------+---------+---------+  1800
       Q  Q  D  I  R  S  L  P  T  D  D  I  A  A  L  P  M  E  E  Q

TTGCGGCCCCTCCCGGAGGACAGAATGTGTAAAGTGTGTATGGACCGAGAGGTATCCATC
1801  ------+---------+---------+---------+---------+---------+  1860
       L  R  P  L  P  E  D  R  M  C  K  V  C  M  D  R  E  V  S  I

GTGTTCATTCCCTGTGGCCATCTGGTCGTGTGCAAAGACTGCGCTCCCTCTCTGAGGAAG
1861  ------+---------+---------+---------+---------+---------+  1920
       V  F  I  P  C  G  H  L  V  V  C  K  D  C  A  P  S  L  R  K
```

FIG. 5 (PAGE 5 OF 6)

M-hiap-1

```
       TGTCCCATCTGTAGAGGGACCATCAAGGCGCAGTGCGCACATTTCTCCTGAACAAGA
1921   ------------------------------------------------------------   1980
        C  P  I  C  R  G  T  I  K  G  T  V  R  T  F  L  S  *

CTAATGGTCCATGGCTGCAACTTCAGCCAGGAGAAGTTCACTGTCACTCCCAGTTCCAT
1981   ------------------------------------------------------------   2040

TCGGAACTTGAGGCCAGCCTGGATAGCACGAGACACCGCCAAACACACAAATATAAACAT
2041   ------------------------------------------------------------   2100

GAAAAACTTTGTCTGAAGTCAAGAATGAATTACTTATATAATAATTTTAATTGGT
2101   ------------------------------------------------------------   2160

TTCCTTAAAAGTGCTATTTGTTCCCAACTCAGAAAATTGTTTTCTGTAAACATATTTACA
2161   ------------------------------------------------------------   2220

TACTACCTGCATCTAAAGTATTCATATATTCATATATTCAGATGTCATGAGAGAGGGTTT
2221   ------------------------------------------------------------   2280

TGTTCTTGTTCCTGAAAAGCTGGTTTATCATCTGATCAGCATATACTGCGCAACGGGCAG
2281   ------------------------------------------------------------   2340

GGCTAGAATCCATGAACCAAGCTGCAAAGATCTCACGCTAAATAAGGCGGAAAGATTTGG
2341   ------------------------------------------------------------   2400

AGAAACGAAAGGAAATTCTTTTCCTGTCCAATGTATACTCTTCAGACTAATGACCTCTTCC
2401   ------------------------------------------------------------   2460

TATCAAGCCTTCTA
2461   --------------   2474
```

FIG. 5 (PAGE 6 OF 6)

M-hiap-2

```
      CTGTGGTGGAGATCTATTGTCCAAGTGGTGAGAAACTTCATCTGAAGTTTAAGCGGTCA
  1   ---------+---------+---------+---------+---------+---------+   60
      GAAATACTACTACTCATGGACAAAACTGTCTCCCAGAGACTCGCCCAAGGTACCTTTA
 61   ---------+---------+---------+---------+---------+---------+  120
      CACCCAAAAACTTAAACGTATAATGGAGAAGAGCACAATCTTGTCAAATTGGACAAAGGA
121   ---------+---------+---------+---------+---------+---------+  180
                              M  E  K  S  T  I  L  S  N  W  T  K  E

GAGCGAAGAAAAAATGAAGTTTGACTTTTCGTGTGAACTCTACCGAATGTCTACATATTC
181   ---------+---------+---------+---------+---------+---------+  240
       S  E  E  K  M  K  F  D  F  S  C  E  L  Y  R  M  S  T  Y  S

AGCTTTTCCCAGGGAGTTCCTGTCTCAGAGAGGAGTCTGGCTCGTGCTGGCTTTTATTA
241   ---------+---------+---------+---------+---------+---------+  300
       A  F  P  R  G  V  P  V  S  E  R  S  L  A  R  A  G  F  Y  Y

TACAGGTGTGAATGACAAAGTCAAGTGCTTCTGCTGTGGCCTGATGTTGGATAACTGGAA
301   ---------+---------+---------+---------+---------+---------+  360
       T  G  V  N  D  K  V  K  C  F  C  C  G  L  M  L  D  N  W  K

ACAAGGGGACAGTCCTGTTGAAAAGCACAGACAGTTCTATCCCAGCTGCAGCTTTGTACA
361   ---------+---------+---------+---------+---------+---------+  420
       Q  G  D  S  P  V  E  K  H  R  Q  F  Y  P  S  C  S  F  V  Q
```

FIG. 6 (PAGE 1 OF 6)

M-hiap-2

```
         GACTCTGCTTTCAGCCAGTCTGCAGTCTCCATCTAAGAATATGTCTCCTGTGAAAAGTAG
421      ------+---------+---------+---------+---------+---------+   480
          T  L  L  S  A  S  L  Q  S  P  S  K  N  M  S  P  V  K  S  R

ATTTGCACATTCGTCTCACCTCTGGAACGAGGTGGCATTCACTCCAACCTGTGCTCTAGCCC
481      ------+---------+---------+---------+---------+---------+   540
          F  A  H  S  S  P  L  E  R  G  G  I  H  S  N  L  C  S  S  P

TCTTAATTCTAGAGCAGTGGAAGACTTCTCATCAAGGATGGATCCCTGCAGCTATGCCAT
541      ------+---------+---------+---------+---------+---------+   600
          L  N  S  R  A  V  E  D  F  S  S  R  M  D  P  C  S  Y  A  M

GAGTACAGAAGAGGCCAGATTTCTTACTTACAGTATGTGGCCTTTAAGTTTTCTGTCACC
601      ------+---------+---------+---------+---------+---------+   660
          S  T  E  E  A  R  F  L  T  Y  S  M  W  P  L  S  F  L  S  P

AGCCAGAGCTGGCCAGAGCTGCTTCTATTACATAGGGCCTGGAGACAGGGTGGCCTGTTT
661      ------+---------+---------+---------+---------+---------+   720
          A  E  L  A  R  A  G  F  Y  Y  I  G  P  G  D  R  V  A  C  F

TGCCTGTGGTGGGAAACTGAGCAACTGGGAACCAAAGGATTATGCTATGTCAGAGCACCG
721      ------+---------+---------+---------+---------+---------+   780
          A  C  G  G  K  L  S  N  W  E  P  K  D  Y  A  M  S  E  H  R
```

FIG. 6 (PAGE 2 OF 6)

M-hiap-2

```
         CAGACATTTTCCCCACTGTCCCATTTCTGGAAATACTTCAGAAACACAGAGTTTAGTAT
781      ------------------------------------------------------------  + 840
          R  H  F  P  H  C  P  F  L  E  N  T  S  E  T  Q  R  F  S  I  -

ATCAAATCTAAGTATGCAGAGACACACTCTGCTCGATTGAGGACATTCTGTACTGGCCACC
841      ------------------------------------------------------------  + 900
          S  N  L  S  M  Q  T  H  S  A  R  L  R  T  F  L  Y  W  P  P  -

TAGTGTTCCTGTTCAGCCCGAGCAGCTTGCAAGTGCTGATTCTATTACGTGGATCGCAA
901      ------------------------------------------------------------  + 960
          S  V  P  V  Q  P  E  Q  L  A  S  A  G  F  Y  Y  V  D  R  N  -

TGATGATGTCAAGTGCCTTTGTTGTGATGGCTTGAGAGTGTTGGGAACCTGGAGATGA
961      ------------------------------------------------------------  + 1020
          D  D  V  K  C  L  C  C  D  G  G  L  R  C  W  E  P  G  D  D  -

CCCCTGGATAGAACACGCCAAATGGTTTCCAAGGTGTGAGTTCTTGATACGGATGAAGGG
1021     ------------------------------------------------------------  + 1080
          P  W  I  E  H  A  K  W  F  P  R  C  E  F  L  I  R  M  K  G  -

TCAGGAGTTTGTTGATGAGATTCAAGCTAGATATCCTCATCTTCTTGAGCAGCTGTTGTC
1081     ------------------------------------------------------------  + 1140
          Q  E  F  V  D  E  I  Q  A  R  Y  P  H  L  L  E  Q  L  L  S  -
```

FIG. 6 (PAGE 3 OF 6)

M-hiap-2

```
      CACTTCAGACACCCCAGGAGAAGAAAATGCTGACCCTACAGAGACAGTGGTGCATTTTGG
1141  ------+---------+---------+---------+---------+---------+  1200
       T  S  D  T  P  G  E  E  N  A  D  P  T  E  T  V  V  H  F  G  -

CCCTGGAGAAAGTTCGAAAGATGTCGTCATGATGAGCACGCCTGTGGTTAAAGCAGCCTT
1201  ------+---------+---------+---------+---------+---------+  1260
       P  G  E  S  S  K  D  V  V  M  M  S  T  P  V  V  K  A  A  L  -

GGAAATGGGCTTCAGTAGGAGCCTGGTGAGACAGACGGTTCAGCGGCAGATCCTGGCCAC
1261  ------+---------+---------+---------+---------+---------+  1320
       E  M  G  F  S  R  S  L  V  R  Q  T  V  Q  R  Q  I  L  A  T  -

TGGTGAGAACTACAGGACCGTCAATGATATTGTCTCAGTACTTTTGAATGCTGAAGATGA
1321  ------+---------+---------+---------+---------+---------+  1380
       G  E  N  Y  R  T  V  N  D  I  V  S  V  L  L  N  A  E  D  E  -

GAGAAGAGAAGAGGAGAAGGAAAGACAGACTGAAGAAGATGGCATCAGGTGACTTATCACT
1381  ------+---------+---------+---------+---------+---------+  1440
       R  R  E  E  K  E  R  Q  T  E  E  M  A  S  G  D  L  S  L  -

GATTCGGAAGAATAGAATGGCCCTCTTTCAACAGTTGACACATGTCCTTCCTATCCTGGA
1441  ------+---------+---------+---------+---------+---------+  1500
       I  R  K  N  R  M  A  L  F  Q  Q  L  T  H  V  L  P  I  L  D  -
```

FIG. 6 (PAGE 4 OF 6)

M-hiap-2

```
        TAATCTTCTTGAGGCCAGTGTAATTACAAACAGGAACATGATATTATTAGACAGAAAAC
1501    ------+---------+---------+---------+---------+---------+   1560
         N  L  E  A  S  V  I  T  K  Q  E  H  D  I  I  R  Q  K  T

ACAGATACCCTTACAAGCAAGAGAGCTTATTGACACCGTTTTAGTCAAGGGAAATGCTGC
1561    ------+---------+---------+---------+---------+---------+   1620
         Q  I  P  L  Q  A  R  E  L  I  D  T  V  L  V  K  G  N  A  A

AGCCAACATCTTCAAAAACTCTCTGAAGGGAATTGACTCCACGTTATATGAAAACTTATT
1621    ------+---------+---------+---------+---------+---------+   1680
         A  N  I  F  K  N  S  L  K  G  I  D  S  T  L  Y  E  N  L  F

TGTGGAAAAGAATATGAAGTATATATTCCAACAGAAGACGTTTCAGGCTTGTCATTGGAAGA
1681    ------+---------+---------+---------+---------+---------+   1740
         V  E  K  N  M  K  Y  I  P  T  E  D  V  S  G  L  S  L  E  E

GCAGTTGCGGAGATTACAAGAAGAACTTGCAAAGTGTATGGACAGAGAGGTTTC
1741    ------+---------+---------+---------+---------+---------+   1800
         Q  L  R  R  L  Q  E  E  R  T  C  K  V  C  M  D  R  E  V  S

TATTGTGTTCATTCCGTGTGGTCATCTAGTAGTCTGCCAGGAATGTGCCCCTTCTCTAAG
1801    ------+---------+---------+---------+---------+---------+   1860
         I  V  F  I  P  C  G  H  L  V  V  C  Q  E  C  A  P  S  L  R
```

FIG. 6 (PAGE 5 OF 6)

M-hiap-2

```
      GAAGTGCCCCATCTGCAGGGGACAATCAAGGGGACTGTGCGCACATTTCTCTCATGAGT
1861  ------------------------------------------------------------  1920
       K  C  P  I  C  R  G  T  I  K  G  T  V  R  T  F  L  S  *

GAAGAATGGTCTGAAAGTATTGTTGGACATCAGAAGCTGTCAGAACAAAGAATGAACTAC
1921  ------------------------------------------------------------  1980

TGATTCAGCTCTTCAGGACATTCTACTCTCTTCAAGATTAGTAATCTTGCTTTAT
1981  ------------------------------------------------------------  2040

GAAGGGTAGCATTGTATATTTAAGCTTAGTCTGTTGCAAGGGAAGGTCTATGCTGTTGAG
2041  ------------------------------------------------------------  2100

CTACAGGACTGTGTCTGTTCCAGAGCAGGAGTTGGGATGCTTGCTGTATGTCCTTCAGGA
2101  ------------------------------------------------------------  2160

CTTCTTGGGATTTGGGAAATTTGGAATCCAGTGATGTGAGCTCAGAAA
2161  ------------------------------------------------------------  2220

TCCTGGAACCAGTGACTCTGTACTCAGTAGATAGGGTACCCTGTACTTCTTGGTGCTTT
2221  ------------------------------------------------------------  2280

TCCAGTCTGGGAAATAAGGAGGAATCTGCTGCTGGTAAAAATTTGCTGGATGTGAGAAAT
2281  ------------------------------------------------------------  2340

AGATGAAAGTGTTTCGGGTGGGGCCGTGCATCAGTGTAGTGTGCAGGGATGTATGCAG
2341  ------------------------------------------------------------  2400

GCCAAACACTGTGTAG
2401  ----------------  2416
```

FIG. 6 (PAGE 6 OF 6)

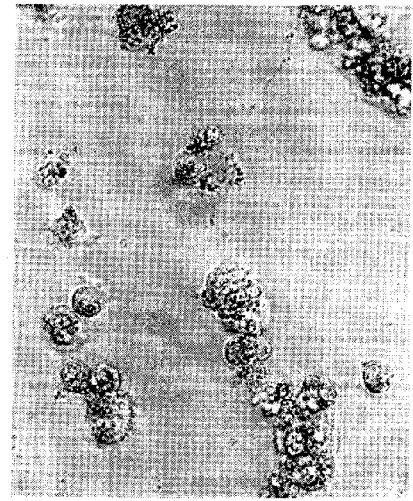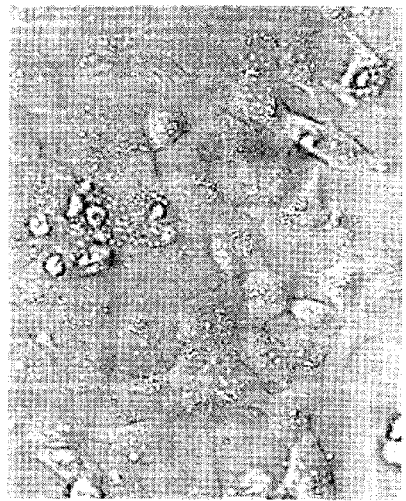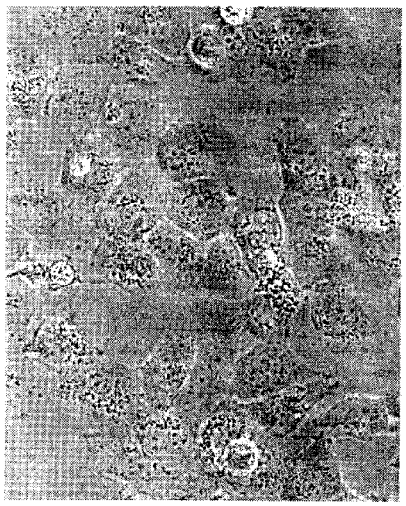
Fig. 9D

1 TTGCAGGTAC TTAGAATTTT TCCTGAGCCA CCCTCTAGAG GGCAGTGTTA

51 CATATATATC TGTAATTATC CAGTTACAAC AAAAAAAGGG CTCTCATTCA

101 TGCATGAAAA TCAGAAATAT TTCATACTCT TAAAGAACAC ATTGGAACCA

151 ATATTATGAT TAAAACATAT TTGCTAAGC AAAGAGATAT TAAAAATTAA

201 TTCATTAACA TTCTGAACAT TTTTAACTT GTAAAAACAA CTTTGATGCC

251 TTGAATATAT AATGATTCAT TATAACAATT ATGCATAGAT TTTAATAATC

301 TGCATATTTT ATGCTTTCAT GTTTTCCTA ATTAATGATT TGACATGGTT

351 AATAATTATA ATATATTCTG CATCACAGTT TACATATTTA TGTAAAATAA

401 GCATTTAAAA ATTATTAGTT TTATTCTGCC TGCTTAAATA TTACTTTCCT

451 CAAAAGAGA AAACAAAAAT GCTAGATTTT ACTTTATGAC TTGAATGATG

501 TGGTAATGTC GAACTCTAGT ATTTAGAATT AGAATGTTTC TTAGCGGTCG

551 TGTAGTTATT TTTATGTCAT AAGTGGATAA TTGTTAGCT CCTATAACAA

601 AAGTCTGTTG CTTGTGTTTC ACATTTGGA TTTCCTAATA TAATGTTCTC

651 TTTTTAGAAA AGGTGGACAA GTCCTATTTT CAAGAGAAGA TGACTTTTAA

701 CAGTTTTGAA GGATCTAAAA CTTGTGTACC TGCAGACATC AATAAGGAAG

751 AAGAATTTGT AGAAGAGTTT AATAGATTAA AAACTTTTGC TAATTTTCCA

801 AGTGGTAGTC CTGTTTCAGC ATCAACACTG GCACGAGCAG GGTTTCTTTA

851 TACTGGTGAA GGAGATACCG TGCGGTGCTT TAGTTGTCAT GCAGCTGTAG

901 ATAGATGGCA ATATGGAGAC TCAGCAGTTG GAAGACACAG GAAAGTATCC

951 CCAAATTGCA GATTTATCAA CGGCTTTTAT CTTGAAAATA GTGCCACGCA

Fig. 15 (Page 1 of 3)

1001 GTCTACAAAT TCTGGTATCC AGAATGGTCA GTACAAAGTT GAAAACTATC

1051 TGGGAAGCAG AGATCATTTT GCCTTAGACA GGCCATCTGA GACACATGCA

1101 GACTATCTTT TGAGAACTGG GCAGGTTGTA GATATATCAG ACACCATATA

1151 CCCGAGGAAC CCTGCCATGT ATTGTGAAGA AGCTAGATTA AAGTCCTTTC

1201 AGAACTGGCC AGACTATGCT CACCTAACCC CAAGAGAGTT AGCAAGTGCT

1251 GGACTCTACT ACACAGGTAT TGGTGACCAA GTGCAGTGCT TTTGTTGTGG

1301 TGGAAAACTG AAAAATTGGG AACCTTGTGA TCGTGCCTGG TCAGAACACA

1351 GGCGACACTT TCCTAATTGC TTCTTTGTTT TGGGCCGGAA TCTTAATATT

1401 CGAAGTGAAT CTGATGCTGT GAGTTCTGAT AGGAATTTCC CAAATTCAAC

1451 AAATCTTCCA AGAAATCCAT CCATGGCAGA TTATGAAGCA CGGATCTTTA

1501 CTTTTGGGAC ATGGATATAC TCAGTTAACA AGGAGCAGCT TGCAAGAGCT

1551 GGATTTTATG CTTTAGGTGA AGGTGATAAA GTAAAGTGCT TCACTGTGG

1601 AGGAGGGCTA ACTGATTGGA AGCCCAGTGA AGACCCTTGG GAACAACATG

1651 CTAAATGGTA TCCAGGGTGC AAATATCTGT TAGAACAGAA GGGACAAGAA

1701 TATATAAACA ATATTCATTT AACTCATTCA CTTGAGGAGT GTCTGGTAAG

1751 AACTACTGAG AAAACACCAT CACTAACTAG AAGAATTGAT GATACCATCT

1801 TCCAAAATCC TATGGTACAA GAAGCTATAC GAATGGGGTT CAGTTTCAAG

1851 GACATTAAGA AAATAATGGA GGAAAAAATT CAGATATCTG GGAGCAACTA

1901 TAAATCACTT GAGGTTCTGG TTGCAGATCT AGTGAATGCT CAGAAAGACA

1951 GTATGCAAGA TGAGTCAAGT CAGACTTCAT TACAGAAAGA GATTAGTACT

2001 GAAGAGCAGC TAAGGCGCCT GCAAGAGGAG AAGCTTTGCA AAATCTGTAT

Fig. 15 (Page 2 of 3)

2051 GGATAGAAAT ATTGCTATCG TTTTTGTTCC TTGTGGACAT CTAGTCACTT

2101 GTAAACAATG TGCTGAAGCA GTTGACAAGT GTCCCATGTG CTACACAGTC

2151 ATTACTTTCA AGCAAAAAAT TTTTATGTCT TAATCTAACT CTATAGTAGG

2201 CATGTTATGT TGTTCTTATT ACCCTGATTG AATGTGTGAT GTGAACTGAC

2251 TTAAGTAAT CAGGATTGAA TTCCATTAGC ATTTGCTACC AAGTAGGAAA

2301 AAAAATGTAC ATGGCAGTGT TTAGTTGGC AATATAATCT TTGAATTTCT

2351 TGATTTTTCA GGGTATTAGC TGTATTATCC ATTTTTTTA CTGTTATTTA

2401 ATTGAAACCA TAGACTAAGA ATAAGAAGCA TCATACTATA ACTGAACACA

2451 ATGTGTATTC ATAGTATACT GATTTAATTT CTAAGTGTAA GTGAATTAAT

2501 CATCTGGATT TTTTATTCTT TTCAGATAGG CTTAACAAAT GGAGCTTTCT

2551 GTATATAAAT GTGGAGATTA GAGTTAATCT CCCCAATCAC ATAATTTGTT

2601 TTGTGTGAAA AAGGAATAAA TTGTTCCATG CTGGTGGAAA GATAGAGATT

2651 GTTTTAGAG GTTGGTTGTT GTGTTTAGG ATTCTGTCCA TTTTCTTTTA

2701 AAGTTATAAA CACGTACTTG TGCGAATTAT TTTTTTAAAG TGATTTGCCA

2751 TTTTTGAAAG CGTATTTAAT GATAGAATAC TATCGAGCCA ACATGTACTG

2801 ACATGGAAAG ATGTCAAAGA TATGTTAAGT GTAAAATGCA AGTGGCAAAA

2851 CACTATGTAT AGTCTGAGCC AGATCAAAGT ATGTATGTTT TTAATATGCA

2901 TAGAACAAAA GATTTGGAAA GATATACACC AAACTGTTAA ATGTGGTTTC

2951 TCTTCGGGGA GGGGGGGATT GGGGGAGGGG CCCCATAGGG GTTTTATAGG

Fig. 15 (Page 3 of 3)

1 TTGCTCTGTC ACCCAGTTTG GAGTGCAGTT ATGCAGTCTC ACACTGCAAG

51 CTCTGCCTCA TGGGCTCAAG TGAACCTCCT GCCTCAGCCT CTCAAGTAGC

101 TGGGACCACA GGCAGGTGCC ACCATGTCTG GCTAATTTTT GAGTTTCTTT

151 GTAGAGATGG TGTTTTGCCA AGTCACCCAG TTTGAGGCTG GTCTCAAACA

201 CCTGGGCTCA AGCAATCCAT CTACCTCAGC CTCCCAAAGT GCTGGGATTA

251 CAGGAGTGAG CCATGGCATG AGGCCTTGTG GGGTGTCTCT TTTAAATGAA

301 AGCATACTCT GTTACGTAT TTGATATGAA GGAATATCCT TCCTTTCCAC

351 AAAGACAAAA ATTATCCTAT TTTTCTCAAA ACATATGTCC TTTTTCTCTA

401 CTTTTCATTT TTGTTACTTT TGATGGACAC ATGTGTTACA TTGATTTCAC

451 TTTCTCATAA TTCTGCTGTA AGAAAAACAA TAGTGCCAGT TCAATGACAA

501 ATAGCAACAG TCTGTTATTG CTAGACTGTT ACTGTTAGTG GAGACTACCA

551 GAACAGTCAG TCCCAGTGTC AGGGAATCAA AGAGAACATG TTCCCTCTCT

601 AAAGGGCACA GCTGCTGCTC AGCTTTAGCT GATTGCTGCC CTGCAGGACT

651 ATAGGCCCAG TGTTGCTAGA TCTTTTGATG TTTCAAGAGA AGCTTGGAAT

701 CTAGAATGTG ATGGGAAGTC TCTTACATTT AAACATGTTG GCAATTAATG

Fig. 16 (Page 1 of 9)

751 GTAAGATTTA AAAATACTGT GGTCCAAGAA AAAAATGGAT TTGGAAACTG

801 GATTAAATTC AAATGAGGCA TGCAGATTAA TCTACAGCAT GGTACAATGT

851 GAATTTTCTG GTTTCTTTAA TTGCACTGTA ATTAGGTAAG ATGTTAGCTT

901 TGGGGAAGCT AAGTGCAGAG TATGCAGAAA CTATTATTTT TGTAAGTTTT

951 CTCTAAGTAT AAATAAATTT CAAAATAAAA ATAAAAACTT AGTAAAGAAC

1001 TATAATGCAA TTCTATGTAA GCCAAACATA ATATGTCTTC CAGTTTGAAA

1051 CCTCTGGGTT TTATTTTATT TTATTTTATT TTTGAGACAG AGTCTTGCTG

1101 TGTCACCCAG GCTGGAGTGT AGTGGCACTA TTTCGGCCCA CTGCAACCTC

1151 CACCTCCCAG GCTCAAATGA TTCTCCTGCC TCAGCCTCCG GAGTAGCTGG

1201 GATTACAGGC GCGTACCACC ACACCCAGCT AATTTTTGTA TTTTTAGTAG

1251 AGATGGGGTT TCACCATTTT GGCCAGGCTG GTTTTGAACT CCTGACCTCA

1301 AGTGATCCAC TTGTCTTGGC CTCCCAAAAT GCTGGGATTA CAGGCGTGAG

1351 CCACTGCACC AGGCAGAGGC CTCTGTTTTT TATCTCTTTT TGGCCTCTAC

1401 AGTGCCTAGT AAAGCACCTG ATACATGGTA AACGATCAGT AATTACTAGT

1451 ACTCTATTTT GGAGAAAATG ATTTTTTAAA AAGTCATTGT GTTCCATCCA

Fig. 16 (Page 2 of 9)

1501 TGAGTCGTTT GAGTTTTAAA ACTGTCTTTT TGTTTGTTTT
TGAACAGGTT

1551 TACAAAGGAG GAAAACGACT TCTTCTAGAT TTTTTTTTCA
GTTTCTTCTA

1601 TAAATCAAAA CATCTCAAAA TGGAGACCTA AAATCCTTAA
AGGGACTTAG

1651 TCTAATCTCG GGAGGTAGTT TTGTGCATGG GTAAACAAAT
TAAGTATTAA

1701 CTGGTGTTTT ACTATCCAAA GAATGCTAAT TTTATAAACA
TGATCGAGTT

1751 ATATAAGGTA TACCATAATG AGTTTGATTT TGAATTTGAT
TTGTGGAAAT

1801 AAAGGAAAAG TGATTCTAGC TGGGGCATAT TGTTAAAGCA
TTTTTTTCAG

1851 AGTTGGCCAG GCAGTCTCCT ACTGGCACAT TCTCCCATTA
TGTAGAATAG

1901 AAATAGTACC TGTGTTTGGG AAAGATTTTA AAATGAGTGA
CAGTTATTTG

1951 GAACAAAGAG CTAATAATCA ATCCACTGCA AATTAAAGAA
ACATGCAGAT

2001 GAAAGTTTTG ACACATTAAA ATACTTCTAC AGTGACAAAG
AAAAATCAAG

2051 AACAAAGCTT TTTGATATGT GCAACAAATT TAGAGGAAGT
AAAAAGATAA

2101 ATGTGATGAT TGGTCAAGAA ATTATCCAGT TATTTACAAG
GCCACTGATA

2151 TTTTAAACGT CCAAAAGTTT GTTTAAATGG GCTGTTACCG
CTGAGAATGA

2201 TGAGGATGAG AATGATGGTT GAAGGTTACA TTTTAGGAAA
TGAAGAAACT

2251 TAGAAAATTA ATATAAAGAC AGTGATGAAT ACAAAGAAGA

Fig. 16 (Page 3 of 9)

TTTTTATAAC

2301 AATGTGTAAA ATTTTTGGCC AGGGAAAGGA ATATTGAAGT TAGATACAAT

2351 TACTTACCTT TGAGGGAAAT AATTGTTGGT AATGAGATGT GATGTTTCTC

2401 CTGCCACCTG GAAACAAAGC ATTGAAGTCT GCAGTTGAAA AGCCCAACGT

2451 CTGTGAGATC CAGGAAACCA TGCTTGCAAA CCACTGGTAA AAAAAAAAA

2501 AAAAAAAAAA AAAGCCACAG TGACTTGCTT ATTGGTCATT GCTAGTATTA

2551 TCGACTCAGA ACCTCTTTAC TAATGGCTAG TAAATCATAA TTGAGAAATT

2601 CTGAATTTTG ACAAGGTCTC TGCTGTTGAA ATGGTAAATT TATTATTTTT

2651 TTTGTCATGA TAAATTCTGG TTCAAGGTAT GCTATCCATG AAATAATTTC

2701 TGACCAAAAC TAAATTGATG CAATTTGATT ATCCATCTTA GCCTACAGAT

2751 GGCATCTGGT AACTTTTGAC TGTTTTAAAA AATAAATCCA CTATCAGAGT

2801 AGATTTGATG TTGGCTTCAG AAACATTTAG AAAAACAAAA GTTCAAAAAT

2851 GTTTTCAGGA GGTGATAAGT TGAATAACTC TACAATGTTA GTTCTTTGAG

2901 GGGGACAAAA AATTTAAAAT CTTTGAAAGG TCTTATTTTA CAGCCATATC

2951 TAAATTATCT TAAGAAAATT TTTAACAAAG GGAATGAAAT ATATATCATG

3001 ATTCTGTTTT TCCAAAAGTA ACCTGAATAT AGCAATGAAG TTCAGTTTTG

Fig. 16 (Page 4 of 9)

3051 TTATTGGTAG TTTGGGCAGA GTCTCTTTTT GCAGCACCTG
TTGTCTACCA

3101 TAATTACAGA GGACATTTCC ATGTTCTAGC CAAGTATACT
ATTAGAATAA

3151 AAAAACTTAA CATTGAGTTG CTTCAACAGC ATGAAACTGA
GTCCAAAAGA

3201 CCAAATGAAC AAACACATTA ATCTCTGATT ATTTATTTTA
AATAGAATAT

3251 TTAATTGTGT AAGATCTAAT AGTATCATTA TACTTAAGCA
ATCATATTCC

3301 TGATGATCTA TGGGAAATAA CTATTATTTA ATTAATATTG
AAACCAGGTT

3351 TTAAGATGTG TTAGCCAGTC CTGTTACTAG TAAATCTCTT
TATTTGGAGA

3401 GAAATTTTAG ATTGTTTTGT CTCCTTATT AGAAGGATTG
TAGAAAGAAA

3451 AAAATGACTA ATTGGAGAAA AATTGGGGAT ATATCATATT
TCACTGAATT

3501 CAAAATGTCT TCAGTTGTAA ATCTTACCAT TATTTTACGT
ACCTCTAAGA

3551 AATAAAGTG CTTCTAATTA AAATATGATG TCATTAATTA
TGAAATACTT

3601 CTTGATAACA GAAGTTTTAA AATAGCCATC TTAGAATCAG
TGAAATATGG

3651 TAATGTATTA TTTTCCTCCT TTGAGTNAGG TCTTGTGCTT
TTTNTTCCTG

3701 GCCACTAAAT NTCACCATNT CCAANAAGCA AANTAAACCT
ATTCTGAATA

3751 TTTTTGCTGT GAAACACTTG NCAGCAGAGC TTTCCCNCCA
TGNNAGAAGC

Fig. 16 (Page 5 of 9)

3801 TTCATGAGTC ACACATTACA TCTTTGGGTT GATTGAATGC CACTGAAACA

3851 TTTCTAGTAG CCTGGAGNAG TTGACCTACC TGTGGAGATG CCTGCCATTA

3901 AATGGCATCC TGATGGCTTA ATACACATCA CTCTTCTGTG NAGGGTTTTA

3951 ATTTTCAACA CAGCTTACTC TGTAGCATCA TGTTTACATT GTATGTATAA

4001 AGATTATACN AAGGTGCAAT TGTGTATTTC TTCCTTAAAA TGTATCAGTA

4051 TAGGATTTAG AATCTCCATG TTGAAACTCT AAATGCATAG AAATAAAAAT

4101 AATAAAAAAT TTTTCATTTT GGCTTTTCAG CCTAGTATTA AAACTGATAA

4151 AAGCAAAGCC ATGCACAAAA CTACCTCCCT AGAGAAAGGC TAGTCCCTTT

4201 TCTTCCCCAT TCATTTCATT ATGAACATAG TAGAAAACAG CATATTCTTA

4251 TCAAATTTGA TGAAAAGCGC CAACACGTTT GAACTGAAAT ACGACTTGTC

4301 ATGTGAACTG TACCGAATGT CTACGTATTC CACTTTTCCT GCTGGGGTTC

4351 CTGTCTCAGA AAGGAGTCTT GCTCGTGCTG GTTTCTATTA CACTGGTGTG

4401 AATGACAAGG TCAAATGCTT CTGTTGTGGC CTGATGCTGG ATAACTGGAA

4451 AAGAGGAGAC AGTCCTACTG AAAAGCATAA AAAGTTGTAT CCTAGCTGCA

4501 GATTCGTTCA GAGTCTAAAT TCCGTTAACA ACTTGGAAGC TACCTCTCAG

4551 CCTACTTTTC CTTCTTCAGT AACACATTCC ACACACTCAT

Fig. 16 (Page 6 of 9)

TACTTCCGGG

4601 TACAGAAAAC AGTGGATATT CCGTGGCTC TTATTCAAAC TCTCCATCAA

4651 ATCCTGTAAA CTCCAGAGCA AATCAAGAAT TTTCTGCCTT GATGAGAAGT

4701 TCCTACCCCT GTCCAATGAA TAACGAAAAT GCCAGATTAC TTACTTTTCA

4751 GACATGGCCA TTGACTTTTC TGTCGCCAAC AGATCTGGCA CGAGCAGGCT

4801 TTTACTACAT AGGACCTGGA GACAGAGTGG CTTGCTTTGC CTGTGGTGGA

4851 AAATTGAGCA ATTGGGAACC GAAGGATAAT GCTATGTCAG AACACCTGAG

4901 ACATTTTCCC AAATGCCCAT TTATAGAAAA TCAGCTTCAA GACACTTCAA

4951 GATACACAGT TTCTAATCTG AGCATGCAGA CACATGCAGC CCGCTTTAAA

5001 ACATTCTTTA ACTGGCCCTC TAGTGTTCTA GTTAATCCTG AGCAGCTTGC

5051 AAGTGCGGGT TTTTATTATG TGGGTAACAG TGATGATGTC AAATGCTTTT

5101 GCTGTGATGG TGGACTCAGG TGTTGGGAAT CTGGAGATGA TCCATGGGTT

5151 CAACATGCCA AGTGGTTTCC AAGGTGTGAG TACTTGATAA GAATTAAAGG

5201 ACAGGAGTTC ATCCGTCAAG TTCAAGCCAG TTACCCTCAT CTACTTGAAC

5251 AGCTGCTATC CACATCAGAC AGCCCAGGAG ATGAAAATGC AGAGTCATCA

5301 ATTATCCATT TGAACCTGG AGAAGACCAT TCAGAAGATG CAATCATGAT

Fig. 16 (Page 7 of 9)

5351 GAATACTCCT GTGATTAATG CTGCCGTGGA AATGGGCTTT AGTAGAAGCC

5401 TGGTAAAACA GACAGTTCAG AGAAAAATCC TAGCAACTGG AGAGAATTAT

5451 AGACTAGTCA ATGATCTTGT GTTAGACTTA CTCAATGCAG AAGATGAAAT

5501 AAGGGAAGAG GAGAGAGAAA GAGCAACTGA GGAAAAAGAA TCAAATGATT

5551 TATTATTAAT CCGGAAGAAT AGAATGGCAC TTTTTCAACA TTTGACTTGT

5601 GTAATTCCAA TCCTGGATAG TCTACTAACT GCCGGAATTA TTAATGAACA

5651 AGAACATGAT GTTATTAAAC AGAAGACACA GACGTCTTTA CAAGCAAGAG

5701 AACTGATTGA TACGATTTTA GTAAAAGGAA ATATTGCAGC CACTGTATTC

5751 AGAAACTCTC TGCAAGAAGC TGAAGCTGTG TTATATGAGC ATTTATTTGT

5801 GCAACAGGAC ATAAAATATA TTCCCACAGA AGATGTTTCA GATCTACCAG

5851 TGGAAGAACA ATTGCGGAGA CTACAAGAAG AAAGAACATG TAAAGTGTGT

5901 ATGGACAAAG AAGTGTCCAT AGTGTTTATT CCTTGTGGTC ATCTAGTAGT

5951 ATGCAAAGAT TGTGCTCCTT CTTTAAGAAA GTGTCCTATT TGTAGGAGTA

6001 CAATCAAGGG TACAGTTCGT ACATTCTTT CATGAAGAAG AACCAAAACA

6051 TCGTCTAAAC TTTAGAATTA ATTTATTAAA TGTATTATAA CTTTAACTTT

Fig. 16 (Page 8 of 9)

6101 TATCCTAATT TGGTTTCCTT AAAATTTTTA TTTATTTACA ACTCAAAAAA

6151 CATTGTTTTG TGTAACATAT TTATATATGT ATCTAAACCA TATGAACATA

6201 TATTTTTTAG AAACTAAGAG AATGATAGGC TTTTGTTCTT ATGAACGAAA

6251 AAGAGGTAGC ACTACAAACA CAATATTCAA TCAAAATTTC AGCATTATTG

6301 AAATTGTAAG TGAAGTAAAA CTTAAGATAT TTGAGTTAAC CTTTAAGAAT

6351 TTTAAATATT TTGGCATTGT ACTAATACCG GAACATGAA GCCAGGTGTG

6401 GTGGTATGTG CCTGTAGTCC CAGGCTGAGG CAAGAGAATT ACTTGAGCCC

6451 AGGAGTTTGA ATCCATCCTG GCAGCATAC TGAGACCCTG CCTTTAAAAA

6501 CAAACAGAAC AAAAACAAAA CACCAGGGAC ACATTTCTCT GTCTTTTTG

6551 ATCAGTGTCC TATACATCGA AGGTGTGCAT ATATGTTGAA TCACATTTTA

6601 GGGACATGGT GTTTTTATAA AGAATTCTGT GAGAAAAAAT TTAATAAAGC

6651 AACCAAAAAA AAAAAAAAA

Fig. 16 (Page 9 of 9)

SEQUENCE LISTING

<160> NUMBER OF SEQ ID NOS: 231

<210> SEQ ID NO 1
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 1
aaaattctaa gtacctgca                                                    19

<210> SEQ ID NO 2
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 2
tctagagggt ggctcagga                                                    19

<210> SEQ ID NO 3

```
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 3
cagatatata tgtaacact                                                       19

<210> SEQ ID NO 4
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 4
tgagagccct tttttttgtt                                                      19

<210> SEQ ID NO 5
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 5
agtatgaaat atttctgat                                                       19

<210> SEQ ID NO 6
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 6
attggttcca atgtgttct                                                       19

<210> SEQ ID NO 7
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 7
ttagcaaaat atgttttaa                                                       19

<210> SEQ ID NO 8
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 8
tgaattaatt tttaatatc                                                       19

<210> SEQ ID NO 9
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 9
```
attcaaggca tcaaagttg                                                19

<210> SEQ ID NO 10
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 10
gtcaaatcat taattagga                                                19

<210> SEQ ID NO 11
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 11
aatatgtaaa ctgtgatgc                                                19

<210> SEQ ID NO 12
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 12
gcagaataaa actaataat                                                19

<210> SEQ ID NO 13
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 13
gaaagtaata tttaagcag                                                19

<210> SEQ ID NO 14
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 14
ttaccacatc attcaagtc                                                19

<210> SEQ ID NO 15
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 15
ctaaatacta gagttcgac                                                19

<210> SEQ ID NO 16
<211> LENGTH: 19
<212> TYPE: DNA

```
<213> ORGANISM: Artificial Sequence
<220> FEATURE:
<223> OTHER INFORMATION: based on Homo sapiens

<400> SEQUENCE: 16
acacgaccgc taagaaaca                                                    19

<210> SEQ ID NO 17
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 17
tatccactta tgacataaa                                                    19

<210> SEQ ID NO 18
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 18
gttataggag ctaacaaat                                                    19

<210> SEQ ID NO 19
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 19
aatgtgaaac acaagcaac                                                    19

<210> SEQ ID NO 20
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 20
acattatatt aggaaatcc                                                    19

<210> SEQ ID NO 21
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 21
cttgtccacc ttttctaaa                                                    19

<210> SEQ ID NO 22
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 22
atcttctctt gaaaatagg                                                    19
```

<210> SEQ ID NO 23
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 23
ccttcaaaac tgttaaaag                                              19

<210> SEQ ID NO 24
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 24
atgtctgcag gtacacaag                                              19

<210> SEQ ID NO 25
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 25
atctattaaa ctcttctac                                              19

<210> SEQ ID NO 26
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 26
acaggactac cacttggaa                                              19

<210> SEQ ID NO 27
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 27
tgccagtgtt gatgctgaa                                              19

<210> SEQ ID NO 28
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 28
gtataaagaa accctgctc                                              19

<210> SEQ ID NO 29
<211> LENGTH: 19
<212> TYPE: DNA
<213> ORGANISM: Artificial Sequence
<220> FEATURE:

```
<223> OTHER INFORMATION: based on Homo sapiens

<400> SEQUENCE: 29
cgcacggtat ctccttcac                                                    19

<210> SEQ ID NO 30
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 30
ctacagctgc atgacaact                                                    19

<210> SEQ ID NO 31
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 31
gctgagtctc catattgcc                                                    19

<210> SEQ ID NO 32
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 32
atactttcct gtgtcttcc                                                    19

<210> SEQ ID NO 33
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 33
gataaatctg caatttggg                                                    19

<210> SEQ ID NO 34
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 34
ttgtagactg cgtggcact                                                    19

<210> SEQ ID NO 35
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 35
accattctgg ataccagaa                                                    19
```

<210> SEQ ID NO 36
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 36
agttttcaac tttgtactg                                            19

<210> SEQ ID NO 37
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 37
atgatctctg cttcccaga                                            19

<210> SEQ ID NO 38
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 38
agatggcctg tctaaggca                                            19

<210> SEQ ID NO 39
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 39
agttctcaaa agatagtct                                            19

<210> SEQ ID NO 40
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 40
gtgtctgata tatctacaa                                            19

<210> SEQ ID NO 41
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 41
tcgggtatat ggtgtctga                                            19

<210> SEQ ID NO 42
<211> LENGTH: 19
<212> TYPE: DNA
<213> ORGANISM: Artificial Sequence
<220> FEATURE:
<223> OTHER INFORMATION: based on Homo sapiens -continued

```
<400> SEQUENCE: 42
cagggttcct cgggtatat                                                    19

<210> SEQ ID NO 43
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 43
gcttcttcac aatacatgg                                                    19

<210> SEQ ID NO 44
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 44
ggccagttct gaaaggact                                                    19

<210> SEQ ID NO 45
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 45
gctaactctc ttggggtta                                                    19

<210> SEQ ID NO 46
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 46
gtgtagtaga gtccagcac                                                    19

<210> SEQ ID NO 47
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 47
aagcactgca cttggtcac                                                    19

<210> SEQ ID NO 48
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 48
ttcagttttc caccacaac                                                    19

<210> SEQ ID NO 49
<211> LENGTH: 19
```

```
<212> TYPE: DNA
<213> ORGANISM: Artificial Sequence
<220> FEATURE:
<223> OTHER INFORMATION: based on Homo sapiens

<400> SEQUENCE: 49
acgatcacaa ggttcccaa                                                    19

<210> SEQ ID NO 50
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 50
tcgcctgtgt tctgaccag                                                    19

<210> SEQ ID NO 51
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 51
ccggcccaaa acaaagaag                                                    19

<210> SEQ ID NO 52
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 52
gattcacttc gaatattaa                                                    19

<210> SEQ ID NO 53
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 53
tatcagaact cacagcatc                                                    19

<210> SEQ ID NO 54
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 54
ggaagatttg ttgaatttg                                                    19

<210> SEQ ID NO 55
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 55
```

```
tctgccatgg atggatttc                                              19

<210> SEQ ID NO 56
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 56
aagtaaagat ccgtgcttc                                              19

<210> SEQ ID NO 57
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 57
ctgagtatat ccatgtccc                                              19

<210> SEQ ID NO 58
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 58
gcaagctgct ccttgttaa                                              19

<210> SEQ ID NO 59
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 59
aaagcataaa atccagctc                                              19

<210> SEQ ID NO 60
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 60
gaaagcactt tactttatc                                              19

<210> SEQ ID NO 61
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 61
actgggcttc caatcagtt                                              19

<210> SEQ ID NO 62
<211> LENGTH: 19
<212> TYPE: DNA
<213> ORGANISM: Artificial Sequence
```

```
<220> FEATURE:
<223> OTHER INFORMATION: based on Homo sapiens

<400> SEQUENCE: 62
gttgttccca agggtcttc                                              19

<210> SEQ ID NO 63
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 63
accctggata ccatttagc                                              19

<210> SEQ ID NO 64
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 64
tgttctaaca gatatttgc                                              19

<210> SEQ ID NO 65
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 65
tatatattct tgtcccttc                                              19

<210> SEQ ID NO 66
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 66
agttaaatga atattgttt                                              19

<210> SEQ ID NO 67
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 67
gacactcctc aagtgaatg                                              19

<210> SEQ ID NO 68
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 68
tttctcagta gttccttacc                                             19
```

<210> SEQ ID NO 69
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 69
gttagtgatg gtgttttct                                              19

<210> SEQ ID NO 70
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 70
agatggtatc atcaattct                                              19

<210> SEQ ID NO 71
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 71
tgtaccatag gattttgga                                              19

<210> SEQ ID NO 72
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 72
ccccattcgt atagcttct                                              19

<210> SEQ ID NO 73
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 73
attattttct taatgtcct                                              19

<210> SEQ ID NO 74
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 74
caagtgattt atagttgct                                              19

<210> SEQ ID NO 75
<211> LENGTH: 19
<212> TYPE: DNA
<213> ORGANISM: Artificial Sequence
<220> FEATURE:
<223> OTHER INFORMATION: based on Homo sapiens

```
<400> SEQUENCE: 75
tagatctgca accagaacc                                                    19

<210> SEQ ID NO 76
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 76
catcttgcat actgtcttt                                                    19

<210> SEQ ID NO 77
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 77
ccttagctgc tcttcagta                                                    19

<210> SEQ ID NO 78
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 78
aagcttctcc tcttgcagg                                                    19

<210> SEQ ID NO 79
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 79
atatttctat ccatacaga                                                    19

<210> SEQ ID NO 80
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 80
ctagatgtcc acaaggaac                                                    19

<210> SEQ ID NO 81
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 81
agcacattgt ttacaagtg                                                    19

<210> SEQ ID NO 82
```

```
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 82
agcacatggg acacttgtc                                              19

<210> SEQ ID NO 83
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 83
cttgaaagta atgactgtg                                              19

<210> SEQ ID NO 84
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 84
cctactatag agttagatt                                              19

<210> SEQ ID NO 85
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 85
attcaatcag ggtaataag                                              19

<210> SEQ ID NO 86
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 86
aagtcagttc acatcacac                                              19

<210> SEQ ID NO 87
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 87
cagtaaaaaa aatggataa                                              19

<210> SEQ ID NO 88
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 88
```

```
ttcagttata gtatgatgc                                              19

<210> SEQ ID NO 89
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 89
tacacttaga aattaaatc                                              19

<210> SEQ ID NO 90
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 90
tctctatctt tccaccagc                                              19

<210> SEQ ID NO 91
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 91
agaatcctaa aacacaaca                                              19

<210> SEQ ID NO 92
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 92
attcgcacaa gtacgtgtt                                              19

<210> SEQ ID NO 93
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 93
tgtcagtaca tgttggctc                                              19

<210> SEQ ID NO 94
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 94
acatagtgtt ttgccactt                                              19

<210> SEQ ID NO 95
<211> LENGTH: 19
<212> TYPE: DNA
```

<213> ORGANISM: Artificial Sequence
<220> FEATURE:
<223> OTHER INFORMATION: based on Homo sapiens

<400> SEQUENCE: 95
ctttgatctg gctcagact                                                    19

<210> SEQ ID NO 96
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 96
gaaaccacat ttaacagtt                                                    19

<210> SEQ ID NO 97
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 97
tcatttgagc ctgggaggu                                                    19

<210> SEQ ID NO 98
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 98
cggaggctga ggcaggaga                                                    19

<210> SEQ ID NO 99
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 99
ggtgtggtgg tacgcgcct                                                    19

<210> SEQ ID NO 100
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 100
acccatgcac aaaactacc                                                    19

<210> SEQ ID NO 101
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 101
agaatgtgcc agtaggaga                                                    19

<210> SEQ ID NO 102
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 102
tctcacagac gttgggctt                                              19

<210> SEQ ID NO 103
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 103
ccagtggttt gcaagcatg                                              19

<210> SEQ ID NO 104
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 104
gaaatttagt ggccaggaa                                              19

<210> SEQ ID NO 105
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 105
agaaatacac aattgcacc                                              19

<210> SEQ ID NO 106
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 106
tactgataca ttttaagga                                              19

<210> SEQ ID NO 107
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 107
ttcaacatgg agattctaa                                              19

<210> SEQ ID NO 108
<211> LENGTH: 19
<212> TYPE: DNA
<213> ORGANISM: Artificial Sequence
<220> FEATURE:

<223> OTHER INFORMATION: based on Homo sapiens

<400> SEQUENCE: 108
atttctatgc atttagagt                                               19

<210> SEQ ID NO 109
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 109
aatactaggc tgaaaagcc                                               19

<210> SEQ ID NO 110
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 110
ggctttgctt ttatcagtt                                               19

<210> SEQ ID NO 111
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 111
tctagggagg tagttttgt                                               19

<210> SEQ ID NO 112
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 112
gggaagaaaa gggactagc                                               19

<210> SEQ ID NO 113
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 113
gttcataatg aaatgaatg                                               19

<210> SEQ ID NO 114
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 114
ataagaatat gctgttttc                                               19

<210> SEQ ID NO 115
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 115
ttcaaacgtg ttggcgctt                                                    19

<210> SEQ ID NO 116
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 116
atgacaagtc gtatttcag                                                    19

<210> SEQ ID NO 117
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 117
aagtggaata cgtagacat                                                    19

<210> SEQ ID NO 118
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 118
agacaggaac cccagcagg                                                    19

<210> SEQ ID NO 119
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 119
cgagcaagac tcctttctg                                                    19

<210> SEQ ID NO 120
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 120
agtgtaatag aaaccagca                                                    19

<210> SEQ ID NO 121
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 121
tgaccttgtc attcacacc                                            19

<210> SEQ ID NO 122
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 122
ttatccagca tcaggccac                                            19

<210> SEQ ID NO 123
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 123
actgtctcct cttttccag                                            19

<210> SEQ ID NO 124
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 124
ttttatgctt ttcagtagg                                            19

<210> SEQ ID NO 125
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 125
acgaatctgc agctaggat                                            19

<210> SEQ ID NO 126
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 126
caagttgtta acggaattt                                            19

<210> SEQ ID NO 127
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 127
taggctgaga ggtagcttc                                            19

<210> SEQ ID NO 128
<211> LENGTH: 19

```
<212> TYPE: DNA
<213> ORGANISM: Artificial Sequence
<220> FEATURE:
<223> OTHER INFORMATION: based on Homo sapiens

<400> SEQUENCE: 128
gttactgaag aaggaaaag                                                  19

<210> SEQ ID NO 129
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 129
gaatgagtgt gtggaatgt                                                  19

<210> SEQ ID NO 130
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 130
tgttttctgt acccggaag                                                  19

<210> SEQ ID NO 131
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 131
gagccacgga aatatccac                                                  19

<210> SEQ ID NO 132
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 132
tgatggagag tttgaataa                                                  19

<210> SEQ ID NO 133
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 133
gatttgctct ggagtttac                                                  19

<210> SEQ ID NO 134
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 134
```

-continued ggcagaaaat tcttgattt                              19

<210> SEQ ID NO 135
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 135
ggacaggggt aggaacttc                              19

<210> SEQ ID NO 136
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 136
gcattttcgt tattcattg                              19

<210> SEQ ID NO 137
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 137
ctgaaaagta agtaatctg                              19

<210> SEQ ID NO 138
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 138
ggcgacagaa aagtcaatg                              19

<210> SEQ ID NO 139
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 139
ccactctgtc tccaggtcc                              19

<210> SEQ ID NO 140
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 140
ccaccacagg caaagcaag                              19

<210> SEQ ID NO 141
<211> LENGTH: 19
<212> TYPE: DNA
<213> ORGANISM: Artificial Sequence

```
<220> FEATURE:
<223> OTHER INFORMATION: based on Homo sapiens

<400> SEQUENCE: 141
ttcggttccc aattgctca                                                19

<210> SEQ ID NO 142
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 142
ttctgacata gcattatcc                                                19

<210> SEQ ID NO 143
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 143
tgggaaaatg tctcaggtg                                                19

<210> SEQ ID NO 144
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 144
tataaatggg catttggga                                                19

<210> SEQ ID NO 145
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 145
tgtcttgaag ctgattttc                                                19

<210> SEQ ID NO 146
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 146
gaaactgtgt atcttgaag                                                19

<210> SEQ ID NO 147
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 147
tgtctgcatg ctcagatta                                                19
```

```
<210> SEQ ID NO 148
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 148
gaatgtttta aagcgggct                                              19

<210> SEQ ID NO 149
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 149
cactagaggg ccagttaaa                                              19

<210> SEQ ID NO 150
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 150
ccgcacttgc aagctgctc                                              19

<210> SEQ ID NO 151
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 151
catcatcact gttacccac                                              19

<210> SEQ ID NO 152
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 152
ccaccatcac agcaaaagc                                              19

<210> SEQ ID NO 153
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 153
tccagattcc caacacctg                                              19

<210> SEQ ID NO 154
<211> LENGTH: 19
<212> TYPE: DNA
<213> ORGANISM: Artificial Sequence
<220> FEATURE:
<223> OTHER INFORMATION: based on Homo sapiens
```

```
<400> SEQUENCE: 154
cccatggatc atctccaga                                               19

<210> SEQ ID NO 155
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 155
aaccacttgg catgttgaa                                               19

<210> SEQ ID NO 156
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 156
caagtactca caccttgga                                               19

<210> SEQ ID NO 157
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 157
cctgtccttt aattcttat                                               19

<210> SEQ ID NO 158
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 158
tgaacttgac ggatgaact                                               19

<210> SEQ ID NO 159
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 159
tagatgaggg taactggct                                               19

<210> SEQ ID NO 160
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 160
tggatagcag ctgttcaag                                               19

<210> SEQ ID NO 161
```

```
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 161
cattttcatc tcctgggct                                              19

<210> SEQ ID NO 162
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 162
tggataattg atgactctg                                              19

<210> SEQ ID NO 163
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 163
gtcttctcca ggttcaaaa                                              19

<210> SEQ ID NO 164
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 164
tattcatcat gattgcatc                                              19

<210> SEQ ID NO 165
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 165
catttccacg gcagcatta                                              19

<210> SEQ ID NO 166
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 166
ccaggcttct actaaagcc                                              19

<210> SEQ ID NO 167
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 167
```

```
gctaggattt ttctctgaa                                          19

<210> SEQ ID NO 168
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 168
tctataattc tctccagtt                                          19

<210> SEQ ID NO 169
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 169
acacaagatc attgactag                                          19

<210> SEQ ID NO 170
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 170
tctgcattga gtaagtcta                                          19

<210> SEQ ID NO 171
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 171
ctcttccctt atttcatct                                          19

<210> SEQ ID NO 172
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 172
tcctcagttg ctctttctc                                          19

<210> SEQ ID NO 173
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 173
gccattctat tcttccgga                                          19

<210> SEQ ID NO 174
<211> LENGTH: 19
<212> TYPE: DNA
```

<213> ORGANISM: Artificial Sequence
<220> FEATURE:
<223> OTHER INFORMATION: based on Homo sapiens

<400> SEQUENCE: 174
agtcaaatgt tgaaaaagt                                                  19

<210> SEQ ID NO 175
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 175
ccaggattgg aattacaca                                                  19

<210> SEQ ID NO 176
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 176
attccggcag ttagtagac                                                  19

<210> SEQ ID NO 177
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 177
taacatcatg ttcttgttc                                                  19

<210> SEQ ID NO 178
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 178
gtctgtgtct tctgtttaa                                                  19

<210> SEQ ID NO 179
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 179
ttctcttgct tgtaaagac                                                  19

<210> SEQ ID NO 180
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 180
ctaaaatcgt atcaatcag                                                  19

<210> SEQ ID NO 181
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 181
ggctgcaata tttccttttt                                              19

<210> SEQ ID NO 182
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 182
gagagtttct gaatacagt                                               19

<210> SEQ ID NO 183
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 183
acagcttcag cttcttgca                                               19

<210> SEQ ID NO 184
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 184
aaataaatgc tcatataac                                               19

<210> SEQ ID NO 185
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 185
gaaacatctt ctgtgggaa                                               19

<210> SEQ ID NO 186
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 186
gttcttccac tggtagatc                                               19

<210> SEQ ID NO 187
<211> LENGTH: 19
<212> TYPE: DNA
<213> ORGANISM: Artificial Sequence
<220> FEATURE:

-continued

<223> OTHER INFORMATION: based on Homo sapiens

<400> SEQUENCE: 187
cttcttgtag tctccgcaa                                            19

<210> SEQ ID NO 188
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 188
ttgtccatac acactttac                                            19

<210> SEQ ID NO 189
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 189
aaccaaatta ggataaaag                                            19

<210> SEQ ID NO 190
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 190
atgttcatat ggtttagat                                            19

<210> SEQ ID NO 191
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 191
taagttttac ttcacttac                                            19

<210> SEQ ID NO 192
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 192
atgttcccgg tattagtac                                            19

<210> SEQ ID NO 193
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 193
gggctcaagt aattctctt                                            19

```
<210> SEQ ID NO 194
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 194
gcccaggatg gattcaaac                                                19

<210> SEQ ID NO 195
<211> LENGTH: 19
<212> TYPE: DNA
<213> ORGANISM: Artificial Sequence
<220> FEATURE:
<223> OTHER INFORMATION: based on Homo sapiens
<221> NAME/KEY: modified_base
<222> LOCATION: 1
<223> OTHER INFORMATION: y=gm
<221> NAME/KEY: modified_base
<222> LOCATION: 18
<223> OTHER INFORMATION: y=cm

<400> SEQUENCE: 195
yagaagatga ctggtaaya                                                19

<210> SEQ ID NO 196
<211> LENGTH: 18
<212> TYPE: DNA
<213> ORGANISM: Artificial Sequence
<220> FEATURE:
<223> OTHER INFORMATION: based on Homo sapiens
<221> NAME/KEY: misc_feature
<222> LOCATION: 1,17,18
<223> OTHER INFORMATION: y=u or t

<400> SEQUENCE: 196
ygtgctattc tgtgaayy                                                 18

<210> SEQ ID NO 197
<211> LENGTH: 20
<212> TYPE: DNA
<213> ORGANISM: Artificial Sequence
<220> FEATURE:
<223> OTHER INFORMATION: based on Homo sapiens

<400> SEQUENCE: 197
tctgcttcaa ggagctggaa                                               20

<210> SEQ ID NO 198
<211> LENGTH: 18
<212> TYPE: DNA
<213> ORGANISM: Artificial Sequence
<220> FEATURE:
<223> OTHER INFORMATION: based on Homo sapiens

<400> SEQUENCE: 198
gaaaggaaag cgcaaccg                                                 18

<210> SEQ ID NO 199
<211> LENGTH: 30
<212> TYPE: DNA
<213> ORGANISM: Artificial Sequence
<220> FEATURE:
<223> OTHER INFORMATION: based on Homo sapiens

<400> SEQUENCE: 199
agccagatga cgaccccata gaggaacata                                    30
```

<210> SEQ ID NO 200
<211> LENGTH: 21
<212> TYPE: DNA
<213> ORGANISM: Artificial Sequence
<220> FEATURE:
<223> OTHER INFORMATION: based on Homo sapiens

<400> SEQUENCE: 200
tggagatgat ccatgggttc a                                              21

<210> SEQ ID NO 201
<211> LENGTH: 29
<212> TYPE: DNA
<213> ORGANISM: Artificial Sequence
<220> FEATURE:
<223> OTHER INFORMATION: based on Homo sapiens

<400> SEQUENCE: 201
gaactcctgt cctttaattc ttatcaagt                                      29

<210> SEQ ID NO 202
<211> LENGTH: 27
<212> TYPE: DNA
<213> ORGANISM: Artificial Sequence
<220> FEATURE:
<223> OTHER INFORMATION: based on Homo sapiens

<400> SEQUENCE: 202
ctcacacctt ggaaaccact tggcatg                                        27

<210> SEQ ID NO 203
<211> LENGTH: 27
<212> TYPE: DNA
<213> ORGANISM: Artificial Sequence
<220> FEATURE:
<223> OTHER INFORMATION: based on Homo sapiens

<400> SEQUENCE: 203
ggtgataaag taaagtgctt tcactgt                                        27

<210> SEQ ID NO 204
<211> LENGTH: 28
<212> TYPE: DNA
<213> ORGANISM: Artificial Sequence
<220> FEATURE:
<223> OTHER INFORMATION: based on Homo sapiens

<400> SEQUENCE: 204
tcagtagttc ttaccagaca ctcctcaa                                       28

<210> SEQ ID NO 205
<211> LENGTH: 34
<212> TYPE: DNA
<213> ORGANISM: Artificial Sequence
<220> FEATURE:
<223> OTHER INFORMATION: based on Homo sapiens

<400> SEQUENCE: 205
caacatgcta aatggtatcc aggtgcaaa tatc                                 34

<210> SEQ ID NO 206
<211> LENGTH: 19
<212> TYPE: DNA
<213> ORGANISM: Artificial Sequence
<220> FEATURE:

```
<223> OTHER INFORMATION: based on Homo sapiens

<400> SEQUENCE: 206
gaaggtgaag gtcggagtc                                               19

<210> SEQ ID NO 207
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 207
gaagatggtg atgggattc                                               19

<210> SEQ ID NO 208
<211> LENGTH: 20
<212> TYPE: DNA
<213> ORGANISM: Artificial Sequence
<220> FEATURE:
<223> OTHER INFORMATION: based on Homo sapiens

<400> SEQUENCE: 208
caagcttccc gttctcagcc                                              20

<210> SEQ ID NO 209
<211> LENGTH: 19
<212> TYPE: DNA
<213> ORGANISM: Artificial Sequence
<220> FEATURE:
<221> NAME/KEY: modified_base
<222> LOCATION: 1,17
<223> OTHER INFORMATION: y= cm
<221> NAME/KEY: modified_base
<222> LOCATION: 3,18
<223> OTHER INFORMATION: y=gm
<221> NAME/KEY: modified_base
<222> LOCATION: 19
<223> OTHER INFORMATION: y=um
<223> OTHER INFORMATION: based on Homo sapiens

<400> SEQUENCE: 209
yayagatttc atttaayyy                                               19

<210> SEQ ID NO 210
<211> LENGTH: 19
<212> TYPE: DNA
<213> ORGANISM: Artificial Sequence
<220> FEATURE:
<221> NAME/KEY: modified_base
<222> LOCATION: 1,18
<223> OTHER INFORMATION: y=cm
<221> NAME/KEY: modified_base
<222> LOCATION: 2,17
<223> OTHER INFORMATION: y=um
<223> OTHER INFORMATION: based on Homo sapiens

<400> SEQUENCE: 210
yyacgctcgc catcgtyya                                               19

<210> SEQ ID NO 211
<211> LENGTH: 19
<212> TYPE: DNA
<213> ORGANISM: Artificial Sequence
<220> FEATURE:
<221> NAME/KEY: modified_base
<222> LOCATION: 3,18
<223> OTHER INFORMATION: y=cm
<221> NAME/KEY: modified_base
```

```
<222> LOCATION: 1,17
<223> OTHER INFORMATION: y=um
<221> NAME/KEY: modified_base
<222> LOCATION: 2,16
<223> OTHER INFORMATION: y=gm
<223> OTHER INFORMATION: based on Homo sapiens

<400> SEQUENCE: 211
yycccaagaa tactagyya                                              19

<210> SEQ ID NO 212
<211> LENGTH: 19
<212> TYPE: DNA
<213> ORGANISM: Artificial Sequence
<220> FEATURE:
<221> NAME/KEY: modified_base
<222> LOCATION: 1,17,18
<223> OTHER INFORMATION: y=um
<221> NAME/KEY: modified_base
<222> LOCATION: 19
<223> OTHER INFORMATION: y=cm
<223> OTHER INFORMATION: based on Homo sapiens

<400> SEQUENCE: 212
yaagctgttc tatgtgyyy                                              19

<210> SEQ ID NO 213
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 213
aagggcggcg gagtgagac                                              19

<210> SEQ ID NO 214
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 214
agaggacgga gtcggaggc                                              19

<210> SEQ ID NO 215
<211> LENGTH: 19
<212> TYPE: DNA
<213> ORGANISM: Artificial Sequence
<220> FEATURE:
<223> OTHER INFORMATION: based on Homo sapiens

<400> SEQUENCE: 215
cggagcgtga ggatggaga                                              19

<210> SEQ ID NO 216
<211> LENGTH: 68
<212> TYPE: PRT
<213> ORGANISM: Artificial Sequence
<220> FEATURE:
<223> OTHER INFORMATION: based on Homo sapiens
<221> NAME/KEY: VARIANT
<222> LOCATION: 1-3,6,9,10,14,15,18-20,24, 30,32,33,35,37,40, 42-47,
      49-51, 53-57, 59-62, 64,66
<223> OTHER INFORMATION: Xaa=any amino acid
<221> NAME/KEY: VARIANT
<222> LOCATION: 13, 16,17
<223> OTHER INFORMATION: Xaa=any amino acid or is absent
```

<400> SEQUENCE: 216

Xaa Xaa Xaa Arg Leu Xaa Thr Phe Xaa Xaa Trp Pro Xaa Xaa Xaa Xaa
 1               5                   10                  15

Xaa Xaa Xaa Xaa Xaa Leu Ala Xaa Ala Gly Phe Tyr Tyr Xaa Gly Xaa
            20                  25                  30

Xaa Asp Xaa Val Xaa Cys Phe Xaa Cys Xaa Xaa Xaa Xaa Xaa Xaa Trp
        35                  40                  45

Xaa Xaa Xaa Asp Xaa Xaa Xaa Xaa Xaa His Xaa Xaa Xaa Xaa Pro Xaa
        50                  55                  60

Cys Xaa Phe Val
65

<210> SEQ ID NO 217
<211> LENGTH: 46
<212> TYPE: PRT
<213> ORGANISM: Artificial Sequence
<220> FEATURE:
<223> OTHER INFORMATION: based on Homo sapiens
<221> NAME/KEY: VARIANT
<222> LOCATION: 2-7,9-11,17-21,23,25, 30-32,34-35, 38-42 ,45
<223> OTHER INFORMATION: Xaa=any amino acid
<221> NAME/KEY: VARIANT
<222> LOCATION: 8
<223> OTHER INFORMATION: Xaa=Glu or Asp
<221> NAME/KEY: VARIANT
<222> LOCATION: 14,22
<223> OTHER INFORMATION: Xaa=Val or Ile

<400> SEQUENCE: 217

Glu Xaa Xaa Xaa Xaa Xaa Xaa Xaa Xaa Xaa Cys Lys Xaa Cys Met
 1               5                   10                  15

Xaa Xaa Xaa Xaa Xaa Xaa Xaa Phe Xaa Pro Cys Gly His Xaa Xaa Xaa
            20                  25                  30

Cys Xaa Xaa Cys Ala Xaa Xaa Xaa Xaa Xaa Cys Pro Xaa Cys
        35                  40                  45

<210> SEQ ID NO 218
<211> LENGTH: 2540
<212> TYPE: DNA
<213> ORGANISM: Homo sapiens
<220> FEATURE:
<221> NAME/KEY: misc_feature
<222> LOCATION: (1)...(2540)
<223> OTHER INFORMATION: n=a,t,c, or g

<400> SEQUENCE: 218
gaaaaggtgg acaagtccta ttttcaagag aagatgactt ttaacagttt tgaaggatct      60
aaaacttgtg tacctgcaga catcaataag gaagaagaat ttgtagaaga gtttaataga     120
ttaaaaactt ttgctaattt tccaagtggt agtcctgttt cagcatcaac actggcacga     180
gcagggtttc tttatactgg tgaaggagat accgtgcggt gctttagttg tcatgcagct     240
gtagatagat ggcaatatgg agactcagca gttggaagac acaggaaagt atccccaaat     300
tgcagattta tcaacggctt ttatcttgaa aatagtgcca cgcagtctac aaattctggt     360
atccagaatg gtcagtacaa agttgaaaac tatctgggaa gcagagatca ttttgcctta     420
gacaggccat ctgagacaca tgcagactat cttttgagaa ctgggcaggt tgtagatata     480
tcagacacca tatcccgag gaaccctgcc atgtattgtg aagaagctag attaaagtcc     540
tttcagaact ggccagacta tgctcaccta accccaagag agttagcaag tgctggactc     600
tactacacag gtattggtga ccaagtgcag tgcttttgtt gtggtggaaa actgaaaaat     660

-continued

```
tgggaacctt gtgatcgtgc ctggtcagaa cacaggcgac actttcctaa ttgcttcttt      720
gttttgggcc ggaatcttaa tattcgaagt gaatctgatg ctgtgagttc tgataggaat      780
ttcccaaatt caacaaatct tccaagaaat ccatccatgg cagattatga agcacggatc      840 tttactttg gacatggat atactcagtt aacaaggagc agcttgcaag agctggattt        900
tatgctttag gtgaaggtga taaagtaaag tgctttcact gtggaggagg gctaactgat      960
tggaagccca gtgaagaccc ttgggaacaa catgctaaat ggtatccagg gtgcaaatat     1020
ctgttagaac agaagggaca agaatatata acaatattc atttaactca ttcacttgag     1080
gagtgtctgg taagaactac tgagaaaaca ccatcactaa ctagaagaat tgatgatacc     1140
atcttccaaa atcctatggt acaagaagct atacgaatgg ggttcagttt caaggacatt     1200
aagaaaataa tggaggaaaa aattcagata tctgggagca actataaatc acttgaggtt     1260
ctggttgcag atcagtgaa tgctcagaaa gacagtatgc aagatgagtc aagtcagact      1320
tcattacaga aagagattag tactgaagag cagctaaggc gcctgcaaga ggagaagctt     1380
tgcaaaatct gtatggatag aaatattgct atcgttttg ttccttgtgg acatctagtc      1440
acttgtaaac aatgtgctga agcagttgac aagtgtccca tgtgctacac agtcattact     1500
ttcaagcaaa aaatttttat gtcttaatct aactctatag taggcatgtt atgttgttct     1560
tattaccctg attgaatgtg tgatgtgaac tgacttttaag taatcaggat tgaattccat    1620
tagcatttgc taccaagtag gaaaaaaaat gtacatggca gtgttttagt tggcaatata    1680
atctttgaat ttcttgattt ttcagggtat tagctgtatt atccattttt tttactgtta     1740
tttaattgaa accatagact aagaataaga agcatcatac tataactgaa cacaatgtgt    1800
attcatagta tactgatta atttctaagt gtaagtgaat taatcatctg gatttttat      1860 tcttttcaga taggcttaac aaatggagct ttctgtatat aaatgtggag attagagtta    1920
atctccccaa tcacataatt tgttttgtgt gaaaaggaa taaattgttc catgctggtg     1980
gaaagataga gattgttttt agaggttggt tgttgtgttt taggattctg tccatttct    2040 tgtaaaggga taaacacgga cgtgtgcgaa atatgtttgt aaagtgattt gccattgttg    2100
aaagcgtatt taatgataga atactatcga gccaacatgt actgacatgg aaagatgtca    2160
gagatatgtt aagtgtaaaa tgcaagtggc gggacactat gtatagtctg agccagatca    2220
aagtatgtat gttgttaata tgcatagaac gagagatttg gaaagatata caccaaactg    2280
ttaaatgtgg tttctcttcg gggagggggg gattggggga ggggcccag aggggtttta     2340 gagggccctt ttcactttcg actttttttca ttttgttctg ttcggatttt ttataagtat   2400
gtagaccccg aagggtttta tgggaactaa catcagtaac ctaaccccg tgactatcct     2460 gtgctcttcc tagggagctg tgttgtttcc cacccaccac ccttccctct gaacaaatgc    2520
ctgagtgctg gggcactttn                                                 2540
```

<210> SEQ ID NO 219
<211> LENGTH: 497
<212> TYPE: PRT
<213> ORGANISM: Homo sapiens

<400> SEQUENCE: 219

Met Thr Phe Asn Ser Phe Glu Gly Ser Lys Thr Cys Val Pro Ala Asp
 1               5                  10                  15

Ile Asn Lys Glu Glu Glu Phe Val Glu Glu Phe Asn Arg Leu Lys Thr
            20                  25                  30

```
Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Gly Gly Lys Leu Lys
        195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
    370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Glu Lys
        435                 440                 445

Leu Cys Lys Ile Cys Met Asp Arg Asn Ile Ala Ile Val Phe Val Pro
```

|  |  |  | 450 |  |  |  | 455 |  |  |  | 460 |  |
|---|---|---|---|---|---|---|---|---|---|---|---|---|
| Cys | Gly | His | Leu | Val | Thr | Cys | Lys | Gln | Cys | Ala | Glu | Ala | Val | Asp | Lys |
| 465 |  |  |  | 470 |  |  |  | 475 |  |  |  | 480 |

| Cys | Pro | Met | Cys | Tyr | Thr | Val | Ile | Thr | Phe | Lys | Gln | Lys | Ile | Phe | Met |
|---|---|---|---|---|---|---|---|---|---|---|---|---|---|---|---|
|  |  |  |  | 485 |  |  |  | 490 |  |  |  | 495 |  |  |  |

Ser

<210> SEQ ID NO 220
<211> LENGTH: 2676
<212> TYPE: DNA
<213> ORGANISM: Homo sapiens
<220> FEATURE:
<221> NAME/KEY: misc_feature
<222> LOCATION: (1)...(2676)
<223> OTHER INFORMATION: n=a,t,c, or g

<400> SEQUENCE: 220

```
tccttgagat gtatcagtat aggatttagg atctccatgt tggaactcta aatgcataga      60
aatggaaata atggaaattt ttcattttgg cttttcagcc tagtattaaa actgataaaa     120
gcaaagccat gcacaaaact acctccctag agaaaggcta gtccctttc ttccccattc      180
atttcattat gaacatagta gaaaacagca tattcttatc aaatttgatg aaaagcgcca     240
acacgtttga actgaaatac gacttgtcat gtgaactgta ccgaatgtct acgtattcca     300
cttttcctgc tggggttcct gtctcagaaa ggagtcttgc tcgtgctggt ttctattaca     360
ctggtgtgaa tgacaaggtc aaatgcttct gttgtggcct gatgctggat aactggaaaa     420
gaggagacag tcctactgaa aagcataaaa agttgtatcc tagctgcaga ttcgttcaga     480
gtctaaattc cgttaacaac ttggaagcta cctctcagcc tactttcct tcttcagtaa      540
cacattccac acactcatta cttccgggta cagaaaacag tggatatttc cgtggctctt     600
attcaaactc tccatcaaat cctgtaaact ccagagcaaa tcaagaattt tctgccttga     660
tgagaagttc ctaccctgt ccaatgaata cgaaaatgc cagattactt acttttcaga      720
catggccatt gactttctg tcgccaacag atctggcacg agcaggcttt tactacatag      780
gacctggaga cagagtggct tgctttgcct gtggtggaaa attgagcaat gggaaccga     840
aggataatgc tatgtcagaa cacctgagac atttttcccaa atgcccattt atagaaaatc     900
agcttcaaga cacttcaaga tacacagttt ctaatctgag catgcagaca catgcagccc     960
gctttaaaac attctttaac tggccctcta gtgttctagt taatcctgag cagcttgcaa    1020
gtgcgggttt ttattatgtg ggtaacagtg atgatgtcaa atgcttttgc tgtgatggtg    1080
gactcaggtg ttgggaatct ggagatgatc catgggttca acatgccaag tggtttccaa    1140
ggtgtgagta cttgataaga attaaaggac aggagttcat ccgtcaagtt caagccagtt    1200
accctcatct acttgaacag ctgctatcca catcagacag cccaggagat gaaaatgcag    1260
agtcatcaat tatccatttg gaacctggag aagaccattc agaagatgca atcatgatga    1320
atactcctgt gattaatgct gccgtggaaa tgggctttag tagaagcctg gtaaaacaga    1380
cagttcagag aaaaatccta gcaactggag agaattatag actagtcaat gatcttgtgt    1440
tagacttact caatgcagaa gatgaaataa gggaagagga gagagaaaga gcaactgagg    1500
aaaaagaatc aaatgattta ttattaatcc ggaagaatag aatggcactt tttcaacatt    1560
tgacttgtgt aattccaatc ctggatagtc tactaactgc cggaattatt aatgaacaag    1620
aacatgatgt tattaaacag aagacacaga cgtctttaca agcaagagaa ctgattgata    1680
cgatttagt aaaaggaaat attgcagcca ctgtattcag aaactctctg caagaagctg    1740
```

```
aagctgtgtt atatgagcat ttatttgtgc aacaggacat aaaatatatt cccacagaag    1800
atgtttcaga tctaccagtg gaagaacaat tgcggagact accagaagaa agaacatgta    1860
aagtgtgtat ggacaaagaa gtgtccatag tgtttattcc ttgtggtcat ctagtagtat    1920
gcaaagattg tgctccttct ttaagaaagt gtcctatttg taggagtaca atcaagggta    1980
cagttcgtac atttctttca tgaagaagaa ccaaaacatc gtctaaactt tagaattaat    2040
ttattaaatg tattataact ttaacttttta tcctaatttg gtttccttaa aatttttatt    2100
tatttacaac tcaaaaaaca ttgttttgtg taacatattt atatatgtat ctaaaccata    2160
tgaacatata ttttttagaa actaagagaa tgataggctt ttgttcttat gaacgaaaaa    2220
gaggtagcac tacaaacaca atattcaatc caaatttcag cattattgaa attgtaagtg    2280
aagtaaaact taagatattt gagttaacct ttaagaattt taaatatttt ggcattgtac    2340
taataccggg aacatgaagc caggtgtggt ggtatgtacc tgtagtccca ggctgaggca    2400
agagaattac ttgagcccag gagtttgaat ccatcctggg cagcatactg agaccctgcc    2460
tttaaaaacn aacagnacca aanccaaaca ccagggacaa atttctctgt ctttttttgat    2520 cagtgtccta tacatcgaag gtgtgcatat atgttgaatc acatttttagg gacatggtgt    2580 ttttataaag aattctgtga gnaaaaattt aataaagcaa ccaaattact cttaaaaaaa    2640
aaaaaaaaaa aaaaaactcg agggccccgt accaat                              2676
```

<210> SEQ ID NO 221
<211> LENGTH: 604
<212> TYPE: PRT
<213> ORGANISM: Homo sapiens

<400> SEQUENCE: 221

```
Met Asn Ile Val Glu Asn Ser Ile Phe Leu Ser Asn Leu Met Lys Ser
 1               5                  10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr His Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Glu Phe Ser Ala Leu Met Arg Ser
145                 150                 155                 160

Ser Tyr Pro Cys Pro Met Asn Asn Glu Asn Ala Arg Leu Leu Thr Phe
                165                 170                 175

Gln Thr Trp Pro Leu Thr Phe Leu Ser Pro Thr Asp Leu Ala Arg Ala
            180                 185                 190

Gly Phe Tyr Tyr Ile Gly Pro Gly Asp Arg Val Ala Cys Phe Ala Cys
        195                 200                 205
```

Gly Gly Lys Leu Ser Asn Trp Glu Pro Lys Asp Asn Ala Met Ser Glu
            210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
                260                 265                 270

Pro Glu Gln Leu Ala Ser Ala Gly Phe Tyr Tyr Val Gly Asn Ser Asp
            275                 280                 285

Asp Val Lys Cys Phe Cys Cys Asp Gly Gly Leu Arg Cys Trp Glu Ser
            290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
                340                 345                 350

Gly Asp Glu Asn Ala Glu Ser Ser Ile Ile His Leu Glu Pro Gly Glu
            355                 360                 365

Asp His Ser Glu Asp Ala Ile Met Met Asn Thr Pro Val Ile Asn Ala
            370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
            435                 440                 445

Lys Asn Arg Met Ala Leu Phe Gln His Leu Thr Cys Val Ile Pro Ile
450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
            515                 520                 525

Gln Asp Ile Lys Tyr Ile Pro Thr Glu Asp Val Ser Asp Leu Pro Val
            530                 535                 540

Glu Glu Gln Leu Arg Arg Leu Pro Glu Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
            595                 600

<210> SEQ ID NO 222
<211> LENGTH: 2580

```
<212> TYPE: DNA
<213> ORGANISM: Homo sapiens
<220> FEATURE:
<221> NAME/KEY: misc_feature
<222> LOCATION: (1)...(2580)
<223> OTHER INFORMATION: n=a,t,c, or g

<400> SEQUENCE: 222
ttaggttacc tgaaagagtt actacaaccc caaagagttg tgttctaagt agtatcttgg      60
taattcagag agatactcat cctacctgaa tataaactga gataaatcca gtaaagaaag     120
tgtagtaaat tctacataag agtctatcat tgatttcttt ttgtggtgga aatcttagtt     180
catgtgaaga aatttcatgt gaatgtttta gctatcaaac agtactgtca cctactcatg     240
cacaaaactg cctcccaaag acttttccca ggtccctcgt atcaaaacat aagagtata      300
atggaagata gcacgatctt gtcagattgg acaaacagca acaaacaaaa atgaagtat      360
gacttttcct gtgaactcta cagaatgtct acatattcaa ctttccccgc cggggtgcct     420
gtctcagaaa ggagtcttgc tcgtgctggt ttttattata ctggtgtgaa tgacaaggtc     480
aaatgcttct gttgtggcct gatgctggat aactggaaac taggagacag tcctattcaa     540
aagcataaac agctatatcc tagctgtagc tttattcaga atctggtttc agctagtctg     600
ggatccacct ctaagaatac gtctccaatg agaaacagtt ttgcacattc attatctccc     660
accttggaac atagtagctt gttcagtggt tcttactcca gccttcctcc aaaccctctt     720
aattctagag cagttgaaga catctcttca tcgaggacta accctacag ttatgcaatg      780
agtactgaag aagccagatt tcttacctac catatgtggc cattaacttt tttgtcacca     840
tcagaattgg caagagctgg tttttattat ataggacctg gagatagggt agcctgcttt     900
gcctgtggtg ggaagctcag taactgggaa ccaaaggatg atgctatgtc agaacaccgg     960
aggcattttc ccaactgtcc attttggaa aattctctag aaactctgag gtttagcatt     1020
tcaaatctga gcatgcagac acatgcagct cgaatgagaa catttatgta ctggccatct     1080
agtgttccag ttcagcctga gcagcttgca agtgctggtt tttattatgt gggtcgcaat     1140
gatgatgtca aatgctttgg ttgtgatggt ggcttgaggt gttgggaatc tggagatgat     1200
ccatgggtag aacatgccaa gtggtttcca aggtgtgagt tcttgatacg aatgaaaggc     1260
caagagtttg ttgatgagat tcaaggtaga tatcctcatc ttcttgaaca gctgttgtca     1320
acttcagata ccactggaga agaaaatgct gacccaccaa ttattcattt tggacctgga     1380
gaaagttctt cagaagatgc tgtcatgatg aatacacctg tggttaaatc tgccttggaa     1440
atgggcttta atagagacct ggtgaaacaa acagttctaa gtaaaatcct gacaactgga     1500
gagaactata aaacagttaa tgatattgtg tcagcacttc ttaatgctga agatgaaaaa     1560
agagaagagg agaaggaaaa acaagctgaa gaaatggcat cagatgattt gtcattaatt     1620
cggaagaaca gaatggctct cttcaacaa ttgacatgtg tgcttcctat cctggataat      1680
cttttaaagg ccaatgtaat taataaacag gaacatgata ttattaaaca aaaaacacag     1740
ataccttac aagcgagaga actgattgat accatttggg ttaaaggaaa tgctgcggcc     1800
aacatcttca aaaactgtct aaaagaaatt gactctacat tgtataagaa cttatttgtg     1860
gataagaata tgaagtatat tccaacagaa gatgtttcag gtctgtcact ggaagaacaa     1920
ttgaggaggt tgcaagaaga acgaacttgt aaagtgtgta tggacaaaga agtttctgtt     1980
gtatttattc cttgtggtca tctggtagta tgccaggaat gtgcccttc tctaagaaaa      2040
tgccctattt gcaggggtat aatcaagggt actgttcgta catttctctc ttaaagaaaa     2100
```

-continued

```
atagtctata ttttaacctg catgaaaagg tctttaaaat attgttgaac acttgaagcc    2160
atctaaagta aaagggaat tatgagtttt tcaattagta acattcatgt tctagtctgc    2220
tttggtacta ataatcttgt ttctgaaaag atggtatcat atatttaatc ttaatctgtt    2280
tatttacaag ggaagattta tgtttggtga actatattag tatgtatgtg tacctaaggg    2340
agtagcgtcn ctgcttgtta tgcatcattt caggagttac tggatttgtt gttctttcag    2400
aaagctttga anactaaatt atagtgtaga aaagaactgg aaaccaggaa ctctggagtt    2460
catcagagtt atggtgccga attgtctttg gtgcttttca cttgtgtttt aaaataagga    2520
tttttctctt atttctcccc ctagtttgtg agaaacatct caataaagtg ctttaaaaag    2580
```

<210> SEQ ID NO 223
<211> LENGTH: 618
<212> TYPE: PRT
<213> ORGANISM: Homo sapiens

<400> SEQUENCE: 223

```
Met His Lys Thr Ala Ser Gln Arg Leu Phe Pro Gly Pro Ser Tyr Gln
 1               5                  10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Pro Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
        195                 200                 205

Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
```

```
                    290              295              300
Lys Cys Phe Gly Cys Asp Gly Gly Leu Arg Cys Trp Glu Ser Gly Asp
305                 310              315              320

Asp Pro Trp Val Glu His Ala Lys Trp Phe Pro Arg Cys Glu Phe Leu
                325              330              335

Ile Arg Met Lys Gly Gln Glu Phe Val Asp Glu Ile Gln Gly Arg Tyr
            340              345              350

Pro His Leu Leu Glu Gln Leu Leu Ser Thr Ser Asp Thr Thr Gly Glu
            355              360              365

Glu Asn Ala Asp Pro Pro Ile Ile His Phe Gly Pro Gly Glu Ser Ser
370             375              380

Ser Glu Asp Ala Val Met Met Asn Thr Pro Val Val Lys Ser Ala Leu
385             390              395              400

Glu Met Gly Phe Asn Arg Asp Leu Val Lys Gln Thr Val Leu Ser Lys
                405              410              415

Ile Leu Thr Thr Gly Glu Asn Tyr Lys Thr Val Asn Asp Ile Val Ser
            420              425              430

Ala Leu Leu Asn Ala Glu Asp Glu Lys Arg Glu Glu Lys Glu Lys
            435              440              445

Gln Ala Glu Glu Met Ala Ser Asp Asp Leu Ser Leu Ile Arg Lys Asn
450             455              460

Arg Met Ala Leu Phe Gln Gln Leu Thr Cys Val Leu Pro Ile Leu Asp
465             470              475              480

Asn Leu Lys Ala Asn Val Ile Asn Lys Gln Glu His Asp Ile Ile
            485              490              495

Lys Gln Lys Thr Gln Ile Pro Leu Gln Ala Arg Glu Leu Ile Asp Thr
            500              505              510

Ile Trp Val Lys Gly Asn Ala Ala Asn Ile Phe Lys Asn Cys Leu
            515              520              525

Lys Glu Ile Asp Ser Thr Leu Tyr Lys Asn Leu Phe Val Asp Lys Asn
530             535              540

Met Lys Tyr Ile Pro Thr Glu Asp Val Ser Gly Leu Ser Leu Glu Glu
545             550              555              560

Gln Leu Arg Arg Leu Gln Glu Glu Arg Thr Cys Lys Val Cys Met Asp
                565              570              575

Lys Glu Val Ser Val Val Phe Ile Pro Cys Gly His Leu Val Cys
            580              585              590

Gln Glu Cys Ala Pro Ser Leu Arg Lys Cys Pro Ile Cys Arg Gly Ile
            595              600              605

Ile Lys Gly Thr Val Arg Thr Phe Leu Ser
    610              615

<210> SEQ ID NO 224
<211> LENGTH: 2100
<212> TYPE: DNA
<213> ORGANISM: Mus musculus

<400> SEQUENCE: 224
gacactctgc tgggcggcgg gccgcccctcc tccgggacct cccctcggga accgtcgccc     60
gcggcgctta gttaggactg gagtgcttgg cgcgaaaagg tggacaagtc ctattttcca    120
gagaagatga cttttaacag ttttgaagga actagaactt ttgtacttgc agacaccaat    180
aaggatgaag aatttgtaga agagtttaat agattaaaaa catttgctaa cttcccaagt    240
agtagtcctg tttcagcatc aacattggcg cgagctgggt ttctttatac cggtgaagga    300
```

-continued

```
gacaccgtgc aatgtttcag ttgtcatgcg gcaatagata gatggcagta tggagactca    360
gctgttggaa gacacaggag aatatcccca aattgcagat ttatcaatgg ttttattttt    420
gaaaatggtg ctgcacagtc tacaaatcct ggtatccaaa atggccagta caaatctgaa    480
aactgtgtgg gaaatagaaa tccttttgcc cctgacaggc cacctgagac tcatgctgat    540
tatctcttga gaactggaca ggttgtagat atttcagaca ccatataccc gaggaacccct   600
gccatgtgta gtgaagaagc cagattgaag tcatttcaga actggccgga ctatgctcat    660
ttaaccccca gagagttagc tagtgctggc ctctactaca caggggctga tgatcaagtg    720
caatgctttt gttgtggggg aaaactgaaa aattgggaac cctgtgatcg tgcctggtca    780
gaacacagga gacactttcc caattgcttt tttgttttgg gccggaacgt taatgttcga    840
agtgaatctg gtgtgagttc tgataggaat ttcccaaatt caacaaactc tccaagaaat    900
ccagccatgg cagaatatga agcacggatc gttacttttg gaacatggat atactcagtt    960
aacaaggagc agcttgcaag agctggattt tatgctttag gtgaaggcga taaagtgaag   1020
tgcttccact gtgaggaggg gctcacggat tggaagccaa gtgaagaccc ctgggaccag   1080
catgctaagt gctacccagg gtgcaaatac ctattggatg agaaggggca agaatatata   1140
aataatattc atttaaccca tccacttgag gaatctttgg gaagaactgc tgaaaaaaca   1200
ccaccgctaa ctaaaaaaat cgatgatacc atcttccaga atcctatggt gcaagaagct   1260
atacgaatgg gatttagctt caaggacctt aagaaaacaa tggaagaaaa aatccaaaca   1320
tccgggagca gctatctatc acttgaggtc ctgattgcag atcttgtgag tgctcagaaa   1380
gataatacgg aggatgagtc aagtcaaaact tcattgcaga aagacattag tactgaagag   1440
cagctaaggc gcctacaaga ggagaagctt tccaaaatct gtatggatag aaatattgct   1500
atcgttttt ttccttgtgg acatctggcc acttgtaaac agtgtgcaga agcagttgac   1560
aaatgtccca tgtgctacac cgtcattacg ttcaaccaaa aaattttat gtcttagtgg   1620
ggcaccacat gttatgttct tcttgctcta attgaatgtg taatgggagc gaactttaag   1680
taatcctgca tttgcattcc attagcatcc tgctgtttcc aaatggagac caatgctaac   1740
agcactgttt ccgtctaaac attcaatttc tggatctttc gagttatcag ctgtatcatt   1800
tagccagtgt tttactcgat tgaaaccttta gacagagaag cattttatag cttttcacat    1860
gtatattggt agtacactga cttgatttct atatgtaagt gaattcatca cctgcatgtt   1920
tcatgccttt tgcataagct taacaaatgg agtgttctgt ataagcatgg agatgtgatg   1980
gaatctgccc aatgacttta attggcttat tgtaaacacg gaaagaactg ccccacgctg   2040
ctgggaggat aaagattgtt ttagatgctc acttctgtgt tttaggattc tgcccattta   2100
```

<210> SEQ ID NO 225
<211> LENGTH: 496
<212> TYPE: PRT
<213> ORGANISM: Mus musculus

<400> SEQUENCE: 225

```
Met Thr Phe Asn Ser Phe Glu Gly Thr Arg Thr Phe Val Leu Ala Asp
  1               5                  10                  15

Thr Asn Lys Asp Glu Glu Phe Val Glu Glu Phe Asn Arg Leu Lys Thr
                 20                  25                  30

Phe Ala Asn Phe Pro Ser Ser Ser Pro Val Ser Ala Ser Thr Leu Ala
             35                  40                  45

Arg Ala Gly Phe Leu Tyr Thr Gly Glu Gly Asp Thr Val Gln Cys Phe
```

-continued

```
                50                  55                  60
Ser Cys His Ala Ala Ile Asp Arg Trp Gln Tyr Gly Asp Ser Ala Val
 65                  70                  75                  80
Gly Arg His Arg Arg Ile Ser Pro Asn Cys Arg Phe Ile Asn Gly Phe
                     85                  90                  95
Tyr Phe Glu Asn Gly Ala Ala Gln Ser Thr Asn Pro Gly Ile Gln Asn
                    100                 105                 110
Gly Gln Tyr Lys Ser Glu Asn Cys Val Gly Asn Arg Asn Pro Phe Ala
                115                 120                 125
Pro Asp Arg Pro Pro Glu Thr His Ala Asp Tyr Leu Leu Arg Thr Gly
            130                 135                 140
Gln Val Val Asp Ile Ser Asp Thr Ile Tyr Pro Arg Asn Pro Ala Met
145                 150                 155                 160
Cys Ser Glu Glu Ala Arg Leu Lys Ser Phe Gln Asn Trp Pro Asp Tyr
                    165                 170                 175
Ala His Leu Thr Pro Arg Glu Leu Ala Ser Ala Gly Leu Tyr Tyr Thr
                180                 185                 190
Gly Ala Asp Asp Gln Val Gln Cys Phe Cys Gly Gly Lys Leu Lys
                195                 200                 205
Asn Trp Glu Pro Cys Asp Arg Ala Trp Ser Glu His Arg Arg His Phe
            210                 215                 220
Pro Asn Cys Phe Phe Val Leu Gly Arg Asn Val Asn Val Arg Ser Glu
225                 230                 235                 240
Ser Gly Val Ser Ser Asp Arg Asn Phe Pro Asn Ser Thr Asn Ser Pro
                    245                 250                 255
Arg Asn Pro Ala Met Ala Glu Tyr Glu Ala Arg Ile Val Thr Phe Gly
                260                 265                 270
Thr Trp Ile Tyr Ser Val Asn Lys Glu Gln Leu Ala Arg Ala Gly Phe
            275                 280                 285
Tyr Ala Leu Gly Glu Gly Asp Lys Val Lys Cys Phe His Cys Gly Gly
290                 295                 300
Gly Leu Thr Asp Trp Lys Pro Ser Glu Asp Pro Trp Asp Gln His Ala
305                 310                 315                 320
Lys Cys Tyr Pro Gly Cys Lys Tyr Leu Leu Asp Glu Lys Gly Gln Glu
                325                 330                 335
Tyr Ile Asn Asn Ile His Leu Thr His Pro Leu Glu Glu Ser Leu Gly
                340                 345                 350
Arg Thr Ala Glu Lys Thr Pro Pro Leu Thr Lys Lys Ile Asp Asp Thr
            355                 360                 365
Ile Phe Gln Asn Pro Met Val Gln Glu Ala Ile Arg Met Gly Phe Ser
370                 375                 380
Phe Lys Asp Leu Lys Lys Thr Met Glu Glu Lys Ile Gln Thr Ser Gly
385                 390                 395                 400
Ser Ser Tyr Leu Ser Leu Glu Val Leu Ile Ala Asp Leu Val Ser Ala
                    405                 410                 415
Gln Lys Asp Asn Thr Glu Asp Glu Ser Ser Gln Thr Ser Leu Gln Lys
                420                 425                 430
Asp Ile Ser Thr Glu Glu Gln Leu Arg Arg Leu Gln Glu Glu Lys Leu
            435                 440                 445
Ser Lys Ile Cys Met Asp Arg Asn Ile Ala Ile Val Phe Phe Pro Cys
        450                 455                 460
Gly His Leu Ala Thr Cys Lys Gln Cys Ala Glu Ala Val Asp Lys Cys
465                 470                 475                 480
```

-continued

Pro Met Cys Tyr Thr Val Ile Thr Phe Asn Gln Lys Ile Phe Met Ser
            485                 490                 495

<210> SEQ ID NO 226
<211> LENGTH: 2474
<212> TYPE: DNA
<213> ORGANISM: Mus musculus

<400> SEQUENCE: 226

| | | | | |
|---|---|---|---|---|
| gaattccggg | agacctacac | ccccggagat | cagaggtcat | tgctggcgtt cagagcctag | 60 |
| gaagtgggct | gcggtatcag | cctagcagta | aaaccgacca | gaagccatgc acaaaactac | 120 |
| atccccagag | aaagacttgt | cccttcccct | ccctgtcatc | tcaccatgaa catggttcaa | 180 |
| gacagcgcct | ttctagccaa | gctgatgaag | agtgctgaca | ccttttgagtt gaagtatgac | 240 |
| ttttcctgtg | agctgtaccg | attgtccacg | tattcagctt | ttcccagggg agttcctgtg | 300 |
| tcagaaagga | gtctggctcg | tgctggcttt | tactacactg | gtgccaatga caaggtcaag | 360 |
| tgcttctgct | gtggcctgat | gctagacaac | tggaaacaag | gggacagtcc catggagaag | 420 |
| cacagaaagt | tgtaccccag | ctgcaacttt | gtacagactt | tgaatccagc caacagtctg | 480 |
| gaagctagtc | ctcggccttc | tcttccttcc | acggcgatga | gcaccatgcc tttgagcttt | 540 |
| gcaagttctg | agaatactgg | ctatttcagt | ggctcttact | cgagctttcc ctcagaccct | 600 |
| gtgaacttcc | gagcaaatca | agattgtcct | gctttgagca | caagtcccta ccactttgca | 660 |
| atgaacacag | agaaggccag | attactcacc | tatgaaacat | ggccattgtc ttttctgtca | 720 |
| ccagcaaagc | tggccaaagc | aggcttctac | tacataggac | ctggagatag agtggcctgc | 780 |
| tttgcgtgcg | atgggaaact | gagcaactgg | gaacgtaagg | atgatgctat gtcagagcac | 840 |
| cagaggcatt | tccccagctg | tccgttctta | aaagacttgg | gtcagtctgc ttcgagatac | 900 |
| actgtctcta | acctgagcat | gcagacacac | gcagcccgta | ttagaacatt ctctaactgg | 960 |
| ccttctagtg | cactagttca | ttcccaggaa | cttgcaagtg | cgggctttta ttatacagga | 1020 |
| cacagtgatg | atgtcaagtg | tttatgctgt | gatggtgggc | tgaggtgctg ggaatctgga | 1080 |
| gatgacccct | gggtggaaca | tgccaagtgg | tttccaaggt | gtgagtactt gctcagaatc | 1140 |
| aaaggccaag | aatttgtcag | ccaagttcaa | gctggctatc | ctcatctact tgagcagcta | 1200 |
| ttatctacgt | cagactcccc | agaagatgag | aatgcagacg | cagcaatcgt gcattttggc | 1260 |
| cctggagaaa | gttcggaaga | tgtcgtcatg | atgagcacgc | ctgtggttaa agcagccttg | 1320 |
| gaaatgggct | tcagtaggag | cctggtgaga | cagacggttc | agtggcagat cctggccact | 1380 |
| ggtgagaact | acaggaccgt | cagtgacctc | gttataggct | tactcgatgc agaagacgag | 1440 |
| atgagagagg | agcagatgga | gcaggcggcc | gaggaggagg | agtcagatga tctagcacta | 1500 |
| atccggaaga | acaaaatggt | gcttttccaa | catttgacgt | gtgtgacacc aatgctgtat | 1560 |
| tgcctcctaa | gtgcaagggc | catcactgaa | caggagtgca | atgctgtgaa acagaaacca | 1620 |
| cacaccttac | aagcaagcac | actgattgat | actgtgttag | caaaaggaaa cactgcagca | 1680 |
| acctcattca | gaaactccct | tcgggaaatt | gaccctgcgt | tatacagaga tatatttgtg | 1740 |
| caacaggaca | ttaggagtct | tcccacagat | gacattgcag | ctctaccaat ggaagaacag | 1800 |
| ttgcggcccc | tcccggagga | cagaatgtgt | aaagtgtgta | tggaccgaga ggtatccatc | 1860 |
| gtgttcattc | cctgtggcca | tctggtcgtg | tgcaaagact | cgctccctc tctgaggaag | 1920 |
| tgtcccatct | gtagagggac | catcaagggc | acagtgcgca | catttctctc ctgaacaaga | 1980 |
| ctaatggtcc | atggctgcaa | cttcagccag | gaggaagttc | actgtcactc ccagttccat | 2040 |

```
tcggaacttg aggccagcct ggatagcacg agacaccgcc aaacacacaa atataaacat    2100
gaaaaacttt tgtctgaagt caagaatgaa tgaattactt atataataat tttaattggt    2160
ttccttaaaa gtgctatttg ttcccaactc agaaaattgt ttctgtaaa  catatttaca    2220 tactacctgc atctaaagta ttcatatatt catatattca gatgtcatga gagagggttt    2280
tgttcttgtt cctgaaaagc tggtttatca tctgatcagc atatactgcg caacgggcag    2340
ggctagaatc catgaaccaa gctgcaaaga tctcacgcta ataaggcgg  aaagatttgg    2400 agaaacgaaa ggaaattctt tcctgtccaa tgtatactct tcagactaat gacctcttcc    2460
tatcaagcct tcta                                                      2474
```

<210> SEQ ID NO 227
<211> LENGTH: 602
<212> TYPE: PRT
<213> ORGANISM: Mus musculus

<400> SEQUENCE: 227

```
Met Asn Met Val Gln Asp Ser Ala Phe Leu Ala Lys Leu Met Lys Ser
  1               5                  10                  15

Ala Asp Thr Phe Glu Leu Lys Tyr Asp Phe Ser Cys Glu Leu Tyr Arg
             20                  25                  30

Leu Ser Thr Tyr Ser Ala Phe Pro Arg Gly Val Pro Val Ser Glu Arg
         35                  40                  45

Ser Leu Ala Arg Ala Gly Phe Tyr Tyr Thr Gly Ala Asn Asp Lys Val
     50                  55                  60

Lys Cys Phe Cys Cys Gly Leu Met Leu Asp Asn Trp Lys Gln Gly Asp
 65                  70                  75                  80

Ser Pro Met Glu Lys His Arg Lys Leu Tyr Pro Ser Cys Asn Phe Val
                 85                  90                  95

Gln Thr Leu Asn Pro Ala Asn Ser Leu Glu Ala Ser Pro Arg Pro Ser
            100                 105                 110

Leu Pro Ser Thr Ala Met Ser Thr Met Pro Leu Ser Phe Ala Ser Ser
        115                 120                 125

Glu Asn Thr Gly Tyr Phe Ser Gly Ser Tyr Ser Ser Phe Pro Ser Asp
    130                 135                 140

Pro Val Asn Phe Arg Ala Asn Gln Asp Cys Pro Ala Leu Ser Thr Ser
145                 150                 155                 160

Pro Tyr His Phe Ala Met Asn Thr Glu Lys Ala Arg Leu Leu Thr Tyr
                165                 170                 175

Glu Thr Trp Pro Leu Ser Phe Leu Ser Pro Ala Lys Leu Ala Lys Ala
            180                 185                 190

Gly Phe Tyr Tyr Ile Gly Pro Gly Asp Arg Val Ala Cys Phe Ala Cys
        195                 200                 205

Asp Gly Lys Leu Ser Asn Trp Glu Arg Lys Asp Asp Ala Met Ser Glu
    210                 215                 220

His Gln Arg His Phe Pro Ser Cys Pro Phe Leu Lys Asp Leu Gly Gln
225                 230                 235                 240

Ser Ala Ser Arg Tyr Thr Val Ser Asn Leu Ser Met Gln Thr His Ala
                245                 250                 255

Ala Arg Ile Arg Thr Phe Ser Asn Trp Pro Ser Ser Ala Leu Val His
            260                 265                 270

Ser Gln Glu Leu Ala Ser Ala Gly Phe Tyr Tyr Thr Gly His Ser Asp
        275                 280                 285
```

```
Asp Val Lys Cys Leu Cys Cys Asp Gly Gly Leu Arg Cys Trp Glu Ser
    290                 295                 300
Gly Asp Asp Pro Trp Val Glu His Ala Lys Trp Phe Pro Arg Cys Glu
305                 310                 315                 320
Tyr Leu Leu Arg Ile Lys Gly Gln Glu Phe Ser Gln Val Gln Ala
                325                 330                 335
Gly Tyr Pro His Leu Leu Glu Gln Leu Leu Ser Thr Ser Asp Ser Pro
                340                 345                 350
Glu Asp Glu Asn Ala Asp Ala Ala Ile Val His Phe Gly Pro Gly Glu
                355                 360                 365
Ser Ser Glu Asp Val Val Met Met Ser Thr Pro Val Val Lys Ala Ala
370                 375                 380
Leu Glu Met Gly Phe Ser Arg Ser Leu Val Arg Gln Thr Val Gln Trp
385                 390                 395                 400
Gln Ile Leu Ala Thr Gly Glu Asn Tyr Arg Thr Val Ser Asp Leu Val
                405                 410                 415
Ile Gly Leu Leu Asp Ala Glu Asp Glu Met Arg Glu Gln Met Glu
                420                 425                 430
Gln Ala Ala Glu Glu Glu Glu Ser Asp Asp Leu Ala Leu Ile Arg Lys
                435                 440                 445
Asn Lys Met Val Leu Phe Gln His Leu Thr Cys Val Thr Pro Met Leu
            450                 455                 460
Tyr Cys Leu Leu Ser Ala Arg Ala Ile Thr Glu Gln Glu Cys Asn Ala
465                 470                 475                 480
Val Lys Gln Lys Pro His Thr Leu Gln Ala Ser Thr Leu Ile Asp Thr
                485                 490                 495
Val Leu Ala Lys Gly Asn Thr Ala Ala Thr Ser Phe Arg Asn Ser Leu
                500                 505                 510
Arg Glu Ile Asp Pro Ala Leu Tyr Arg Asp Ile Phe Val Gln Gln Asp
                515                 520                 525
Ile Arg Ser Leu Pro Thr Asp Asp Ile Ala Ala Leu Pro Met Glu Glu
            530                 535                 540
Gln Leu Arg Pro Leu Pro Glu Asp Arg Met Cys Lys Val Cys Met Asp
545                 550                 555                 560
Arg Glu Val Ser Ile Val Phe Ile Pro Cys Gly His Leu Val Val Cys
                565                 570                 575
Lys Asp Cys Ala Pro Ser Leu Arg Lys Cys Pro Ile Cys Arg Gly Thr
                580                 585                 590
Ile Lys Gly Thr Val Arg Thr Phe Leu Ser
            595                 600
```

<210> SEQ ID NO 228
<211> LENGTH: 2416
<212> TYPE: DNA
<213> ORGANISM: Mus musculus

<400> SEQUENCE: 228

```
ctgtggtgga gatctattgt ccaagtggtg agaaacttca tctggaagtt taagcggtca    60
gaaatactat tactactcat ggacaaaact gtctcccaga gactcgccca aggtacctta   120
cacccaaaaa cttaaacgta taatggagaa gagcacaatc ttgtcaaatt ggacaaagga   180
gagcgaagaa aaaatgaagt ttgacttttc gtgtgaactc taccgaatgt ctacatattc   240
agcttttccc aggggagttc ctgtctcaga gaggagtctg gctcgtgctg gcttttatta   300
tacaggtgtg aatgacaaag tcaagtgctt ctgctgtggc ctgatgttgg ataactggaa   360
```

```
acaagggac agtcctgttg aaaagcacag acagttctat cccagctgca gctttgtaca    420
gactctgctt tcagccagtc tgcagtctcc atctaagaat atgtctcctg tgaaaagtag    480
atttgcacat tcgtcacctc tggaacgagg tggcattcac tccaacctgt gctctagccc    540
tcttaattct agagcagtgg aagacttctc atcaaggatg gatccctgca gctatgccat    600
gagtacagaa gaggccagat ttcttactta cagtatgtgg cctttaagtt ttctgtcacc    660
agcagagctg gccagagctg gcttctatta catagggcct ggagacaggg tggcctgttt    720
tgcctgtggt gggaaactga gcaactggga accaaaggat tatgctatgt cagagcaccg    780
cagacatttt ccccactgtc catttctgga aaatacttca gaaacacaga ggtttagtat    840
atcaaatcta agtatgcaga cacactctgc tcgattgagc acatttctgt actggccacc    900
tagtgttcct gttcagcccg agcagcttgc aagtgctgga ttctattacg tggatcgcaa    960
tgatgatgtc aagtgccttt gttgtgatgg tggcttgaga tgttgggaac ctggagatga   1020
cccctggata gaacacgcca atggtttcc aaggtgtgag ttcttgatac ggatgaaggg    1080
tcaggagttt gttgatgaga ttcaagctag atatcctcat cttcttgagc agctgttgtc   1140
cacttcagac accccaggag aagaaaatgc tgaccctaca gagacagtgg tgcattttgg   1200
ccctggagaa agttcgaaag atgtcgtcat gatgagcacg cctgtggtta aagcagcctt   1260
ggaaatgggc ttcagtagga gcctggtgag acagacggtt cagcggcaga tcctggccac   1320
tggtgagaac tacaggaccg tcaatgatat tgtctcagta cttttgaatg ctgaagatga   1380
gagaagagaa gaggagaagg aaagacagac tgaagagatg gcatcaggtg acttatcact   1440
gattcggaag aatagaatgg ccctctttca acagttgaca catgtccttc ctatcctgga   1500
taatcttctt gaggccagtg taattacaaa acaggaacat gatattatta gacagaaaac   1560
acagataccc ttacaagcaa gagagcttat tgacaccgtt ttagtcaagg gaaatgctgc   1620
agccaacatc ttcaaaaact ctctgaaggg aattgactcc acgttatatg aaaacttatt   1680
tgtggaaaag aatatgaagt atattccaac agaagacgtt tcaggcttgt cattggaaga   1740
gcagttgcgg agattacaag aagaacgaac ttgcaaagtg tgtatggaca gagaggtttc   1800
tattgtgttc attccgtgtg gtcatctagt agtctgccag gaatgtgccc cttctctaag   1860
gaagtgcccc atctgcaggg ggacaatcaa ggggactgtg cgcacatttc tctcatgagt   1920
gaagaatggt ctgaaagtat tgttggacat cagaagctgt cagaacaaag aatgaactac   1980
tgatttcagc tcttcagcag gacattctac tctctttcaa gattagtaat cttgctttat   2040
gaagggtagc attgtatatt taagcttagt ctgttgcaag ggaaggtcta tgctgttgag   2100
ctacaggact gtgtctgttc cagagcagga gttgggatgc ttgctgtatg tccttcagga   2160
cttcttggga tttgggaatt tggggaaagc tttggaatcc agtgatgtgg agctcagaaa   2220
tcctggaacc agtgactctg gtactcagta gatagggtac cctgtacttc ttggtgcttt   2280
tccagtctgg gaaataagga ggaatctgct gctggtaaaa atttgctgga tgtgagaaat   2340
agatgaaagt gtttcgggtg ggggcgtgca tcagtgtagt gtgtgcaggg atgtatgcag   2400
gccaaacact gtgtag                                                   2416
```

<210> SEQ ID NO 229
<211> LENGTH: 591
<212> TYPE: PRT
<213> ORGANISM: Mus musculus

<400> SEQUENCE: 229

-continued

```
Met Glu Lys Ser Thr Ile Leu Ser Asn Trp Thr Lys Glu Ser Glu
 1               5                  10                  15

Lys Met Lys Phe Asp Phe Ser Cys Glu Leu Tyr Arg Met Ser Thr Tyr
             20                  25                  30

Ser Ala Phe Pro Arg Gly Val Pro Val Ser Glu Arg Ser Leu Ala Arg
         35                  40                  45

Ala Gly Phe Tyr Tyr Thr Gly Val Asn Asp Lys Val Lys Cys Phe Cys
     50                  55                  60

Cys Gly Leu Met Leu Asp Asn Trp Lys Gln Gly Asp Ser Pro Val Glu
 65                  70                  75                  80

Lys His Arg Gln Phe Tyr Pro Ser Cys Ser Phe Val Gln Thr Leu Leu
                 85                  90                  95

Ser Ala Ser Leu Gln Ser Pro Ser Lys Asn Met Ser Pro Val Lys Ser
             100                 105                 110

Arg Phe Ala His Ser Ser Pro Leu Glu Arg Gly Gly Ile His Ser Asn
         115                 120                 125

Leu Cys Ser Ser Pro Leu Asn Ser Arg Ala Val Glu Asp Phe Ser Ser
130                 135                 140

Arg Met Asp Pro Cys Ser Tyr Ala Met Ser Thr Glu Glu Ala Arg Phe
145                 150                 155                 160

Leu Thr Tyr Ser Met Trp Pro Leu Ser Phe Leu Ser Pro Ala Glu Leu
                 165                 170                 175

Ala Arg Ala Gly Phe Tyr Tyr Ile Gly Pro Gly Asp Arg Val Ala Cys
             180                 185                 190

Phe Ala Cys Gly Gly Lys Leu Ser Asn Trp Glu Pro Lys Asp Tyr Ala
         195                 200                 205

Met Ser Glu His Arg Arg His Phe Pro His Cys Pro Phe Leu Glu Asn
     210                 215                 220

Thr Ser Glu Thr Gln Arg Phe Ser Ile Ser Asn Leu Ser Met Gln Thr
225                 230                 235                 240

His Ser Ala Arg Leu Arg Thr Phe Leu Tyr Trp Pro Ser Val Pro
                 245                 250                 255

Val Gln Pro Glu Gln Leu Ala Ser Ala Gly Phe Tyr Tyr Val Asp Arg
             260                 265                 270

Asn Asp Asp Val Lys Cys Leu Cys Cys Asp Gly Gly Leu Arg Cys Trp
         275                 280                 285

Glu Pro Gly Asp Asp Pro Trp Ile Glu His Ala Lys Trp Phe Pro Arg
     290                 295                 300

Cys Glu Phe Leu Ile Arg Met Lys Gly Gln Glu Phe Val Asp Glu Ile
305                 310                 315                 320

Gln Ala Arg Tyr Pro His Leu Leu Glu Gln Leu Leu Ser Thr Ser Asp
                 325                 330                 335

Thr Pro Gly Glu Glu Asn Ala Asp Pro Thr Glu Thr Val His Phe
             340                 345                 350

Gly Pro Gly Glu Ser Ser Lys Asp Val Val Met Met Ser Thr Pro Val
         355                 360                 365

Val Lys Ala Ala Leu Glu Met Gly Phe Ser Arg Ser Leu Val Arg Gln
     370                 375                 380

Thr Val Gln Arg Gln Ile Leu Ala Thr Gly Glu Asn Tyr Arg Thr Val
385                 390                 395                 400

Asn Asp Ile Val Ser Val Leu Asn Ala Glu Asp Glu Arg Arg Glu
                 405                 410                 415

Glu Glu Lys Glu Arg Gln Thr Glu Glu Met Ala Ser Gly Asp Leu Ser
```

```
                        420             425             430
Leu Ile Arg Lys Asn Arg Met Ala Leu Phe Gln Gln Leu Thr His Val
        435                 440                 445
Leu Pro Ile Leu Asp Asn Leu Leu Glu Ala Ser Val Ile Thr Lys Gln
    450                 455                 460
Glu His Asp Ile Ile Arg Gln Lys Thr Gln Ile Pro Leu Gln Ala Arg
465                 470                 475                 480
Glu Leu Ile Asp Thr Val Leu Val Lys Gly Asn Ala Ala Ala Asn Ile
            485                 490                 495
Phe Lys Asn Ser Leu Lys Gly Ile Asp Ser Thr Leu Tyr Glu Asn Leu
                500                 505                 510
Phe Val Glu Lys Asn Met Lys Tyr Ile Pro Thr Glu Asp Val Ser Gly
            515                 520                 525
Leu Ser Leu Glu Glu Gln Leu Arg Arg Leu Gln Glu Glu Arg Thr Cys
    530                 535                 540
Lys Val Cys Met Asp Arg Glu Val Ser Ile Val Phe Ile Pro Cys Gly
545                 550                 555                 560
His Leu Val Val Cys Gln Glu Cys Ala Pro Ser Leu Arg Lys Cys Pro
            565                 570                 575
Ile Cys Arg Gly Thr Ile Lys Gly Thr Val Arg Thr Phe Leu Ser
            580                 585                 590

<210> SEQ ID NO 230
<211> LENGTH: 6669
<212> TYPE: DNA
<213> ORGANISM: Homo sapiens
<220> FEATURE:
<221> NAME/KEY: misc_feature
<222> LOCATION: (1)...(6669)
<223> OTHER INFORMATION: n=a,t,c, or g

<400> SEQUENCE: 230
ttgctctgtc acccagtttg gagtgcagtt atgcagtctc acactgcaag ctctgcctca      60
tgggctcaag tgaacctcct gcctcagcct ctcaagtagc tgggaccaca ggcaggtgcc     120
accatgtctg ctaattttt gagtttcttt gtagagatgg tgttttgcca agtcacccag      180
tttgaggctg tctcaaaca cctgggctca agcaatccat ctacctcagc ctcccaaagt      240
gctgggatta caggagtgag ccatggcatg aggccttgtg gggtgtctct tttaaatgaa     300
agcatactct gtttacgtat ttgatatgaa ggaatatcct tcctttccac aaagacaaaa     360
attatcctat tttctcaaa acatatgtcc tttttctcta cttttcattt tgttactttt      420
tgatggacac atgtgttaca ttgatttcac tttctcataa ttctgctgta agaaaaacaa     480
tagtgccagt tcaatgacaa atagcaacag tctgttattg ctagactgtt actgttagtg     540
gagactacca gaacagtcag tcccagtgtc agggaatcaa agagaacatg ttccctctct     600
aaagggcaca gctgctgctc agctttagct gattgctgcc ctgcaggact ataggcccag     660
tgttgctaga tcttttgatg tttcaagaga gcttggaat ctagaatgtg atgggaagtc      720
tcttacattt aaacatgttg gcaattaatg gtaagattta aaaatactgt ggtccaagaa     780
aaaaatggat ttggaaactg gattaaattc aaatgaggca tgcagattaa tctacagcat     840
ggtacaatgt gaatttctg gtttctttaa ttgcactgta attaggtaag atgttagctt      900
tggggaagct aagtgcagag tatgcagaaa ctattatttt tgtaagtttt ctctaagtat     960
aaataaattt caaataaaa ataaaaactt agtaaagaac tataatgcaa ttctatgtaa     1020
gccaaacata atatgtcttc cagtttgaaa cctctgggtt ttatttttatt ttattttatt   1080
```

-continued

```
tttgagacag agtcttgctg tgtcacccag gctggagtgt agtggcacta tttcggccca    1140
ctgcaacctc cacctcccag gctcaaatga ttctcctgcc tcagcctccg gagtagctgg    1200
gattacaggc gcgtaccacc acacccagct aattttttgta ttttttagtag agatgggtt    1260
tcaccatttt ggccaggctg gttttgaact cctgacctca agtgatccac ttgtcttggc    1320
ctcccaaaat gctgggatta caggcgtgag ccactgcacc aggcagaggc ctctgttttt    1380
tatctctttt tggcctctac agtgcctagt aaagcacctg atacatggta aacgatcagt    1440
aattactagt actctatttt ggagaaaatg attttttaaa aagtcattgt gttccatcca    1500
tgagtcgttt gagttttaaa actgtctttt tgtttgtttt tgaacaggtt tacaaaggag    1560
gaaaacgact tcttctagat ttttttttca gtttcttcta taaatcaaaa catctcaaaa    1620
tggagaccta aaatccttaa agggacttag tctaatctcg ggaggtagtt ttgtgcatgg    1680
gtaaacaaat taagtattaa ctggtgtttt actatccaaa gaatgctaat tttataaaca    1740
tgatcgagtt atataaggta taccataatg agtttgattt tgaatttgat ttgtggaaat    1800
aaaggaaaag tgattctagc tggggcatat tgttaaagca ttttttttcag agttggccag    1860
gcagtctcct actggcacat tctcccatta tgtagaatag aaatagtacc tgtgtttggg    1920
aaagattta aaatgagtga cagttatttg gaacaaagc ctaataatca atccactgca    1980
aattaaagaa acatgcagat gaaagttttg acacattaaa atacttctac agtgacaaag    2040
aaaaatcaag aacaaagctt tttgatatgt gcaacaaatt tagaggaagt aaaaagataa    2100
atgtgatgat tggtcaagaa attatccagt tatttacaag gccactgata ttttaaacgt    2160
ccaaaagttt gttaaatgg gctgttaccg ctgagaatga tgaggatgag aatgatggtt    2220
gaaggttaca ttttaggaaa tgaagaaact tagaaaatta atataaagac agtgatgaat    2280
acaaagaaga tttttataac aatgtgtaaa attttggcc agggaaagga atattgaagt    2340
tagatacaat tacttacctt tgagggaaat aattgttggt aatgagatgt gatgtttctc    2400
ctgccacctg gaaacaaagc attgaagtct gcagttgaaa agcccaacgt ctgtgagatc    2460
caggaaacca tgcttgcaaa ccactggtaa aaaaaaaaaa aaaaaaaaaa aaagccacag    2520
tgacttgctt attggtcatt gctagtatta tcgactcaga acctctttac taatggctag    2580
taaatcataa ttgagaaatt ctgaattttg acaaggtctc tgctgttgaa atggtaaatt    2640
tattatttt tttgtcatga taaattctgg ttcaaggtat gctatccatg aaataatttc    2700
tgaccaaaac taaattgatg caatttgatt atccatctta gcctacagat ggcatctggt    2760
aacttttgac tgtttttaaaa aataaatcca ctatcagagt agatttgatg ttggcttcag    2820
aaacatttag aaaacaaaa gttcaaaat gttttcagga ggtgataagt tgaataactc    2880
tacaatgtta gttctttgag ggggacaaaa aatttaaaat ctttgaaagg tcttattta    2940
cagccatatc taaattatct aagaaaaatt tttaacaaag ggaatgaaat atatatcatg    3000
attctgttt tccaaaagta acctgaatat agcaatgaag ttcagttttg ttattggtag    3060
tttgggcaga gtctcttttt gcagcacctg ttgtctacca taattacaga ggacatttcc    3120
atgttctagc caagtatact attagaataa aaaaacttaa cattgagttg cttcaacagc    3180
atgaaactga gtccaaaaga ccaaatgaac aaacacatta atctctgatt atttatttta    3240
aatagaatat ttaattgtgt aagatctaat agtatcatta tacttaagca atcatattcc    3300
tgatgatcta tgggaaataa ctattattta attaatattg aaaccaggtt ttaagatgtg    3360
ttagccagtc ctgttactag taaatctctt tatttggaga gaaattttag attgttttgt    3420
```

-continued

```
tctccttatt agaaggattg tagaaagaaa aaaatgactg attggagaaa aattggggat    3480
atatcatatt tcactgaatt caaaatgtct tcagttgtaa atcttaccat tattttacgt    3540
acctctaaga aataaaagtg cttctaatta aaatatgatg tcattaatta tgaaatactt    3600
cttgataaca gaagttttaa aatagccatc ttagaatcag tgaaatatgg taatgtatta    3660
ttttcctcct tgagtnagg tcttgtgctt tttnttcctg gccactaaat ntcaccatnt     3720
ccaanaagca aantaaacct attctgaata tttttgctgt gaaacacttg ncagcagagc    3780
tttcccncca tgnnagaagc ttcatgagtc acacattaca tctttgggtt gattgaatgc    3840
cactgaaaca tttctagtag cctggagnag ttgacctacc tgtggagatg cctgccatta    3900
aatggcatcc tgatggctta atacacatca ctcttctgtg nagggtttta attttcaaca    3960
cagcttactc tgtagcatca tgtttacatt gtatgtataa agattatacn aaggtgcaat    4020
tgtgtatttc ttccttaaaa tgtatcagta taggatttag aatctccatg ttgaaactct    4080
aaatgcatag aaataaaaat aataaaaaat ttttcattt ggcttttcag cctagtatta    4140
aaactgataa aagcaaagcc atgcacaaaa ctacctccct agagaaaggc tagtcccttt    4200
tcttccccat tcatttcatt atgaacatag tagaaaacag catattctta tcaaatttga    4260
tgaaaagcgc caacacgttt gaactgaaat acgacttgtc atgtgaactg taccgaatgt    4320
ctacgtattc cacttttcct gctggggttc ctgtctcaga aaggagtctt gctcgtgctg    4380
gtttctatta cactggtgtg aatgacaagg tcaaatgctt ctgttgtggc ctgatgctgg    4440
ataactggaa aagaggagac agtcctactg aaaagcataa aaagttgtat cctagctgca    4500
gattcgttca gagtctaaat tccgttaaca acttggaagc tacctctcag cctacttttc    4560
cttcttcagt aacacattcc acacactcat tacttccggg tacagaaaac agtggatatt    4620
tccgtggctc ttattcaaac tctccatcaa atcctgtaaa ctccagagca atcaagaat    4680 tttctgcctt gatgagaagt tcctaccct gtccaatgaa taacgaaaat gccagattac     4740 ttactttca gacatggcca ttgacttttc tgtcgccaac agatctggca cgagcaggct    4800
tttactacat aggacctgga gacagagtgg cttgctttgc ctgtggtgga aaattgagca    4860
attgggaacc gaaggataat gctatgtcag aacacctgag acattttccc aaatgcccat    4920
ttatagaaaa tcagcttcaa gacacttcaa gatacacagt ttctaatctg agcatgcaga    4980
cacatgcagc ccgctttaaa acattcttta actggccctc tagtgttcta gttaatcctg    5040
agcagcttgc aagtgcgggt ttttattatg tgggtaacag tgatgatgtc aaatgctttt    5100
gctgtgatgg tggactcagg tgttgggaat ctggagatga tccatgggtt caacatgcca    5160
agtggtttcc aaggtgtgag tacttgataa gaattaaagg acaggagttc atccgtcaag    5220
ttcaagccag ttaccctcat ctacttgaac agctgctatc cacatcagac agcccaggag    5280
atgaaaatgc agagtcatca attatccatt ttgaacctgg agaagaccat tcagaagatg    5340
caatcatgat gaatactcct gtgattaatg ctgccgtgga aatgggcttt agtagaagcc    5400
tggtaaaaca gacagttcag agaaaaatcc tagcaactgg agagaattat agactagtca    5460
atgatcttgt gttagactta ctcaatgcag aagatgaaat aagggaagag gagagagaaa    5520
gagcaactga ggaaaaagaa tcaaatgatt tattattaat ccggaagaat agaatggcac    5580 ttttttcaaca tttgacttgt gtaattccaa tcctggatag tctactaact gccggaatta    5640
ttaatgaaca agaacatgat gttattaaac agaagacaca gacgtcttta caagcaagag    5700
aactgattga tacgatttta gtaaaaggaa atattgcagc cactgtattc agaaactctc    5760
tgcaagaagc tgaagctgtg ttatatgagc atttatttgt gcaacaggac ataaaatata    5820
```

```
ttcccacaga agatgtttca gatctaccag tggaagaaca attgcggaga ctacaagaag      5880
aaagaacatg taaagtgtgt atggacaaag aagtgtccat agtgtttatt ccttgtggtc      5940
atctagtagt atgcaaagat tgtgctcctt cttttaagaaa gtgtcctatt tgtaggagta    6000
caatcaaggg tacagttcgt acatttcttt catgaagaag aaccaaaaca tcgtctaaac     6060
tttagaatta atttattaaa tgtattataa ctttaacttt tatcctaatt tggtttcctt      6120 aaaatttta tttatttaca actcaaaaaa cattgttttg tgtaacatat ttatatatgt      6180
atctaaacca tatgaacata tatttttag aaactaagag aatgataggc ttttgttctt      6240
atgaacgaaa aagaggtagc actacaaaca caatattcaa tcaaaatttc agcattattg     6300
aaattgtaag tgaagtaaaa cttaagatat ttgagttaac ctttaagaat tttaaatatt    6360
ttggcattgt actaataccg ggaacatgaa gccaggtgtg gtggtatgtg cctgtagtcc    6420
caggctgagg caagagaatt acttgagccc aggagtttga atccatcctg ggcagcatac    6480
tgagaccctg ccttaaaaa caaacagaac aaaaacaaaa caccagggac acatttctct     6540 gtctttttg atcagtgtcc tatacatcga aggtgtgcat atatgttgaa tcacatttta     6600
gggacatggt gttttataa agaattctgt gagaaaaaat ttaataaagc aaccaaaaaa    6660
aaaaaaaa                                                              6669

<210> SEQ ID NO 231
<211> LENGTH: 3000
<212> TYPE: DNA
<213> ORGANISM: Homo sapiens

<400> SEQUENCE: 231
ttgcaggtac ttagaatttt tcctgagcca ccctctagag ggcagtgtta catatatatc       60
tgtaattatc cagttacaac aaaaaaaggg ctctcattca tgcatgaaaa tcagaaatat     120
ttcatactct taaagaacac attggaacca atattatgat taaaacatat tttgctaagc    180
aaagagatat taaaaattaa ttcattaaca ttctgaacat ttttaacttt gtaaaaacaa    240
ctttgatgcc ttgaatatat aatgattcat tataacaatt atgcatagat tttaataatc    300
tgcatatttt atgctttcat gttttttccta attaatgatt tgacatggtt aataattata    360
atatattctg catcacagtt tacatattta tgtaaaataa gcatttaaaa attattagtt    420
ttattctgcc tgcttaaata ttactttcct caaaaagaga aaacaaaaat gctagatttt    480
actttatgac ttgaatgatg tggtaatgtc gaactctagt atttagaatt agaatgtttc    540
ttagcggtcg tgtagttatt tttatgtcat aagtggataa tttgttagct cctataacaa    600
aagtctgttg cttgtgtttc acattttgga tttcctaata taatgttctc tttttagaaa    660
aggtggacaa gtcctatttt caagagaaga tgacttttaa cagttttgaa ggatctaaaa    720
cttgtgtacc tgcagacatc aataaggaag aagaatttgt agaagagttt aatagattaa    780
aaacttttgc taattttcca agtggtagtc ctgtttcagc atcaacactg cgcagagcag    840
ggtttctttta tactggtgaa ggagataccg tgcggtgctt tagttgtcat gcagctgtag    900
atagatggca atatgagac tcagcagttg aagacacag gaaagtatcc ccaaattgca     960
gatttatcaa cggcttttat cttgaaaata gtgccacgtc gtctacaaat tctggtatcc   1020
agaatggtca gtacaaagtt gaaaactatc tgggaagcaa agatcatttt gccttagaca  1080
ggccatctga gacacatgca gactatcttt tgagaactgg gcaggttgta gatatatcag   1140
acaccatata cccgaggaac cctgccatgt attgtgaaga agctagatta aagtcctttc   1200
agaactggcc agactatgct cacctaaccc caagagagtt agcaagtgct ggactctact   1260
acacaggtat tggtgaccaa gtgcagtgct tttgttgtgg tggaaaactg aaaaattggg   1320
aaccttgtga tcgtgcctgg tcagaacaca ggcgacactt tcctaattgc ttctttgttt   1380
tgggccggaa tcttaatatt cgaagtgaat ctgatgctgt gagttctgat aggaatttcc   1440
caaattcaac aaatcttcca agaaatccat ccatggcaga ttatgaagca cggatctttta  1500
cttttgggac atggatatac tcagttaaca aggagcagct cagtttcaag gacattaaga   1560
ctttaggtga aggtgataaa gtaaagtgct ttcactgtgg aggagggcta actgattgga    1620
agcccagtga agacccttgg gaacaacatg ctaaatggta tccagggtgc aaatatctgt    1680
tagaacagaa gggacaagaa tatataaaca atattcattt aactcattca cttgaggagt   1740
gtctggtaag aactactgag aaaacaccac cactaactag aagaattgat gataccatct    1800
tccaaaatcc tatggtacaa gaagctatac gaatgggttt cagtttcaag gacattaaga   1860
aaataatgga ggaaaaaatt cagatatctg ggagcaacta taaatcactt gaggttctgg    1920
ttgcagatct agtgaatgct cagaaagaca gtatgcaaga tgagtcaagt cagacttcat    1980
tacagaaaga gattagtact gaagagcagc taaggcgcct gcaagaggag aagctttgca    2040
aatctgtat ggatagaaat attgctatcg tttttgttcg ttgtgacat ctagtcactt     2100
gtaaacaatg tgctgaagca gttgacaagt gtcccatgtg ctacacagtc attactttca    2160
agcaaaaaat ttttatgtct taatctaact ctatagtagg catgttatgt tgttcttatt    2220
accctgattg aatgtgtgat gtgaactgac tttaagtaat caggattgaa ttccattagc    2280
attttgctacc aagtaggaaa aaaaatgtac atggcagtgt tttagttggc aatataatct    2340
ttgaatttct tgattttttca gggtattagc tgtattatcc atttttttta ctgttattta   2400
```

-continued

```
attgaaacca tagactaaga ataagaagca tcatactata actgaacaca atgtgtattc  2460
atagtatact gatttaattt ctaagtgtaa gtgaattaat catctggatt ttttattctt  2520
ttcagatagg cttaacaaat ggagctttct gtatataaat gtggagatta gagttaatct  2580
ccccaatcac ataatttgtt ttgtgtgaaa aaggaataaa ttgttccatg ctggtggaaa  2640
gatagagatt gtttttagag gttggttgtt gtgttttagg attctgtcca ttttctttta  2700
aagttataaa cacgtacttg tgcgaattat tttttttaaag tgatttgcca tttttgaaag  2760
cgtatttaat gatagaatac tatcgagcca acatgtactg acatggaaag atgtcaaaga  2820
tatgttaagt gtaaaatgca agtggcaaaa cactatgtat agtctgagcc agatcaaagt  2880
atgtatgttt ttaatatgca tagaacaaaa gatttggaaa gatatacacc aaactgttaa  2940
atgtggtttc tcttcgggga ggggggatt ggggagggg ccccataggg gttttatagg  3000
```

ANTISENSE IAP NUCLEIC ACIDS AND USES THEREOF

FIELD OF THE INVENTION

The invention relates to antisense IAP nucleic acids and methods of using them to increase apoptosis.

BACKGROUND OF THE INVENTION

One way by which cells die is referred to as apoptosis, or programmed cell death. Apoptosis often occurs as a normal part of the development and maintenance of healthy tissues. The process may occur so rapidly that it is difficult to detect.

The apoptosis pathway is now known to play a critical role in embryonic development, viral pathogenesis, cancer, autoimmune disorders, and neurodegenerative diseases, as well as other events. The failure of an apoptotic response has been implicated in the development of cancer, autoimmune disorders, such as lupus erythematosis and multiple sclerosis, and in viral infections, including those associated with herpes virus, poxvirus, and adenovirus.

Baculoviruses encode proteins that are termed inhibitors of apoptosis (IAPs) because they inhibit the apoptosis that would otherwise occur when insect cells are infected by the virus. These proteins are thought to work in a manner that is independent of other viral proteins. The baculovirus IAP genes include sequences encoding a ring zinc finger-like motif (RZF), which is presumed to be directly involved in DNA binding, and two N-terminal domains that consist of a 70 amino acid repeat motif termed a BIR domain (Baculovirus IAP Repeat).

The role of apoptosis in cancer has only recently been appreciated. The identification of growth promoting "oncogenes" in the late 1970's gave rise to an almost universal focus on cellular proliferation that dominated research in cancer biology for many years. Long-standing dogma held that anti-cancer therapies preferentially targeted rapidly dividing cancer cells relative to "normal" cells. This explanation was not entirely satisfactory, since some slow growing tumors are easily treated, while many rapidly dividing tumor types are extremely resistant to anti-cancer therapies. Progress in the cancer field has now led to a new paradigm in cancer biology wherein neoplasia is viewed as a failure to execute normal pathways of programmed cell death. Normal cells receive continuous feedback from their neighbors through various growth factors, and commit "suicide" if removed from this context. Cancer cells somehow ignore these commands and continue inappropriate proliferation. Cancer therapies, including radiation and many chemotherapies, have traditionally been viewed as causing overwhelming cellular injury. New evidence suggests that cancer therapies actually work by triggering apoptosis.

Both normal cell types and cancer cell types display a wide range of susceptibility to apoptotic triggers, although the determinants of this resistance are only now under investigation. Many normal cell types undergo temporary growth arrest in response to a sub-lethal dose of radiation or cytotoxic chemical, while cancer cells in the vicinity undergo apoptosis. This provides the crucial treatment "window" of appropriate toxicity that allows successful anti-cancer therapy. It is therefore not surprising that resistance of tumor cells to apoptosis is emerging as a major category of cancer treatment failure.

Compared to the numerous growth-promoting oncogenes identified to date (>100), relatively few genes have been isolated that regulate apoptosis. The Bcl-2 gene was first identified as an oncogene associated with the development of follicular lymphomas. In contrast to all other oncogenes identified to date, Bcl-2 displays no ability to promote cell proliferation, and instead has been demonstrated to suppress apoptosis by a variety of triggers. Elevated Bcl-2 expression is associated with a poor prognosis in neuroblastoma, prostate and colon cancer, and can result in a multidrug resistant phenotype in vitro. Although the study of Bcl-2 has helped revolutionize cancer paradigms, the vast majority of human malignancies do not demonstrate aberrant Bcl-2 expression.

In contrast to the findings with Bcl-2, mutation of the p53 tumor suppresser gene has been estimated to occur in up to 50% of human cancers and is the most frequent genetic change associated with cancer to date. The p53 protein plays a crucial role in surveying the genome for DNA damage. The cell type and degree of damage determines whether the cell will undergo growth arrest and repair, or initiate apoptosis. Mutations in p53 interfere with this activity, rendering the cell resistant to apoptosis by a wide range of cellular insults. Some progress has been made in understanding the molecular biology of p53, but many questions remain. p53 is known to function as a transcription factor, with the ability to positively or negatively regulate the expression of a variety of genes involved in cell cycle control, DNA repair, and apoptosis (including the anti-apoptotic Bcl-2 gene described above and the related pro-apoptotic gene Bax). The drug resistant phenotype conferred by p53 alterations has been linked to Bcl-2/Bax regulation, but this correlation does not hold for most cancer types, leaving open the possibility that other critical genes regulated by p53 remain to be identified.

SUMMARY OF THE INVENTION

We have discovered that inhibitor of apoptosis (IAP) protein overexpression is associated with a wide range of cancer types including ovarian cancer, adenocarcinoma, lymphoma, and pancreatic cancer. In addition, we have found that nuclear localization, fragmentation of the IAPs, and overexpression of the IAPs in the presence of p53 mutations correlate with a cancer diagnosis, a poor prognosis, and resistance to numerous chemotherapeutic cancer drugs. These discoveries provide diagnostic, prognostic, and therapeutic compounds and methods for the detection and treatment of proliferative diseases. One way in which the expression of an IAP in a cell can be decreased is by administering to the cell a negative regulator of the IAP apoptotic pathway, for example, an antisense nucleic acid.

In general, the invention features methods and reagents useful for inducing apoptosis in a cell. The methods and reagents of the invention are useful in treating cancers, and other proliferative diseases.

In a first aspect, the invention features an inhibitor of apoptosis (IAP) antisense nucleic acid that inhibits IAP biological activity, regardless of the length of the antisense nucleic acid. In preferred embodiments, the IAP is XIAP, HIAP1, or HIAP2. In other preferred embodiments, the antisense nucleic acid is mammalian, for example, mouse or human. In yet another embodiment, the antisense nucleic acid is between 8 and 30 nucleotides in length.

In still other further preferred embodiments, the XIAP antisense is chosen from any one of SEQ ID NOS: 1 through 96, and the HIAP1 antisense is chosen from any one of SEQ ID NOS: 97 through 194. Preferably the IAP biological activity is inhibition of apoptosis or inhibition of IAP RNA or polypeptide expression. The antisense nucleic acid may comprise at least one modified internucleoside linkage.

Preferably the modified internucleoside linkage is a phosphorothioate, a methylphosphonate, a phosphotriester, a phosphorodithioate, or a phosphoselenate linkage. In addition, the antisense nucleic acid may comprise at least one modified sugar moiety. Preferably this modified sugar moiety is a 2'-O methoxyethyl group or a 2'-O methyl group. In still another preferred embodiment, the antisense nucleic acid is a chimeric nucleic acid. Preferably the chimeric nucleic acid comprises DNA residues linked together by phosphorothioate linkages, and the DNA residues are flanked on each side by at least one 2'-O methyl RNA residue linked together by a phosphorothioate linkage. More preferably the DNA residues are flanked on each side by at least three 2'-O methyl RNA residues. In yet another embodiment, the antisense nucleic acid is a ribozyme.

In a second aspect, the invention features a method of enhancing apoptosis in a cell, involving administering to the cell a negative regulator of the IAP-dependent antiapoptotic pathway. In preferred embodiments the negative regulator is an antisense IAP nucleic acid, an antibody that specifically binds an IAP polypeptide, an IAP polypeptide comprising a ring zinc finger, said polypeptide having no more than two BIR domains, a nucleic acid encoding the ring zinc finger domain of an IAP polypeptide, or a compound that prevents cleavage of the IAP polypeptide.

In preferred embodiments of the second aspect of the invention, the cell is in a mammal diagnosed with a proliferative disease, for example, cancer, The cell may comprises a mucosa-associated lymphoid tissue (MALT), a tissue in which the IAP gene HIAP1 is frequently involved in a translocation, resulting in marginal zone cell lymphomas. The cell may also be a breast cancer cell, where increased HIAP1 expression is known to correlate with tumor progression. The cell may also be a cell in which NFkB expression or activity is increased, for example, cell of head and neck carcinomas, adult T-cell lymphomas, nasopharyngeal carcinomas, and Hodgkin's disease. The cell may also be an acute myelogenous leukemia cell, where increased XIAP levels correlate with poor patient prognosis. In addition, the cell may be a small cell lung carcinoma cell, where increased levels of XIAP correlates with increased resistance to radiation treatment.

In preferred embodiments of the second aspect of the invention, the IAP is XIAP, HIAP1, or HIAP2. Preferably the antisense nucleic acid is mammalian, for example, mouse or human. In still other preferred embodiments, the XIAP antisense is chosen from any one of SEQ ID NOS: 1 through 96, and the HIAP1 antisense is chosen from any one of SEQ ID NOS: 97 through 194.

In still other embodiments of the second aspect of the invention, the antisense nucleic acid comprises at least one modified internucleoside linkage. Preferably the modified internucleoside linkage is a phosphorothioate, a methylphosphonate, a phosphotriester, a phosphorodithioate, or a phosphoselenate linkage. In addition, the antisense nucleic acid may comprise at least one modified sugar moiety. Preferably this modified sugar moiety is a 2'-O methoxyethyl group or a 2'-O methyl group. In still another preferred embodiment, the antisense nucleic acid is a chimeric nucleic acid. Preferably the chimeric nucleic acid comprises DNA residues linked together by phosphorothioate linkages, and the DNA residues are flanked on each side by at least one 2'-O methyl RNA residue linked together by a phosphorothioate linkage. More preferably the DNA residues are flanked on each side by at least three 2'-O methyl RNA residues. In still further embodiments, administration of the antisense nucleic acid sensitizes the cell to chemotherapy or radiotherapy. In addition, the cell may be in vitro or in vivo.

In a third aspect, the invention features a pharmaceutical composition comprising a mammalian IAP antisense nucleic acid. In one preferred embodiment, the mammalian antisense IAP nucleic acid is a human antisense nucleic acid. Preferably the antisense nucleic acid binds a target sequence of the human XIAP gene or mRNA, the human HIAP1 gene or mRNA, the human HIAP2 gene or mRNA, the murine XIAP gene or mRNA, the murine HIAP1 gene or mRNA, or the murine HIAP2 gene or mRNA. More preferably the composition comprises an antisense nucleic acid chosen from any one of SEQ ID NOS: 1 through 96 (XIAP) or SEQ ID NOS: 97 through 194 (HIAP1).

In another aspect, the invention features an IAP gene nucleic acid fragment or antisense RNA sequence for use in suppressing cell proliferation. Such nucleic acids of the invention and methods for using them may be identified according to a method involving: (a) providing a cell sample; (b) introducing by transformation into the cell sample a candidate IAP nucleic acid; (c) expressing the candidate IAP nucleic acid within the cell sample; and (d) determining whether the cell sample exhibits an altered apoptotic response, whereby decreased apoptosis identifies an anti-proliferative compound. Preferably the cell is a cancer cell.

In another aspect, the invention features a method of treating a patient diagnosed with a proliferative disease. In the method, apoptosis may be induced in a cell to control a proliferative disease either alone or in combination with other therapies by administering to the cell a negative regulator of the IAP-dependent or anti-apoptotic pathway. The negative regulator may be, but is not limited to, an IAP ring zinc finger, and an IAP polypeptide that includes a ring zinc finger and lacks at least one BIR domain. Alternatively, apoptosis may be induced in the cell by administering a nucleic acid encoding an IAP antisense RNA molecule administered directly or via gene therapy (see U.S. Pat. No. 5,576,208 for general parameters that may be applicable in the selection of IAP antisense RNAs). In yet another method, the negative regulator may be a purified antibody, or a fragment thereof, that binds specifically to an IAP polypeptide. For example, in one preferred embodiment, the antibody may bind to an approximately 26 kDa cleavage product of an IAP polypeptide that includes at least one BIR domain but lacks a ring zinc finger domain.

In two additional aspects, the invention features a transgenic animal and methods of using the mammal for detection of anti-cancer therapeutics. Preferably the mammal overexpresses an IAP polypeptide and/or expresses an IAP antisense RNA or IAP fragment. In one embodiment, the animal also has a genetic predisposition to cancer or has cancer cells under conditions that provide for proliferation absent the transgenic construct encoding either the antisense RNA or fragment.

"Protein" or "polypeptide" or "polypeptide fragment" means any chain of more than two amino acids, regardless of post-translational modification (e.g., glycosylation or phosphorylation), constituting all or part of a naturally-occurring polypeptide or peptide, or constituting a non-naturally occurring polypeptide or peptide.

"Apoptosis" means the process of cell death wherein a dying cell displays a set of well-characterized biochemical hallmarks that include cell membrane blebbing, cell soma shrinkage, chromatin condensation, and DNA laddering. Cells that die by apoptosis include neurons (e.g., during the course of neurodegenerative diseases such as stroke, Parkinson's disease, and Alzheimer's disease), cardiomyocytes (e.g., after myocardial infarction or over the course of congestive heart failure), and cancer cells (e.g., after exposure to radiation or chemotherapeutic agents). Environmental stress (e.g., hypoxic stress) that is not alleviated may cause a cell to enter the early phase of the apoptotic pathway, which is reversible (i.e., cells at the early stage of the apoptotic pathway can be rescued). At a later phase of apoptosis (the commitment phase), cells cannot be rescued, and, as a result, are committed to die.

Proteins and compounds known to stimulate and inhibit apoptosis in a diverse variety of cells are well known in the art. For example, intracellular expression and activation of the caspase (ICE) family induces or stimulates apoptotic cell death, whereas expression of the IAPs or some members of the Bcl-2 family inhibits apoptotic cell death. In addition, there are survival factors that inhibit cell death in specific cell types. For example, neurotrophic factors, such as NGF inhibit neuronal apoptosis.

In some situations it may be desirable to artificially stimulate or inhibit apoptotic cell death by gene therapy or by a compound that mimics a gene therapeutic effect. For example, a cell that is susceptible to apoptosis induced by disease or environmental stress may be made more resistant to apoptosis by introducing an expression vector encoding an anti-apoptotic protein (such as an IAP, a Bcl-2 family member, or a neurotrophin) into the cell. Conversely, a cancer cell may be made less resistant to apoptosis by introducing into it an expression vector encoding a pro-apoptotic protein (such as a caspase) or by introducing into it an antisense nucleic acid, for example, an IAP antisense nucleic acid, regardless of its length. In addition, placement of the encoded protein of interest under the translational regulation of a XIAP IRES ensures that copious quantities of the protein are produced, especially under cellular conditions during which most protein translation (i.e., cap-dependent protein translation) is down-regulated, e.g., when a cell is under environmental stress, and when a cell is at a threshold for entering the apoptotic pathway.

By "IAP gene" is meant a gene encoding a polypeptide having at least one BIR domain and a ring zinc finger domain that is capable of modulating (inhibiting or enhancing) apoptosis in a cell or tissue when provided by other intracellular or extracellular delivery methods (see, e.g., U.S. Pat. No. 5,919,912, U.S. Ser. No. 08/576,965, and PCT/IB96/01022). In preferred embodiments, the IAP gene is a gene having about 50% or greater nucleotide sequence identity to at least one of the IAP amino acid encoding sequences of FIGS. 1 through 6, or portions thereof. Preferably the region of sequence over which identity is measured is a region encoding at least one BIR domain and a ring zinc finger domain. Mammalian IAP genes include nucleotide sequences isolated from any mammalian source. Preferably the mammal is a human.

The term "IAP gene" is meant to encompass any member of the family of genes that encode inhibitors of apoptosis. An IAP gene may encode a polypeptide that has at least 20%, preferably at least 30%, and most preferably at least 50% amino acid sequence identity with at least one of the conserved regions of one of the IAP members described herein (i.e., either the BIR or ring zinc finger domains from human or murine XIAP, HIAP1, and HIAP2). Representative members of the IAP gene family include, without limitation, the human and murine XIAP, HIAP1, and HIAP2 genes.

By "IAP protein" or "IAP polypeptide" is meant a polypeptide, or fragment thereof, encoded by an IAP gene.

By "BIR domain" is meant a domain having the amino acid sequence of the consensus sequence: Xaa1-Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa1-Xaa1-Xaa1-Xaa1-Pro-Xaa1-Cys-Xaa1-Phe-Val, wherein Xaa1 is any amino acid and Xaa2 is any amino acid or is absent (SEQ ID NO: 216). Preferably the sequence is substantially identical to one of the BIR domain sequences provided for XIAP, HIAP 1, or HIAP2 herein.

By "ring zinc finger" or "RZF" is meant a domain having the amino acid sequence of the consensus sequence: Glu-Xaa1-Xaa1-Xaa1-Xaa1-Xaa1-Xaa1-Xaa2-Xaa1-Xaa1-Xaa1-Cys-Lys-Xaa3-Cys-Met-Xaa1-Xaa1-Xaa1-Xaa1-Xaa1-Xaa3-Xaa1-Phe-Xaa1-Pro-Cys-Gly-His-Xaa1-Xaa1-Xaa1-Cys-Xaa1-Xaa1-Cys-Ala-Xaa1-Xaa1-Xaa1-Xaa1-Xaa1-Cys-Pro-Xaa1-Cys, wherein Xaa1 is any amino acid, Xaa2 is Glu or Asp, and Xaa3 is Val or Ile (SEQ ID NO: 217).

Preferably the sequence is substantially identical to the RZF domains provided in U.S. Ser. No. 08/800,929, incorporated herein by reference, for the human or murine XIAP, HIAP1, or HIAP2.

By "enhancing apoptosis" is meant increasing the number of cells that apoptose in a given cell population. Preferably the cell population is selected from a group including ovarian cancer cells, breast cancer cells, pancreatic cancer cells, T cells, neuronal cells, fibroblasts, or any other cell line known to proliferate in a laboratory setting. It will be appreciated that the degree of apoptosis enhancement provided by an apoptosis-enhancing compound in a given assay will vary, but that one skilled in the art can determine the statistically significant change in the level of apoptosis that identifies a compound that enhances apoptosis otherwise limited by an IAP. Preferably "enhancing apoptosis" means that the increase in the number of cells undergoing apoptosis is at least 25%, more preferably the increase is 50%, and most preferably the increase is at least one-fold. Preferably the sample monitored is a sample of cells that normally undergo insufficient apoptosis (i.e., cancer cells). Methods for detecting a changes in the level of apoptosis (i.e., enhancement or reduction) are described herein.

By "proliferative disease" is meant a disease that is caused by or results in inappropriately high levels of cell division, inappropriately low levels of apoptosis, or both. For example, cancers such as lymphoma, leukemia, melanoma, ovarian cancer, breast cancer, pancreatic cancer, and lung cancer are all examples of proliferative disease.

By "IAP biological activity" is meant any activity known to be caused in vivo or in vitro by an IAP polypeptide.

By "transformed cell" is meant a cell into which (or into an ancestor of which) has been introduced, by means of recombinant DNA techniques, a DNA molecule encoding (as used herein) an IAP polypeptide.

By "transgene" is meant any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene homologous to an endogenous gene of the organism.

By "transgenic" is meant any cell that includes a DNA sequence that is inserted by artifice into a cell and becomes part of the genome of the organism that develops from that cell. As used herein, the transgenic organisms are generally transgenic mammals (e.g., rodents, such as rats or mice) and the DNA (transgene) is inserted by artifice into the nuclear genome.

By "transformation" is meant any method for introducing foreign molecules, for example, an antisense nucleic acid, into a cell. Lipofection, calcium phosphate precipitation, retroviral delivery, electroporation, biolistic transformation, and penetratin are just a few of the teachings that may be used. For example, biolistic transformation is a method for introducing foreign molecules into a cell using velocity driven microprojectiles such as tungsten or gold particles. Such velocity-driven methods originate from pressure bursts that include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells. In another example, a foreign molecule (e.g., an antisense nucleic acid) can be translocated into a cell using the penetratin system as described, for example, by Prochiantz (Nature Biotechnology 16:819–820, 1998; and Derossi et al. (Trends Cell Biol. 8: 84–87, 1998). In this system a penetratin peptide contains a transduction sequence that carries the peptide and a conjugated partner, for example, a phosphorothioate antisense nucleic acid (that is cross-linked through a disulfide bridge to the peptide) across the plasma membrane into the cell. The disulfide band is reduced inside the cell, releasing the partner.

By "antisense," as used herein in reference to nucleic acids, is meant a nucleic acid sequence, regardless of length, that is complementary to the coding strand or mRNA of an IAP gene. Preferably the antisense nucleic acid is capable of enhancing apoptosis when present in a cell that normally does not undergo sufficient apoptosis. Preferably the increase is at least 10%, relative to a control, more preferably 25%, and most preferably 1-fold or more. Preferably an IAP antisense nucleic acid comprises from about 8 to 30 nucleotides. An IAP antisense nucleic acid may also contain at least 40, 60, 85, 120, or more consecutive nucleotides that are complementary to a IAP mRNA or DNA, and may be as long as a full-length IAP gene or mRNA. The antisense nucleic acid may contain a modified backbone, for example, phosphorothioate, phosphorodithioate, or other modified backbones known in the art, or may contain non-natural internucleoside linkages.

By "ribozyme" is meant an RNA that has enzymatic activity, possessing site specificity and cleavage capability for a target RNA molecule. Ribozymes can be used to decrease expression of a polypeptide. Methods for using ribozymes to decrease polypeptide expression are described, for example, by Turner et al., (Adv. Exp. Med. Biol. 465:303–318, 2000) and Norris et al., (Adv. Exp. Med. Biol. 465:293–301, 2000).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably the polypeptide is an IAP polypeptide that is at least 75%), more preferably at least 90%, and most preferably at least 99%, by weight, pure. A substantially pure IAP polypeptide may be obtained, for example, by extraction from a natural source (e.g., a fibroblast, neuronal cell, or lymphocyte) by expression of a recombinant nucleic acid encoding an IAP polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes that, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes a recombinant DNA that is part of a hybrid gene encoding additional polypeptide sequence.

By "positioned for expression" is meant that the DNA molecule is positioned adjacent to a DNA sequence, that directs transcription and translation of the sequence (i.e., facilitates the production of, e.g., an IAP polypeptide, a recombinant protein or an RNA molecule).

By "reporter gene" is meant a gene whose expression may be assayed; such genes include, without limitation, glucuronidase (GUS), luciferase, chloramphenicol transacetylase (CAT), and Beta-galactosidase.

By "promoter" is meant a minimal sequence sufficient to direct transcription. Also included in the invention are those promoter elements that are sufficient to render promoter-dependent gene expression controllable for cell type-specific, tissue-specific or that are inducible by external signals or agents; such elements may be located in the 5' or 3' regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "conserved region" is meant any stretch of six or more contiguous amino acids exhibiting at least 30%, preferably 50%, and most preferably 70% amino acid sequence identity between two or more of the IAP family members, (e.g., between human HIAP1, HIAP2, and XIAP). Examples of preferred conserved regions include, without limitation, BIR domains and ring zinc finger domains.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labeling or fluorescein labelling).

By "purified antibody" is meant an antibody that is at least 60%, by weight, free from proteins and naturally occurring organic molecules with which it is naturally associated. Preferably the preparation is at least 75, more preferably 90%, and most preferably at least 99%, by weight, antibody, e.g., an IAP-specific antibody. A purified antibody may be obtained, for example, by affinity chromatography using recombinantly-produced protein or conserved motif peptides and standard techniques.

By "specifically binds" is meant an antibody that recognizes and binds a protein but that does not substantially recognize and bind other molecules in a sample, e.g., a biological sample, that naturally includes protein.

Other features and advantages of the invention will be apparent from the following description of the preferred embodiments thereof, and from the claims.

BRIEF DESCRIPTION OF THE DRAWINGS

FIG. 1 is the human XIAP cDNA sequence (SEQ ID NO: 218) and the XIAP polypeptide sequence (SEQ ID NO: 219).

FIG. 2 is the human HIAP1 cDNA sequence (SEQ ID NO: 220) and the HIAP1 polypeptide sequence (SEQ ID NO: 221).

FIG. 3 is the human HIAP2 cDNA sequence (SEQ ID NO: 222) and the HIAP2 polypeptide sequence (SEQ ID NO: 223). The sequence absent in the HIAP2 variant is boxed.

FIG. 4 is the murine XIAP (also referred to as "miap-3") cDNA sequence (SEQ ID NO: 224) and encoded murine XIAP polypeptide sequence (SEQ ID NO: 225).

FIG. 5 is the murine HIAP1 (also referred to as "miap-1") cDNA sequence (SEQ ID NO: 226) and the encoded murine HIAP1 polypeptide sequence (SEQ ID NO: 227).

FIG. 6 is the murine HIAP2 (also referred to as "miap-2") cDNA sequence (SEQ ID NO: 228) and the encoded murine HIAP2 polypeptide (SEQ ID NO: 229).

FIGS. 7B, 7D, 7F, 7H, 7J, and 7L are the total protein concentration values for each oligonucleotide transfection compared to mock transfection results that were used to normalize the above XIAP protein results.

FIG. 8C is a graph of the total protein concentration values for each oligonucleotide transfection compared to mock transfection results, which were used to normalize the XIAP protein results shown in FIG. 8B.

FIGS. 9A through 9D are graphs of the effects of antisense XIAP oligonucleotides on cell viability (FIGS. 9A, 9C, and 9D), and chemosensitization in the presence of adriamycin (FIG. 9B).

FIG. 15 is the human XIAP sequence containing a 5'UTR, the coding region, and a 3'UTR (SEQ ID NO: 230).

FIG. 16 is the human XIAP sequence containing a 5'UTR, the coding region, and a 3'UTR (SEQ ID NO: 231).

DETAILED DESCRIPTION OF THE INVENTION

Figures 7A, 7B:
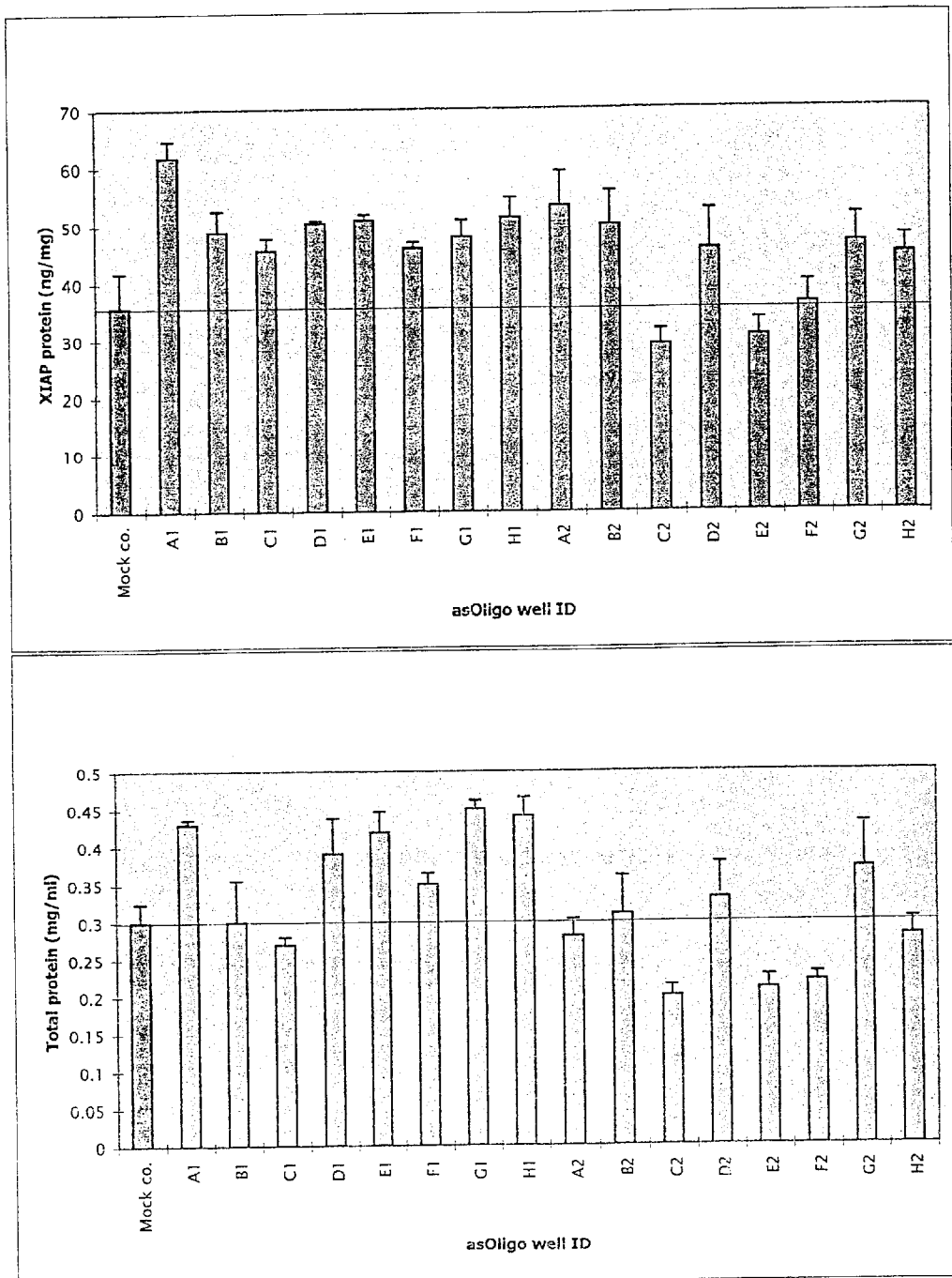
FIGS. 7A through 7L are graphs showing the effect of antisense XIAP oligonucleotides on XIAP protein expression, relative to total protein (FIGS. 7A, 7C, 7E, 7G, 7I, and 7K).
Figures 7C, 7D:
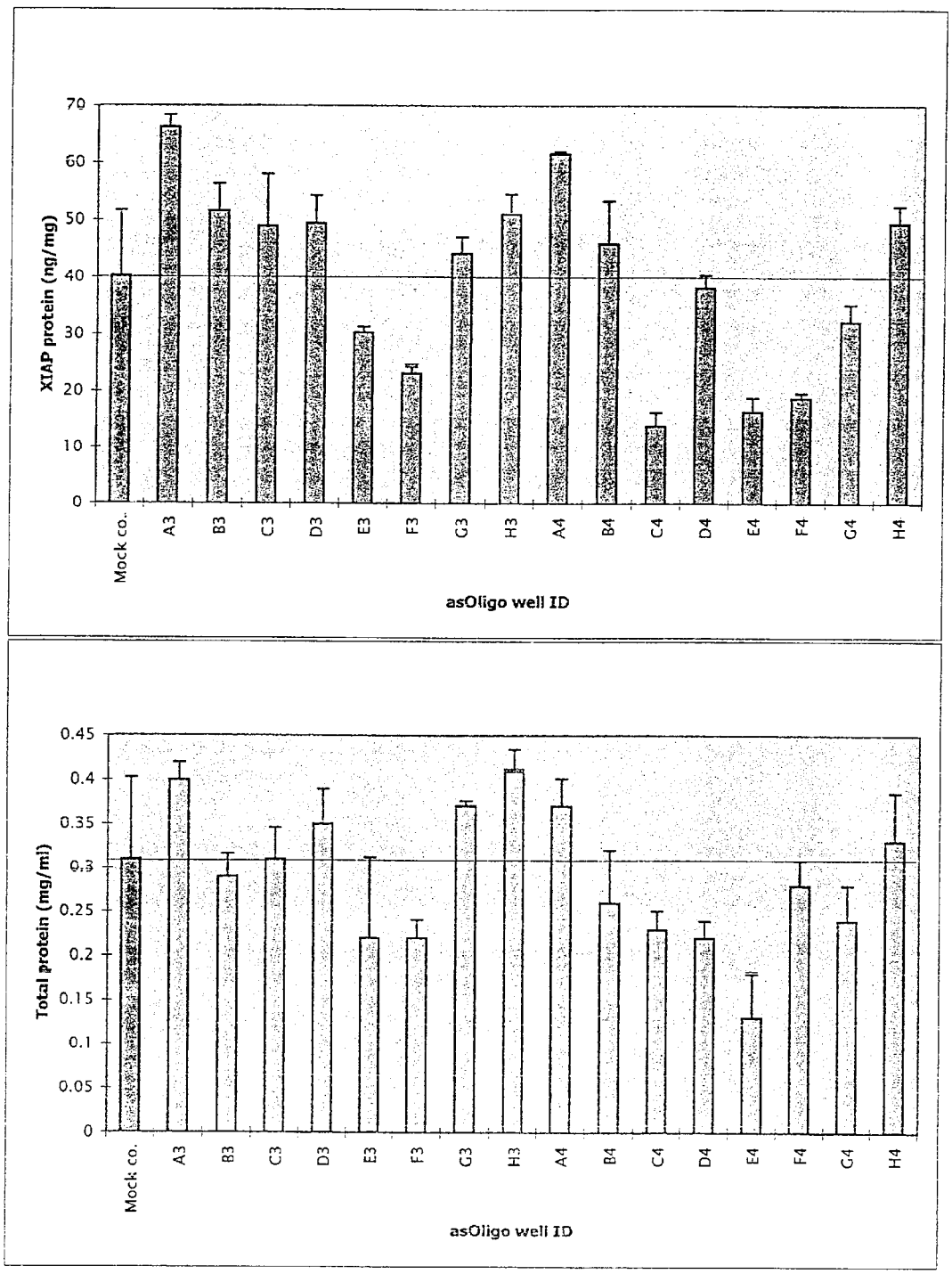
Figures 7E, 7F:
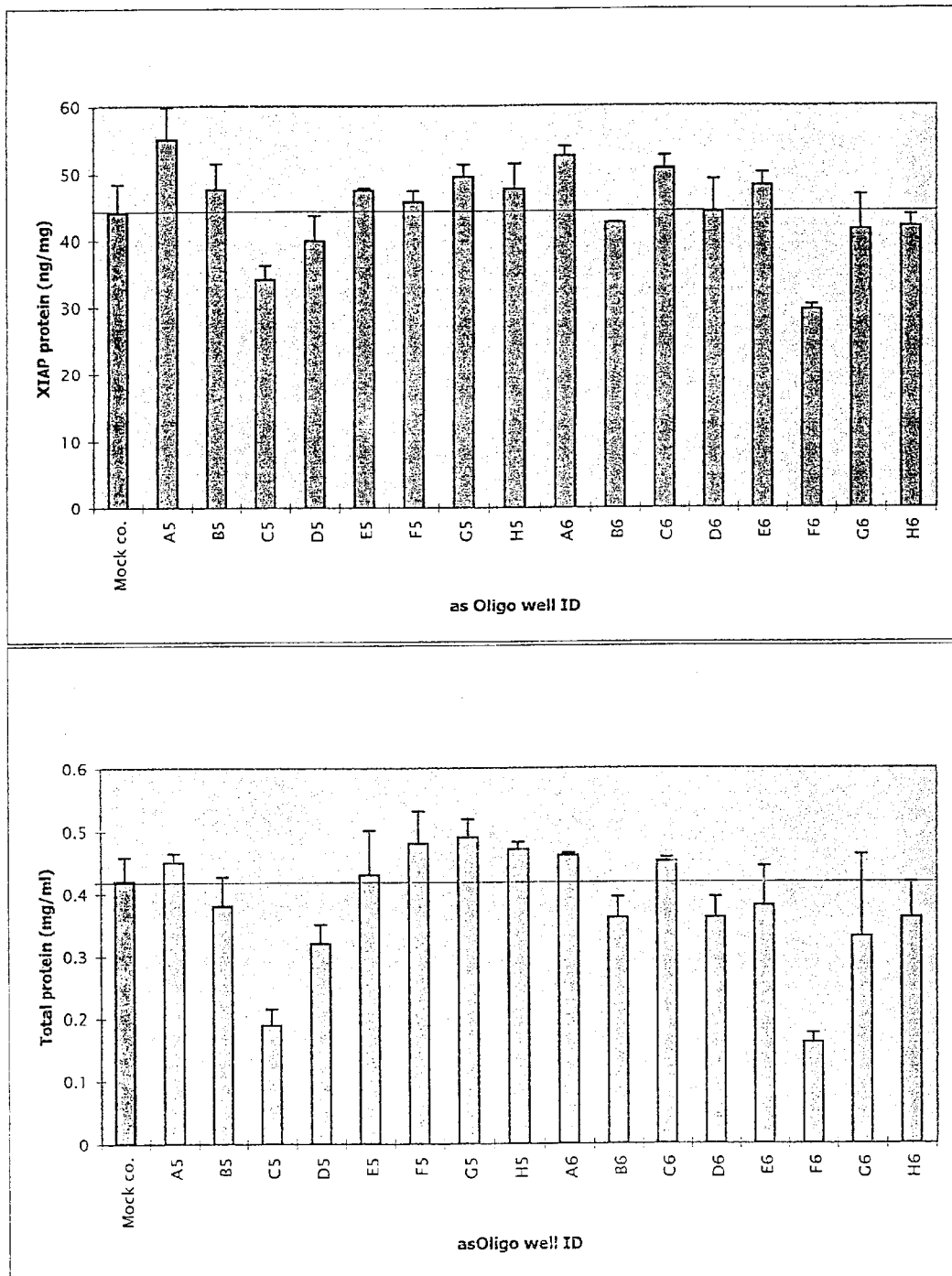
Figures 7G, 7H:
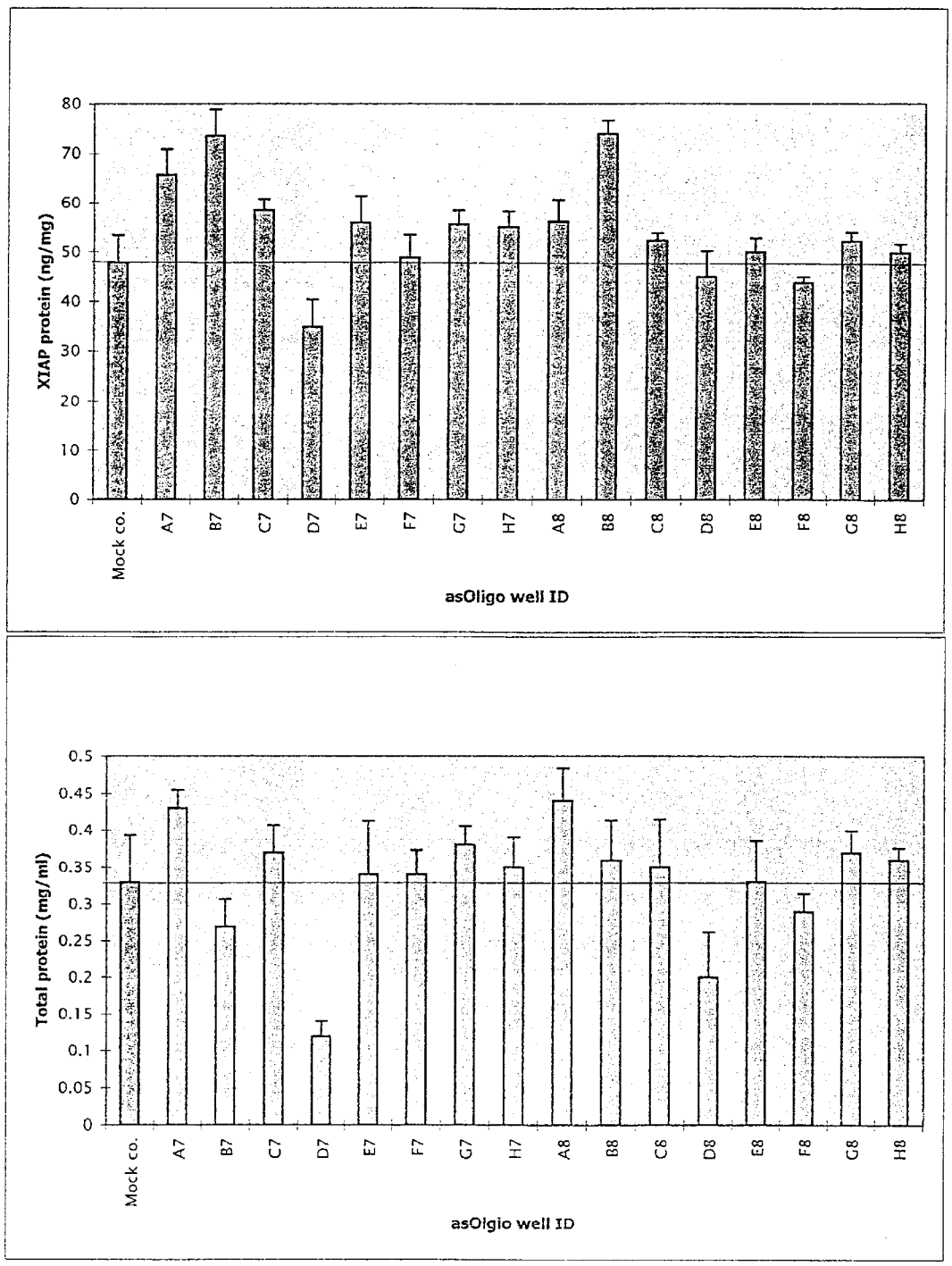
Figure 7I:
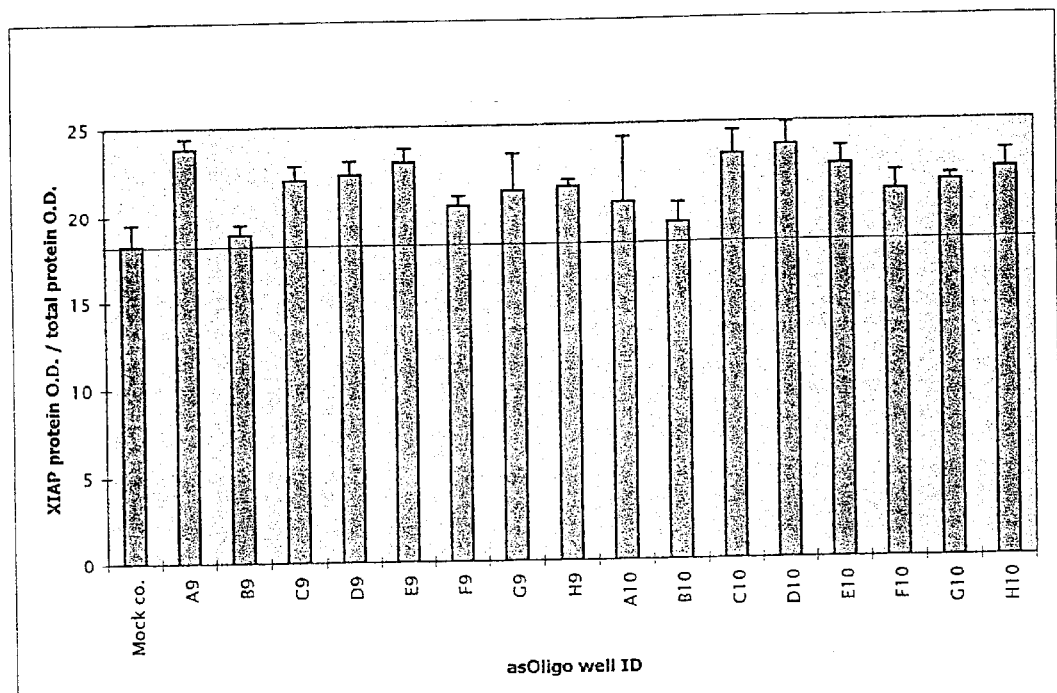
Figure 7J:
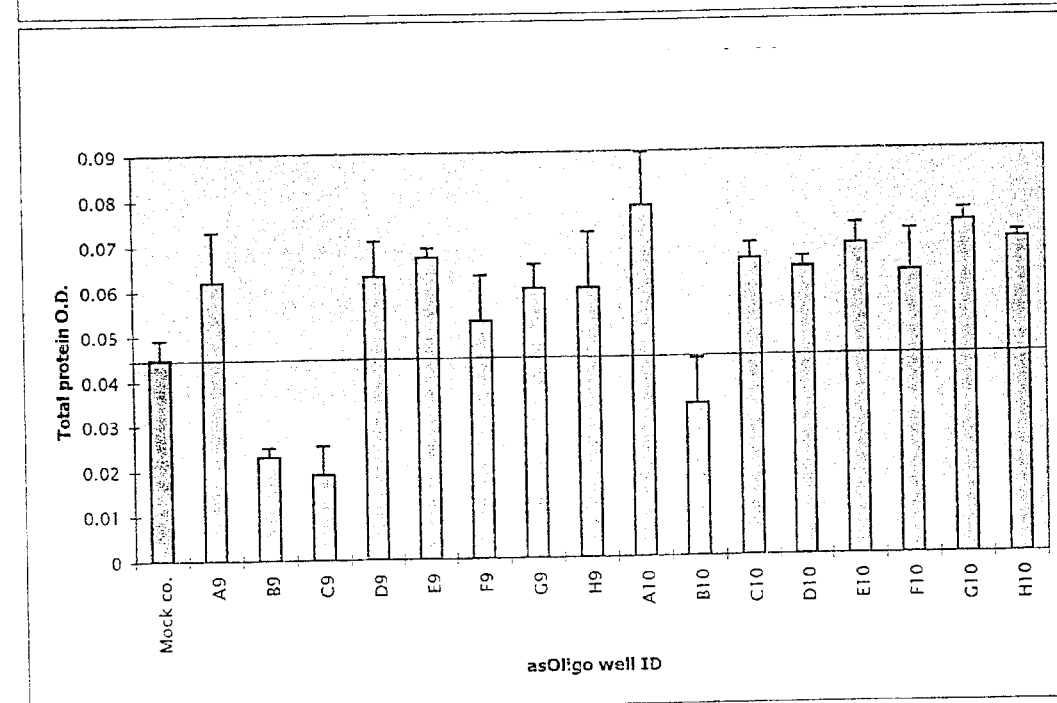
Figure 7K:
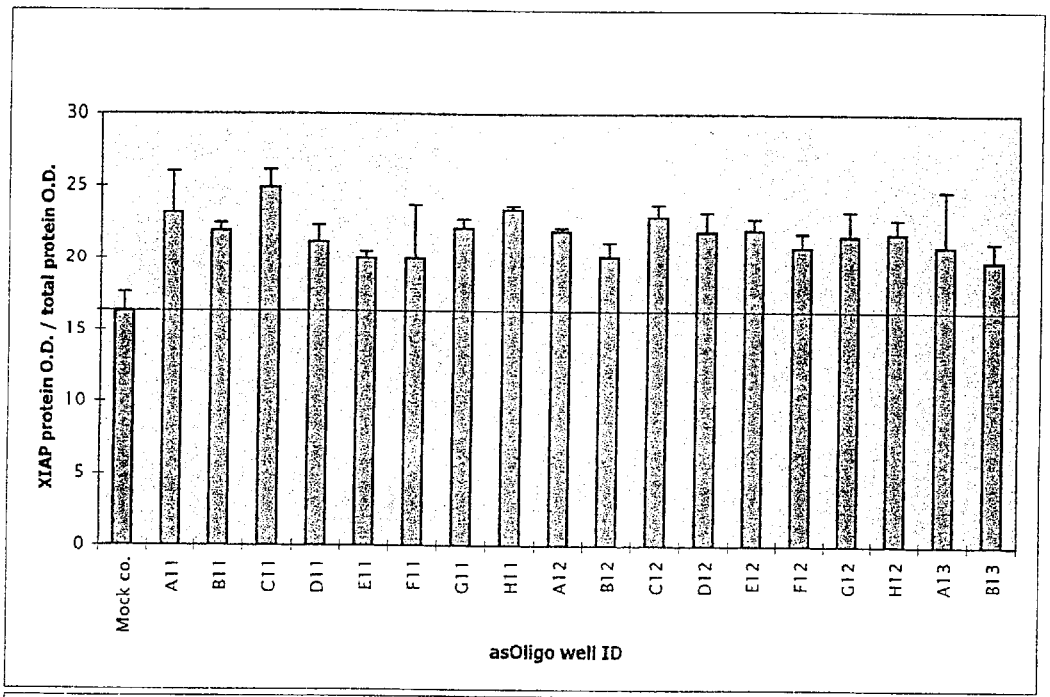
Figure 7L:
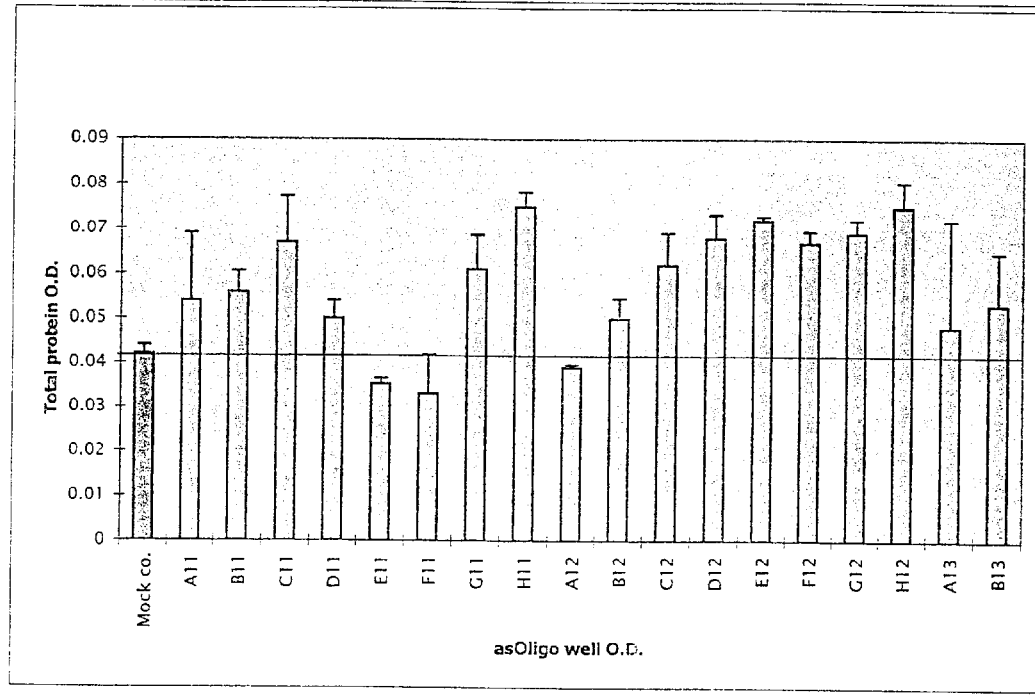

The present invention provides IAP antisense nucleic acid sequences that inhibit IAP biological activity, regardless of length, and methods for using them to induce apoptosis in a cell. The antisense nucleic acids of the present invention may also be used to form pharmaceutical compositions. The invention also features methods for enhancing apoptosis in a cell by administering a negative regulator of the IAP anti-apoptotic pathway other than antisense. Such negative regulators include, for example, an IAP polypeptide comprising a ring zinc finger having no more than two BIR domains, and a compound that prevents cleavage of an IAP polypeptide. Such negative regulators may also be used to form a pharmaceutical composition. These pharmaceutical compositions may be used to treat, ameliorate, improve, sustain, or prevent a proliferative disease, for example, cancer, or a symptom of a proliferative disease.

Administration

An IAP antisense nucleic acid, or other negative regulator of the IAP anti-apoptotic pathway may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

If desired, treatment with an IAP antisense nucleic acid, IAP fragments, or other negative regulator of the anti-apoptotic pathway may be combined with more traditional therapies for the proliferative disease such as surgery or chemotherapy.

For any of the methods of application described above, the therapeutic antisense IAP nucleic acid or other negative regulator of the IAP anti-apoptotic pathway is preferably applied to the site of the needed apoptosis event (for example, by injection). However, it may also be applied to tissue in the vicinity of the predicted apoptosis event or to a blood vessel supplying the cells predicted to require enhanced apoptosis.

The dosage of an antisense IAP nucleic acid, or a negative regulator of the IAP anti-apoptotic pathway, for example, an IAP fragment, IAP mutant protein or an IAP antibody depends on a number of factors, including the size and health of the individual patient, but, generally, between 0.1 mg and 100 mg inclusive are administered per day to an adult in any pharmaceutically acceptable formulation. In addition, treatment by any IAP-modulating gene therapy approach may be combined with more traditional therapies.

Antisense Therapy

Anti-cancer therapy may be accomplished by direct administration of a therapeutic antisense IAP nucleic acid to a cell that is expected to require enhanced apoptosis. The antisense nucleic acid may be produced and isolated by any one of many standard techniques. Administration of IAP antisense nucleic acids to malignant cells can be carried out by any of the methods for direct nucleic acid administration, as described herein.

Retroviral vectors, adenoviral vectors, adeno-associated viral vectors, or other viral vectors with the appropriate tropism for cells likely requiring enhanced apoptosis (for example, breast cancer and ovarian cancer cells) may be used as a gene transfer delivery system for a therapeutic antisense IAP gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; Miller et al., BioTechniques 7:980–990, 1989; Le Gal La Salle et al., Science 259:988–990, 1993; and Johnson, Chest 107:77S–83S, 1995).

Retroviral vectors are particularly well developed and have been used in clinical settings (Rosenberg et al., N. Engl. J. Med 323:370, 1990; Anderson et al., U.S. Pat. No. 5,399,346). Non-viral approaches may also be employed for the introduction of therapeutic DNA into cells otherwise predicted to undergo apoptosis. For example, IAPs may be introduced into a cell by lipofection (Feigner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enz. 101:512, 1983), the penetratin system (Allinquant et al., J. Cell Biol. 128:919–927, 1995; Prochiantz, Curr. Opin. Neurobiol. 6:629–634, 1996), asialorosonucoid-polylysine conjugation (Wu et al., J. Biol. Chem. 263:14621, 1988; Wu et al., J. Biol. Chem. 264:16985, 1989); or, less preferably microinjection under surgical conditions (Wolff et al., Science 247:1465, 1990).

In the therapeutic nucleic acid constructs described, nucleic acid expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in ovarian cells, breast tissue, neural cells, T cells, or B cells may be used to direct expression. Enhancers include, without limitation, those that are characterized as tissue- or cell-specific in their expression. Alternatively, if a clone is used as a therapeutic construct, regulation may be mediated by the cognate regulatory sequences or, if desired, by regulatory sequences derived from a heterologous source, including any of the promoters or regulatory elements described above.

Therapeutic Products

For IAP related therapies one may employ the paradigms utilized for Bcl-2 and Ras antisense development, although accommodation of an IAP mutation is not required (in contrast to Ras antisense). Most useful are antisense constructs that enhance apoptosis at least 10%, preferably by enhancing degradation of the RNA in the nucleus.

Manipulation of Cancer Chemotherapeutic Drug Resistance Using an Antisense Oligonucleotide and Fragment Approaches We have documented that overexpression of the IAPs renders cell lines resistant to serum growth factor withdrawal, tumor necrosis factor alpha (TNF) and menadione exposure, all of which are treatments that normally induce apoptosis. Herein, we describe the extension of these studies to cancer cell lines using apoptotic triggers used in clinical situations, such as doxorubicin, adriamycin, and methotrexate. Our findings have led up to the design of antisense RNA therapeutics. Rapid screening of multiple cell lines for apoptotic response has been made feasible through the generation of a series of sense and antisense adenoviral IAP and expression vectors, as well as control lacZ viruses. One may now show enhanced drug resistance using the expression constructs. In addition, anti-sense adenovirus constructs may be developed and used to test reversal of the drug resistant phenotype of appropriate cell lines. We have designed a series of antisense oligonucleotides to various regions of each of the iaps. These oligonucleotides may be used to enhance drug sensitivity after testing in an assay system, i.e., with the adenoviral vectors system. Animal modeling of the effectiveness of antisense IAP oligonucleotides may also be employed as a step in testing and appropriate transgenic mammals for this are described in U.S. Ser. No. 08/800,929, incorporated herein by reference, and are also generally available in the art.

Characterization of IAP Activity and Intracellular Localization Studies

The ability of IAPs to modulate apoptosis can be defined in vitro systems in which alterations of apoptosis can be detected. Mammalian expression constructs carrying IAP cDNAs, which are either full-length, truncated, or antisense constructs can be introduced into cell lines, such as CHO, NIH 3T3, HL60, Rat-1, or Jurkat cells. In addition, SF21 insect cells may be used, in which case the IAP gene is preferentially expressed using an insect heat shock promoter. Following transfection, apoptosis can be induced by standard methods, which include serum withdrawal, or application of staurosporine, menadione (which induces apoptosis via free radial formation), or anti-Fas antibodies. As a control, cells are cultured under the same conditions as those induced to undergo apoptosis, but either not transfected, or transfected with a vector that lacks an IAP insert. The ability of each IAP related construct to inhibit or enhance apoptosis upon expression can be quantified by calculating the survival index of the cells, i.e., the ratio of surviving transfected cells to surviving control cells. These experiments can confirm the presence of apoptosis inhibiting activity and, as discussed below, can also be used to determine the functional region(s) of an IAP that may be employed to achieve enhancement of apoptosis. These assays may also be performed in combination with the application of additional compounds in order to identify compounds that enhance apoptosis via IAP expression.

Apoptosis Assays

Specific examples of apoptosis assays are provided in the following references. Assays for apoptosis in lymphocytes are disclosed by: Li et al., "Induction of apoptosis in uninfected lymphocytes by HIV-1 Tat protein", Science 268:429–431, 1995; Gibellini et al., "Tat-expressing Jurkat cells show an increased resistance to different apoptotic stimuli, including acute human immunodeficiency virus-type 1 (HIV-1) infection", Br. J. Haematol. 89:24–33, 1995; Martin et al., "HIV-1 infection of human CD4$^+$ T cells in vitro. Differential induction of apoptosis in these cells." J. Immunol. 152:330–342, 1994; Terai et al., "Apoptosis as a mechanism of cell death in cultured T lymphoblasts acutely infected with HIV-1", J. Clin. Invest. 87:1710–1715, 1991; Dhein et al., "Autocrine T-cell suicide mediated by APO-1/(Fas/CD95)", Nature 373:438–441, 1995; Katsikis et al., "Fas antigen stimulation induces marked apoptosis of T lymphocytes in human immunodeficiency virus-infected individuals", J. Exp. Med. 1815:2029–2036, 1995; Westendorp et al., "Sensitization of T cells to CD95-mediated apoptosis by HIV-1 Tat and gp120", Nature 375:497, 1995; and DeRossi et al., Virology 198:234–44, 1994.

Assays for apoptosis in fibroblasts are disclosed by: Vossbeck et al., "Direct transforming activity of TGF-beta on rat fibroblasts", Int. J. Cancer 61:92–97, 1995; Goruppi et al., "Dissection of c-myc domains involved in S phase induction of NIH3T3 fibroblasts", Oncogene 9:1537–1544, 1994; Fernandez et al., "Differential sensitivity of normal and Ha-ras transformed C3H mouse embryo fibroblasts to tumor necrosis factor: induction of bcl-2, c-myc, and manganese superoxide dismutase in resistant cells", Oncogene 9:2009–2017, 1994; Harrington et al., "c-Myc-induced apoptosis in fibroblasts is inhibited by specific cytokines", EMBO J., 13:3286–3295, 1994; and Itoh et al., "A novel protein domain required for apoptosis. Mutational analysis of human Fas antigen", J. Biol. Chem. 268:10932–10937, 1993.

Assays for apoptosis in neuronal cells are disclosed by: Melino et al., "Tissue transglutaminase and apoptosis: sense and antisense transfection studies with human neuroblastoma cells", Mol. Cell. Biol. 14:6584–6596, 1994; Rosenbaum et al., "Evidence for hypoxia-induced, programmed cell death of cultured neurons", Ann. Neurol. 36:864–870, 1994; Sato et al., "Neuronal differentiation of PC12 cells as a result of prevention of cell death by bcl-2", J. Neurobiol. 25:1227–1234, 1994; Ferrari et al., "N-acetylcysteine D- and L-stereoisomers prevents apoptotic death of neuronal cells", J. Neurosci. 1516:2857–2866, 1995; Talley et al., "Tumor necrosis factor alpha-induced apoptosis in human neuronal cells: protection by the antioxidant N-acetylcysteine and the genes bcl-2 and crmA", Mol. Cell Biol. 1585:2359–2366, 1995; and Walkinshaw et al., "Induction of apoptosis in catecholaminergic PC12 cells by L-DOPA. Implications for the treatment of Parkinson's disease.", J. Clin. Invest. 95:2458–2464, 1995.

Assays for apoptosis in insect cells are disclosed by: Clem et al., "Prevention of apoptosis by a baculovirus gene during infection of insect cells", Science 254:1388–1390, 1991; Crook et al., "An apoptosis-inhibiting baculovirus gene with a zinc finger-like motif", J. Virol. 67:2168–2174, 1993; Rabizadeh et al., "Expression of the baculovirus p35 gene inhibits mammalian neural cell death", J. Neurochem. 61:2318–2321, 1993; Birnbaum et al., "An apoptosis inhibiting gene from a nuclear polyhedrosis virus encoding a polypeptide with Cys/His sequence motifs", J. Virol. 68:2521–2528, 1994; and Clem et al., "Control of programmed cell death by the baculovirus genes p35 and IAP", Mol. Cell. Biol. 14:5212–5222, 1994.

The following examples are to illustrate the invention. They are not meant to limit the invention in any way.

EXAMPLE 1

Testing of Antisense Oligonucleotides

1. Complete panel of adenovirus constructs. The panel may consist of approximately four types of recombinant virus. A) Sense orientation viruses for each of the IAP open reading frames. These viruses are designed to massively overexpress the recombinant protein in infected cells. XIAP, HIAP1, HIAP2, and NAIP. B) Antisense orientation viruses in which the viral promoter drives the synthesis of an mRNA of opposite polarity to the iap mRNA, thereby shutting off host cell synthesis of the targeted protein coding region. XIAP, HIAP1, HIAP2, and NAIP "antisense" constructs are used for production of such antisense IAPs. C) Sub-domain expression viruses. These constructs express only a partial IAP protein in infected cells. We have data indicating that deletion of the zinc finger of XIAP renders the protein more potent in protecting cell against apoptotic triggers. This data also indicates that expression of the zinc finger alone will indicate apoptosis by functioning as a dominant-negative repressor of XIAP function. XIAP-ZF and XIAP-BIR viruses are required. D) Control viruses. Functional analysis of the IAPs requires suitable positive and negative controls for comparison. Bcl-2 sense, Bcl-2 antisense, p53 sense, and Lac Z (negative control) viruses may be utilized.

2. Confirmation of recombinant adenovirus function. Verification of the sense adenovirus function involves infection of tissue culture cells and determination of protein expression levels. We have performed Western blot analysis of several of the recombinant adenoviruses, including NAIP, XIAP and XIAP-ZF. The remaining viruses may be readily assessed for protein expression using the polyclonal IAP antibodies. Functional analysis of the antisense viruses may be done at the RNA level using either Northern blots of total RNA harvested from infected tissue culture cells or ribonuclease protection assays. Western blot analysis of infected cells will be used to determine whether the expressed antisense RNA interferes with IAP expression in the host cell.

3. Documentation that IAP overexpression results in increased drug resistance. We have optimized cell death assays to allow high through-put of samples with minimal sample variation. Testing of the sense IAP adenoviruses for their ability to alter drug sensitivity of breast and pancreatic adenocarcinoma cell lines may be accomplished as follows. Cancer cell lines are infected with the recombinant viruses, cultured for 5 days, then subdivided into 24 well plates. Triplicate cell samples each receive increasing concentrations of the anti-cancer drug under investigation. Samples are harvested at 24, 48, and 72 hours post-exposure, and assayed for the number of viable cells in the well. The dose response curve is then compared to uninfected and control virus (both positive and negative) infected cells. One may document a dramatic increase in the relative resistance of the cancer cell lines when infected with the sense viruses, confirming our hypothesis that overexpression of the IAP proteins contributes to the anti-apoptotic phenotype of cancer cells. Initial experiments utilize the drugs doxorubicin and adriamycin.

4. Documentation that antisense IAP overexpression results in increased drug sensitivity. Having confirmed that IAP overexpression renders cancer cells more resistant to chemotherapeutic drugs, one may examine whether the antisense adenoviruses render the same cells more sensitive. The effectiveness of antisense IAP viruses relative to antisense Bcl-2 virus will also be assessed as a crucial milestone.

5. Identification of antisense oligonucleotides. Concomitant to the adenovirus work, we have designed a series of antisense oligonucleotides to various regions of each of the IAPs. A generally accepted model of how antisense oligonucleotides function proposes that the formation of RNA/DNA duplexes in the nucleus activates cellular RnaseH enzymes which then enzymatically degrade the mRNA component of the hybrid. Virtually any region of the mRNA can be targeted, and therefore choosing an appropriate sequence to target is somewhat empirical.

6. Optimization of oligonucleotides. A secondary round of oligonucleotides may be made when effective target regions have been identified. These oligonucleotides target sequences in the immediate vicinity of the most active antisense oligonucleotides identified using methods such as those provided above. A second round of testing by Northern blot analysis may be required.

7. Testing antisense oligonucleotides in vitro. Following successful identification and optimization of targeting oligonucleotides, one may test these in the tissue culture model system using the optimal cell lines such as those described in the cancer survey described in U.S. Ser. No. 08/800,929, incorporated herein by reference. Experimental procedures may parallel those used in the recombinant antisense adenovirus work. Negative control oligonucleotides with miss-match sequences are used to establish base line or non-specific effects. Assisted transfection of the oligonucleotides using cationic lipid carriers may be compared to unassisted transfection. Confirmation of the effectiveness of specific antisense oligonucleotides prompts synthesis of oligonucleotides with modified phosphodiester linkages, such as phosphorothioate or methylimino substituted oligonucleotides. These may also be tested in vitro.

8. Animal modeling of antisense oligonucleotide therapies. Animal modeling of the effectiveness of the antisense IAP approach is described here. Cell lines are routinely assessed for their tumorigenic potential in "nude" mice, a hairless strain of mouse that is immunocompromised, and thus extremely susceptible to developing tumors. In the nude mouse assay, cancer cells are grown in tissue culture and then injected under the skin at multiple sites. The frequency with which these cells give rise to palpable tumors within a defined period of time provides an index of the tumorigenic potential of the cell line in the absence of interference by a functional immune system. Preliminary assessment of an antisense IAP therapeutic involves injection of cancer cells infected with the recombinant adenoviruses (sense, antisense, and control viruses) under the skin, and the tumorigenic index compared to that of untreated cells. One may also use this model to assess the effectiveness of systemic administration of antisense oligonucleotides in increasing the efficacy of anti-cancer drugs in the nude mouse model. Phosphorothioate or methylimino substituted oligonucleotides will be assessed at this stage. This type of antisense oligo has demonstrated enhanced cell permeability and slower clearance rates from the body in experimental animal models.

EXAMPLE 2

Antisense Oligonucleotide (ODN) Selection

We selected 96 or 98, mostly non-overlapping, 19-mer antisense oligonucleotide (ODN) sequences for XIAP and HIAP1, respectively, based on the selection criteria listed below. In the case of XIAP, we selected 96 sequences (each being 19 nucleobases in length) (SEQ ID NOS: 1 through 96; Table 1), from a region approximately 1 kb upstream of the start codon to approximately 1 kb downstream of the stop codon of the cDNA sequence (FIG. 15). This blanketed approximately 50% of the coding region, and immediate 5' and 3' UTR sequences (i.e., 96 19-mers span 1.8 kb of sequence, while the targeted region is approximately 3.5 kb in length, comprised of a coding region of 1.5 kb plus 1 kb at either side of UTR sequences).

TABLE I

XIAP Antisense Oligonucleotides

| SEQ ID NO: | Code | Position in XIAP Sequence | Antisense Oligonucleotide Sequence |
|---|---|---|---|
| 1 | A1 | 2 | AAAATTCTAAGTACCTGCA |
| 2 | B1 | 21 | TCTAGAGGGTGGCTCAGGA |
| 3 | C1 | 44 | CAGATATATATGTAACACT |
| 4 | D1 | 78 | TGAGAGCCCTTTTTTGTT |
| 5 | E1 | 110 | AGTATGAAATATTTCTGAT |
| 6 | F1 | 134 | ATTGGTTCCAATGTGTTCT |
| 7 | G1 | 160 | TTAGCAAAATATGTTTTAA |
| 8 | H1 | 185 | TGAATTAATTTTTAATATC |
| 9 | A2 | 238 | ATTCAAGGCATCAAAGTTG |
| 10 | B2 | 326 | GTCAAATCATTAATTAGGA |
| 11 | C2 | 370 | AATATGTAAACTGTGATGC |
| 12 | D2 | 411 | GCAGAATAAAACTAATAAT |
| 13 | E2 | 430 | GAAAGTAATATTTAAGCAG |
| 14 | F2 | 488 | TTACCACATCATTCAAGTC |
| 15 | G2 | 508 | CTAAATACTAGAGTTCGAC |
| 16 | H2 | 535 | ACACGACCGCTAAGAAACA |
| 17 | A3 | 561 | TATCCACTTATGACATAAA |
| 18 | B3 | 580 | GTTATAGGAGCTAACAAAT |
| 19 | C3 | 607 | AATGTGAAACACAAGCAAC |
| 20 | D3 | 638 | ACATTATATTAGGAAATCC |
| 21 | E3 | 653 | CTTGTCCACCTTTTCTAAA |
| 22 | F3 | 673 | ATCTTCTCTTGAAAATAGG |
| 23 | G3 | 694 | CCTTCAAAACTGTTAAAAG |
| 24 | H3 | 721 | ATGTCTGCAGGTACACAAG |
| 25 | A4 | 759 | ATCTATTAAACTCTTCTAC |
| 26 | B4 | 796 | ACAGGACTACCACTTGGAA |
| 27 | C4 | 815 | TGCCAGTGTTGATGCTGAA |
| 28 | D4 | 835 | GTATAAAGAAACCCTGCTC |
| 29 | E4 | 856 | CGCACGGTATCTCCTTCAC |
| 30 | F4 | 882 | CTACAGCTGCATGACAACT |
| 31 | G4 | 907 | GCTGAGTCTCCATATTGCC |
| 32 | H4 | 930 | ATACTTTCCTGTGTCTTCC |
| 33 | A5 | 950 | GATAAATCTGCAATTTGGG |
| 34 | B5 | 990 | TTGTAGACTGCGTGGCACT |
| 35 | C5 | 1010 | ACCATTCTGGATACCAGAA |
| 36 | D5 | 1029 | AGTTTTCAACTTTGTACTG |
| 37 | E5 | 1059 | ATGATCTCTGCTTCCCAGA |
| 38 | F5 | 1079 | AGATGGCCTGTCTAAGGCA |
| 39 | G5 | 1100 | AGTTCTCAAAAGATAGTCT |
| 40 | H5 | 1126 | GTGTCTGATATATCTACAA |
| 41 | A6 | 1137 | TCGGGTATATGGTGTCTGA |
| 42 | B6 | 1146 | CAGGGTTCCTCGGGTATAT |
| 43 | C6 | 1165 | GCTTCTTCACAATACATGG |
| 44 | D6 | 1192 | GGCCAGTTCTGAAAGGACT |
| 45 | E6 | 1225 | GCTAACTCTCTTGGGGTTA |
| 46 | F6 | 1246 | GTGTAGTAGAGTCCAGCAC |
| 47 | G6 | 1273 | AAGCACTGCACTTGGTCAC |
| 48 | H6 | 1294 | TTCAGTTTTCCACCACAAC |
| 49 | A7 | 1316 | ACGATCACAAGGTTCCCAA |
| 50 | B7 | 1337 | TCGCCTGTGTTCTGACCAG |
| 51 | C7 | 1370 | CCGGCCCAAAACAAAGAAG |
| 52 | D7 | 1393 | GATTCACTTCGAATATTAA |
| 53 | E7 | 1413 | TATCAGAACTCACAGCATC |
| 54 | F7 | 1441 | GGAAGATTTGTTGAATTTG |
| 55 | G7 | 1462 | TCTGCCATGGATGGATTTC |
| 56 | H7 | 1485 | AAGTAAAGATCCGTGCTTC |
| 57 | A8 | 1506 | CTGAGTATATCCATGTCCC |
| 58 | B8 | 1525 | GCAAGCTGCTCCTTGTTAA |
| 59 | C8 | 1546 | AAAGCATAAAATCCAGCTC |
| 60 | D8 | 1575 | GAAAGCACTTTACTTTATC |
| 61 | H8 | 1610 | ACTGGGCTTCCAATCAGTT |
| 62 | E8 | 1629 | GTTGTTCCCAAGGGTCTTC |
| 63 | F8 | 1650 | ACCCTGGATACCATTTAGC |
| 64 | G8 | 1669 | TGTTCTAACAGATATTTGC |
| 65 | A9 | 1688 | TATATATTCTTGTCCCTTC |
| 66 | B9 | 1696 | AGTTAAATGAATATTGTTT |
| 67 | C9 | 1725 | GACACTCCTCAAGTGAATG |
| 68 | D9 | 1745 | TTTCTCAGTAGTTCTTACC |
| 69 | E9 | 1759 | GTTAGTGATGGTGTTTTCT |
| 70 | F9 | 1782 | AGATGGTATCATCAATTCT |
| 71 | G9 | 1801 | TGTACCATAGGATTTTGGA |
| 72 | H9 | 1820 | CCCCATTCGTATAGCTTCT |
| 73 | A10 | 1849 | ATTATTTTCTTAATGTCCT |
| 74 | B10 | 1893 | CAAGTGATTTATAGTTGCT |
| 75 | C10 | 1913 | TAGATCTGCAACCAGAACC |
| 76 | D10 | 1945 | CATCTTGCATACTGTCTTT |
| 77 | E10 | 1997 | CCTTAGCTGCTCTTCAGTA |
| 78 | F10 | 2018 | AAGCTTCTCCTCTTGCAGG |
| 79 | G10 | 2044 | ATATTTCTATCCATACAGA |
| 80 | H10 | 2076 | CTAGATGTCCACAAGGAAC |
| 81 | A11 | 2096 | AGCACATTGTTTACAAGTG |
| 82 | B11 | 2123 | AGCACATGGGACACTTGTC |
| 83 | C11 | 2144 | CTTGAAAGTAATGACTGTG |
| 84 | D11 | 2182 | CCTACTATAGAGTTAGATT |
| 85 | E11 | 2215 | ATTCAATCAGGGTAATAAG |
| 86 | F11 | 2234 | AAGTCAGTTCACATCACAC |
| 87 | G11 | 2375 | CAGTAAAAAAAATGGATAA |
| 88 | H11 | 2428 | TTCAGTTATAGTATGATGC |
| 89 | A12 | 2471 | TACACTTAGAAATTAAATC |
| 90 | B12 | 2630 | TCTCTATCTTTCCACCAGC |
| 91 | C12 | 2667 | AGAATCCTAAAACACAACA |
| 92 | D12 | 2709 | ATTCGCACAAGTACGTGTT |
| 93 | E12 | 2785 | TGTCAGTACATGTTGGCTC |
| 94 | F12 | 2840 | ACATAGTGTTTTGCCACTT |
| 95 | G12 | 2861 | CTTTGATCTGGCTCAGACT |
| 96 | H12 | 2932 | GAAACCACATTTAACAGTT |

Note that the three most 5' and the three most 3' nucleobases may comprise DNA residues, or RNA residues, such as 2'-O methyl RNA residues. For example, the antisense oligonucleotide sequence of SEQ ID NO: 3 may be CAGATATATATGTAACACT or CAGATATATATGTAA-CACU.

A similar approach was taken for designing antisense oligonucleotides against HIAP1. Ninety-eight 19-mer sequences were chosen, with some of the latter sequences picked using less stringent criteria than the originally defined selection criteria (listed below), to increase the number of candidate sequences to study (SEQ ID NOS: 97; through 194; Table 2). Of these 98 sequences targeted to the HIAP1 sequence of FIGS. 16, 15 (SEQ ID NOS: 97 through 104, 107, 113, 136, 156, 157, 181, and 193) were selected to evaluate the efficacy of decreasing HIAP1 expression. These 15 candidate sequences consisted of 4 sequences targeting the coding region (SEQ ID NOS: 136, 156, 157, and 181), 1 sequence targeting the 3'UTR (SEQ ID NO: 193), and 7 sequences targeting the 5'UTR SEQ ID NOS: 100 through 104, 107, and 113; one of the 7 oligonucleotides overlapped the start codon), and 3 other oligonucleotides (SEQ ID NOS: 97 through 99) that were designed to target an intronic segment of the 5'UTR (the value of which is discussed in Example 7). These above-described 15 HIAP1 antisense oligonucleotides were synthesized and tested.

TABLE 2

HIAP1 Antisense Oligonucleotides

| SEQ ID NO | Code | Position in HIAP1 Sequence | Antisense Oligonucleotide Sequence |
|---|---|---|---|
| 97 | APO 1 | 1152 | TCATTTGAGCCTGGGAGGU |
| 98 | APO 2 | 1172 | CGGAGGCTGAGGCAGGAGA |
| 99 | APO 3 | 1207 | GGTGTGGTGGTACGCGCCT |
| 100 | APO 4 | 1664 | ACCCATGCACAAAACTACC |
| 101 | APO 5 | 1865 | AGAATGTGCCAGTAGGAGA |

TABLE 2-continued

HIAP1 Antisense Oligonucleotides

| SEQ ID NO | Code | Position in HIAP1 Sequence | Antisense Oligonucleotide Sequence |
|---|---|---|---|
| 102 | APO 6 | 2440 | TCTCACAGACGTTGGGCTT |
| 103 | APO 7 | 2469 | CCAGTGGTTTGCAAGCATG |
| 104 | APO 8 | 3695 | GAAATTTAGTGGCCAGGAA |
| 105 | | 4013 | AGAAATACACAATTGCACC |
| 106 | | 4032 | TACTGATACATTTTAAGGA |
| 107 | APO 9 | 4057 | TTCAACATGGAGATTCTAA |
| 108 | | 4076 | ATTTCTATGCATTTAGAGT |
| 109 | | 4121 | AATACTAGGCTGAAAAGCC |
| 110 | | 4142 | GGCTTTGCTTTTATCAGTT |
| 111 | | 4165 | TCTAGGGAGGTAGTTTTGT |
| 112 | | 4189 | GGGAAGAAAAGGGACTAGC |
| 113 | APO 10 | 4212 | GTTCATAATGAAATGAATG |
| 114 | | 4233 | ATAAGAATATGCTGTTTTC |
| 115 | | 4265 | TTCAAACGTGTTGGCGCTT |
| 116 | | 4283 | ATGACAAGTCGTATTTCAG |
| 117 | | 4317 | AAGTGGAATACGTAGACAT |
| 118 | | 4338 | AGACAGGAACCCCAGCAGG |
| 119 | | 4357 | CGAGCAAGACTCCTTTCTG |
| 120 | | 4376 | AGTGTAATAGAAACCAGCA |
| 121 | | 4395 | TGACCTTGTCATTCACACC |
| 122 | | 4426 | TTATCCAGCATCAGGCCAC |
| 123 | | 4445 | ACTGTCTCCTCTTTTCCAG |
| 124 | | 4464 | TTTTATGCTTTTCAGTAGG |
| 125 | | 4489 | ACGAATCTGCAGCTAGGAT |
| 126 | | 4517 | CAAGTTGTTAACGGAATTT |
| 127 | | 4536 | TAGGCTGAGAGGTAGCTTC |
| 128 | | 4555 | GTTACTGAAGAAGGAAAAG |
| 129 | | 4574 | GAATGAGTGTGTGGAATGT |
| 130 | | 4593 | TGTTTTCTGTACCCGGAAG |
| 131 | | 4612 | GAGCCACGGAAATATCCAC |
| 132 | | 4631 | TGATGGAGAGTTTGAATAA |
| 133 | | 4656 | GATTTGCTCTGGAGTTTAC |
| 134 | | 4670 | GGCAGAAAATTCTTGATTT |
| 135 | | 4696 | GGACAGGGGTAGGAACTTC |
| 136 | APO 11 | 4714 | GCATTTTCGTTATTCATTG |
| 137 | | 4733 | CTGAAAAGTAAGTAATCTG |
| 138 | | 4759 | GGCGACAGAAAAGTCAATG |
| 139 | | 4812 | CCACTCTGTCTCCAGGTC |
| 140 | | 4831 | CCACCACAGGCAAAGCAAG |
| 141 | | 4855 | TTCGGTTCCCAATTGCTCA |
| 142 | | 4874 | TTCTGACATAGCATTATCC |
| 143 | | 4893 | TGGGAAAATGTCTCAGGTG |
| 144 | | 4907 | TATAAATGGGCATTTGGGA |
| 145 | | 4926 | TGTCTTGAAGCTGATTTTC |
| 146 | | 4945 | GAAACTGTGTATCTTGAAG |
| 147 | | 4964 | TGTCTGCATGCTCAGATTA |
| 148 | | 4988 | GAATGTTTTAAAGCGGGCT |
| 149 | | 5007 | CACTAGAGGGCCAGTTAAA |
| 150 | | 5040 | CCGCACTTGCAAGCTGCTC |
| 151 | | 5070 | CATCATCACTGTTACCCAC |
| 152 | | 5095 | CCACCATCACAGCAAAAGC |
| 153 | | 5117 | TCCAGATTCCCAACACCTG |
| 154 | | 5130 | CCCATGGATCATCTCCAGA |
| 155 | | 5149 | AACCACTTGGCATGTTGAA |
| 156 | APO 12 | 5168 | CAAGTACTCACACCTTGGA |
| 157 | APO 13 | 5187 | CCTGTCCTTTAATTCTTAT |
| 158 | | 5206 | TGAACTTGACGGATGAACT |
| 159 | | 5225 | TAGATGAGGGTAACTGGCT |
| 160 | | 5244 | TGGATAGCAGCTGTTCAAG |
| 161 | | 5271 | CATTTTCATCTCCTGGGCT |
| 162 | | 529 | TGGATAATTGATGACTCTG |
| 163 | | 5309 | GTCTTCTCCAGGTTCAAAA |
| 164 | | 5337 | TATTCATCATGATTGCATC |
| 165 | | 5366 | CATTTCCACGGCAGCATTA |
| 166 | | 5367 | CCAGGCTTCTACTAAAGCC |
| 167 | | 5416 | GCTAGGATTTTTCTCTGAA |
| 168 | | 5435 | TCTATAATTCTCTCCAGTT |
| 169 | | 5454 | ACACAAGATCATTGACTAG |
| 170 | | 5473 | TCTGCATTGAGTAAGTCTA |
| 171 | | 5492 | CTCTTCCCTTATTTCATCT |
| 172 | | 5515 | TCCTCAGTTGCTCTTTCTC |
| 173 | | 5560 | GCCATTCTATTCTTCCGGA |
| 174 | | 5579 | AGTCAAATGTTGAAAAAGT |
| 175 | | 5598 | CCAGGATTGGAATTACACA |
| 176 | | 5622 | ATTCCGGCAGTTAGTAGAC |
| 177 | | 5646 | TAACATCATGTTCTTGTTC |
| 178 | | 5675 | GTCTGTGTCTTCTGTTTAA |
| 179 | | 5684 | TTCTCTTGCTTGTAAAGAC |
| 180 | | 5703 | CTAAAATCGTATCAATCAG |
| 181 | APO 14 | 5723 | GGCTGCAATATTTCCTTTT |
| 182 | | 5742 | GAGAGTTTCTGAATACAGT |
| 183 | | 5761 | ACAGCTTCAGCTTCTTGCA |
| 184 | | 5780 | AAATAAATGCTCATATAAC |
| 185 | | 5821 | GAAACATCTTCTGTGGGAA |
| 186 | | 5841 | GTTCTTCCACTGGTAGATC |
| 187 | | 5862 | CTTCTTGTAGTCTCCGCAA |
| 188 | | 5890 | TTGTCCATACACACTTTAC |
| 189 | | 6097 | AACCAAATTAGGATAAAAG |
| 190 | | 6181 | ATGTTCATATGGTTTAGAT |
| 191 | | 6306 | TAAGTTTTACTTCACTTAC |
| 192 | | 6369 | ATGTTCCCGGTATTAGTAC |
| 193 | APO 15 | 6432 | GGGCTCAAGTAATTCTCTT |
| 194 | | 6455 | GCCCAGGATGGATTCAAAC |

Oligonucleotide Selection Criteria

The computer program OLIGO (previously distributed by National Biosciences Inc.) was used to define suitable antisense oligonucleotides based on the following criteria: 1) no more than 75% GC content, and no more than 75% AT content; 2) preferably no oligonucleotide with 4 or more consecutive G residues (due to reported toxic effects, although one was chosen as a toxicity control); 3) no oligonucleotides with the ability to form stable dimers or hairpin structures; and 4) sequences around the translation start site are a preferred region. In addition, accessible regions of the mRNA were predicted with the help of the RNA secondary structure folding program mfold, by M. Zuker (website 1999–2000: htfp://mfold2.wustl.edu/~mfold/rna/form1.cgi). Sub-optimal folds with a free energy value within 5% of the predicted most stable fold of the mRNA were predicted using a window of 200 bases within which a residue can find a complimentary base to form a base pair bond. Open regions that did not form a base pair were summed together with each suboptimal fold and areas that consistently were predicted as open were considered more accessible to the binding of antisense oligonucleotides. Additional oligonucleotides that only partially fulfilled some of the above selection criteria (1–4), were also chosen as possible candidates if they recognized a predicted open region of the target mRNA.

EXAMPLE 3

Antisense Oligonucleotide Synthesis

The antisense oligonucleotides were synthesized by IDT (Integrated DNA Technologies, USA) as chimeric, second-generation oligonucleotides, consisting of a core of phosphodiester DNA residues flanked on either side by two 2'-O methyl RNA residues with a phosphorothioate linkage between the flanking RNA residues. The oligonucleotides were provided in a 96-well plate, as well as matching tubes, with a minimum of 12 ODs of oligo DNA, which provided ample material for transfections (greater than a hundred assays in the 96-well format) when the detection method is a sensitive method, such as TaqMan quantitative PCR, or an ELISA. Once the positive hits were identified (see below), the antisense oligonucleotides were re-synthesized with 3, instead of 2, flanking RNA residues to further increase stability/nuclease resistance. In addition, for validation purposes, appropriate controls (such as scrambled, 4-base mismatch, and reverse polarity oligonucleotides) were synthesized for some of the antisense targets that yielded the highest antisense activity.

EXAMPLE 4

Screening Assays and Optimization of Antisense Oligonucleotide Sequences

Our approach to identifying IAP antisense oligonucleotides was to screen the above-described antisense oligonucleotide libraries for specific decreases (knock-down) of the RNA and protein for the specific IAP gene targeted. Any number of standard assays may be used to detect RNA and protein levels in cells that have been administered an IAP antisense nucleic acid. For example, RNA levels can be measured using standard Northern blot analysis or RT-PCR techniques. In addition, protein levels can be measured, for example, by standard Western blot analyses or immunoprecipitation techniques. Alternatively, cells administered an antisense IAP nucleic acid may be examined for cell viability, according to methods described for example, in U.S. Pat. No. 5,919,912, or U.S. Ser. Nos. 08/576,956, 08/800,929, incorporated herein by reference.

We used TaqMan quantitative PCR conditions (described below) to assay for changes in mRNA levels after antisense oligonucleotide treatment, as well as our ELISA method for XIAP and Western blotting (described below) for changes in HIAP1 protein levels, using a polyclonal anti-RIAP1 antibody (rat HIAP1 ortholog; AEgera Therapeutics, Inc.) in the latter case. Transfection conditions were optimized with LipofectAMINE PLUS (Life Technologies, Canada) on T24 bladder carcinoma cells, or lipofectin on SF-295 glioblastoma cells, using a fluorescein-tagged control sense oligo from XIAP spanning the start codon (mGmAG AAG ATG ACT GGT AAmC mA; SEQ ID NO: 195). The results were visualized and gauged by epi-fluorescence microscopy. In addition, in the case of T24 cells, transfections were further optimized based on the ability of a published antisense oligonucleotide to downregulate survivin expression (Li et al., Nat. Cell Biol. 1:461–466, 1999) (U/TGT GCT ATT CTG TGA AU/TU/T SEQ ID NO: 196). We optimized the transfection conditions based on the TaqMan results of survivin RNA knock-down detected with PCR primers and fluorescent probe, described in detail below. Optimal conditions for oligo uptake by the cells were found to be 940 nM oligonucleotide and 40 µL PLUS reagent and 0.8 µL LipofectAMINE in a total of 70 µL for 3 hours. We then applied these conditions to screen for XIAP protein knock-down using the oligo library against T24 cells.

HIAP1 knock-down was studied in SF-295 cells because these cells had easily detectable and discernable 70 kDa HIAP1 protein, while many cell lines do not express high levels of the protein, or are not distinguishable from the large amounts of the similarly sized 68 kDa HIAP2 protein. In fact, there are a number of published errors involving HIAP1 and HIAP2 in the literature because of naming errors in the databases, and because of the poor quality and high crossreactivity, of the various commercial antibodies to HIAP1/cIAP2. The best way to distinguish HIAP1 from HIAP2 is to perform an immunoprecipitation experiment with an IAP antibody (Aegera Therapeutics, Inc.), separate the proteins by 2-dimensional gel electrophoresis, and to then carry out mass spectroscopy analysis of the spots migrating in the 68 to 70 kDa range to verify the identity of the HIAP1 and HIAP2 bands, using standard methods known in the art. This method determines if HIAP1 and HIAP2 co-migrate at the 68 kDa position, and if the 70 kDa form of HIAP1 results from a splice variant or a post-translational modification.

Real-time PCR

RNA was extracted from cells lysed in RLT buffer (QIAGEn, Inc., Canada), and purified using QIAGEN RNeasy columns/kits. Real-time quantitative PCR was performed on a Perkin-Elmer ABI 7700 Prism PCR machine. RNA was reverse transcribed and amplified according to the TaqMan Universal PCR Master Mix protocol of PE Biosystems, using primers and probes designed to specifically recognize XIAP, HIAP1, survivin, or GAPDH. For human survivin, the forward primer was 5'-TCT GCT TCA AGG AGC TGG AA-3', the reverse primer was 5'-GAA AGG AAA GCG CAA CCG-3', and the probe was 5'-(FAM) AGC CAG ATG ACG ACC CCA TAG AGG AAC ATA (TAMRA)-3' (SEQ ID NOS: 197 through 199). For human HIAP1, the forward primer was 5'-TGG AGA TGA TCC ATG GGT TCA-3', the reverse primer was 5'-GAA CTC CTG TCC TTT AAT TCT TAT CAA GT-3', and the probe was 5'-(FAM) CTC ACA CCT TGG AAA CCA CTT GGC ATG(TAMRA)-3' (SEQ ID NOS: 200 through 202). For human XIAP, the forward primer was 5'-GGT GAT AAA GTA AAG TGC TTT CAC TGT-3', the reverse primer was 5'-TCA GTA GTT CTT ACC AGA CAC TCC TCA A-3', and the probe was 5'-(FAM) CAA CAT GCT AAA TGG TAT CCA GGG TGC AAA TAT C(TAMRA)-3' (SEQ ID NOS: 203 through 205). For human GAPDH, the forward primer was 5'-GAA GGT GAA GGT CGG AGT C-3', the reverse primer was 5'-GAA GAT GGT GAT GGG ATT C-3', and the probe was 5'-(JOE) CAA GCT TCC CGT TCT CAG CC(TAMRA)-3' (SEQ ID NOS: 206 through 208).

Relative quantitation of gene expression was performed as described in the PE Biosystems manual using GAPDH as an internal standard. The comparative Ct (cycle threshold) method was used for relative quantitation of IAP mRNA levels compared to GAPDH mRNA levels. Briefly, real-time fluorescence measurements were taken at each PCR cycle and the threshold cycle (Ct) value for each sample was calculated by determining the point at which fluorescence exceeded a threshold limit of 30 times the baseline standard deviation. The average baseline value and the baseline SD are calculated starting from the third cycle baseline value and stopping at the baseline value three cycles before the signal starts to exponentially rise. The PCR primers and/or probes for the specific IAPs were designed to span at least one exon-intron boundary separated by 1 or more kb of genomic DNA, to reduce the possibility of amplifying and detecting genomic DNA contamination. The specificity of the signal, and possible contamination from DNA, were verified by treating some RNA samples with either DNase or RNase, prior to performing the reverse transcription and PCR reaction steps.

XIAP ELISA and HIAP1 Western Immunoblots

A standard colorimetric XIAP ELISA assay was performed using an affinity-purified rabbit polyclonal antibody to XIAP (Aegera Therapeutics, Inc.) as a capture antibody, and was detected with a XIAP monoclonal antibody (MBL, Japan) and a biotinylated anti-mouse Ig antibody and horseradish peroxidase-conjugated streptavidin and TMB substrate. Alternatively, a polyclonal XIAP or HIAP1 antibody may be used to measure XIAP or HIAP1 protein levels, respectively.

HIAP1 was detected on a Western immunoblot using an affinity-purified anti-RIAP1 rabbit polyclonal antibody as a primary antibody and was detected by ECL (Amersham) on X-ray film with a secondary horseradish-peroxidase-conjugated anti-rabbit Ig antibody and a chemiluminescent substrate. The anti-RIAP1 polyclonal antibody is raised against a GST-fusion of the rat ortholog of HIAP1. This antibody cross-reacts with both human and murine HIAP1 and HIAP2.

EXAMPLE 5

Antisense XIAP Oligonucleotides Decrease XIAP RNA and Polypeptide Expression

The XIAP synthetic library of 96 antisense oligonucleotides was first screened for decreases in XIAP protein levels. Specifically, T24 cells ($1.5 \times 10^4$ cells/well) were seeded in wells of a 96-well plate on day 1, and were cultured in antibiotic-free McCoy's medium for 24 hours. On day 2, the cells were transfected with XIAP antisense oligonucleotides as described above (oligonucleotides are labeled according to their plated position, i.e., A1 to H12, and include 2 repeats, A13 and B13 that contain lyophilized DNA pellets that stuck to the sealing membrane). Briefly, the oligos were diluted in 10 μl/well of serum-free, antibiotic-free McCoy's medium and then PLUS reagent was added. LipofectAMINE was diluted in 10 μl/well of serum-free, antibiotic-free McCoy's medium, and both mixes were incubated for 15 minutes at room temperature. The mixes were then combined and incubated for 15 minutes at room temperature.

In the meantime, the complete medium was removed from the cells and 50 μl/well of serum-free, antibiotic-free medium was added to the cells. The transfection mixes were added to the well, and the cells were incubated for 3 hours. Then 30 μl/well of serum-free, antibiotic-free medium and 100 μl/well of antibiotic-free complete medium, containing 2× fetal bovine serum were added to each well.

At day 3, XIAP RNA levels were measured using quantitative real-time PCR techniques, as described above. At day 4, XIAP protein levels were measured by ELISA (FIGS. 7A, 7C, 7E, 7G, 7I, and 7K), and total cellular protein was measured biochemically (FIGS. 7B, 7D, 7F, 7H, 7J, and 7L; used to normalize the XIAP protein levels). The results were compared to a mock transfection sample (treated with the transfection agent but no oligonucleotide DNA was added, and then processed as for the other samples). Time course experiments determined that the optimal time for protein knock-down to be around 12 to 24 hours.

The library was also screened for decreases in RNA levels, using TaqMan-specific PCR primers and fluorescent probes at the appropriate optimal time, using the primers and probes described above. Time course experiments determined mRNA to be optimally decreased at 6 to 9 hours. These results agree well with the protein results.

The first screen (although performed at a sub-optimal time point when XIAP levels are returning to normal, possibly due to an outgrowth of non-transfected cells) identified 16 antisense oligonucleotides (ODNs C2, E2, E3, F3, C4, D4, E4, F4, G4, C5, D5, B6, F6, D7, D8, F8) out of the total 96 antisense oligonucleotides tested that showed some decrease in XIAP protein levels relative to total protein, compared to mock (no ODN) transfection levels (FIGS. 7A, 7C, 7E, 7G, 7I, and 7K). Interestingly, total protein was decreased for each of these 16 ODNs, which indicates a toxic or cytostatic effect of these ODNs (FIGS. 7B, 7D, 7F, 7H, 7J, 7L). Note that ODNs B9 and C9 showed a clear drop in total protein but no relative drop in XIAP protein levels. These 16 hits were then validated more rigorously at more optimal time points XIAP protein and RNA knock-down results at 12 hours after the start of transfection.

The 16 antisense ODNs that showed some decrease in relative XIAP protein levels compared to mock transfection, were re-tested alone or in combination, with one control oligo (D2) included, for their ability to knock-down XIAP protein at a more optimal time point (12 hours) based on the above described time course studies (FIG. 8B). these ODNs were also examined for their ability to decrease XIAP mRNA levels at 12 hours, normalized against GAPDH levels, and compared to mock transfection. Total protein concentrations at 12 hours were also determined (FIG. 8C).

Figure 8A:
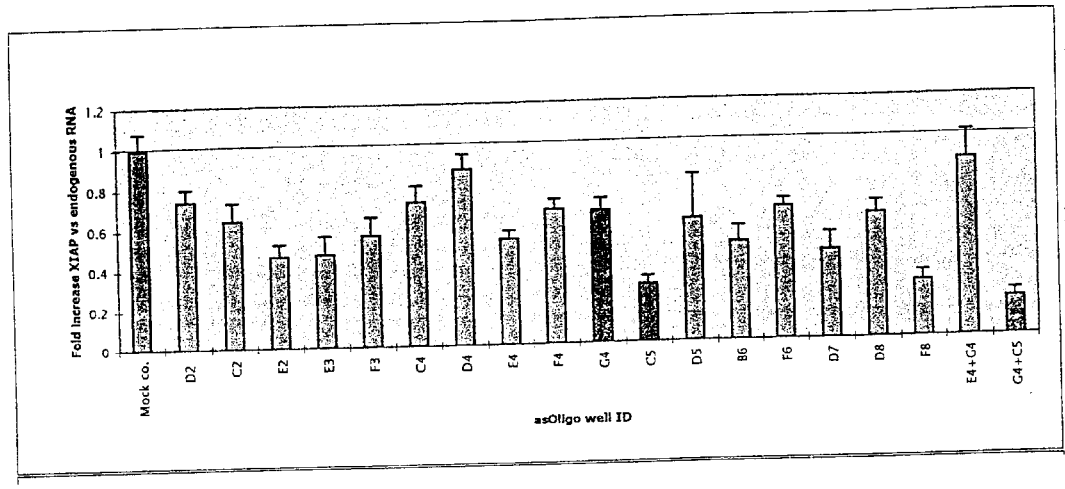
FIGS. 8A through 8C are graphs showing the effects of various antisense XIAP oligonucleotides, alone or in combination, on XIAP RNA (FIG. 8A) and protein (FIG. 8B).
Figure 8B:
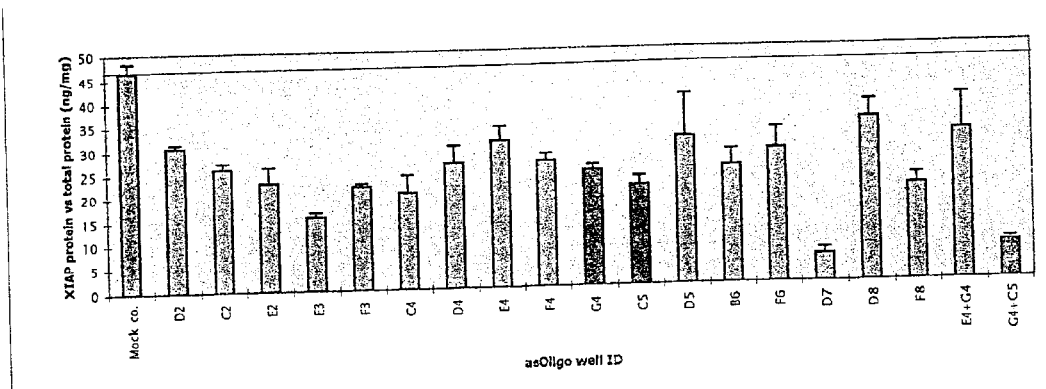
Figure 8C:
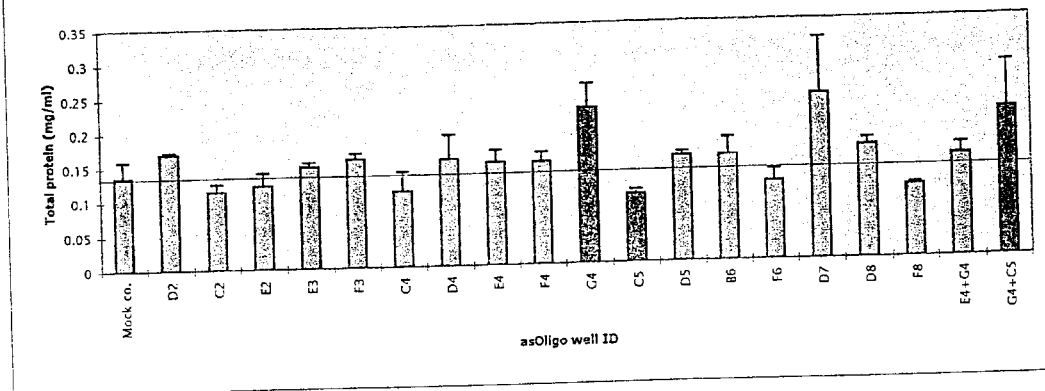

There was a good correlation between the ability of an antisense ODN to decrease XIAP protein levels (FIG. 8B) with its ability to decrease XIAP mRNA levels (FIG. 8A). In addition, there is no major loss of total protein at this early time point, and the decrease in XIAP mRNA and protein precede the decrease in total protein that is seen at later time points. The ODNs that showed greater than 50% loss of XIAP protein or mRNA levels alone, or in a combination of two ODNs added at a 0.5:0.5 ratio, were identified as the best ODNs and validated further. Of these 16 oligonucleotides, 10 of them (ODNs E2, E3, F3, E4, F4, G4, C5, B6, D7, F8) showed a consistent ability to decrease XIAP protein or RNA levels by more than 50%, depending on the transfection conditions used, or when used in combination, as for ODNs C5 and G4.

Interestingly, these 16 oligonucleotides that demonstrated antisense activity clustered in 4 different target regions of the XIAP mRNA, with adjacent ODNs showing some knock-down activity. No antisense activity was observed by oligonucleotides that target sequences between these regions or islands of sensitivity. Presumably, these regions represent open areas on the mRNA that are accessible to antisense ODNs inside the cell. Two antisense oligonucleotides, E3 and F3, target XIAP just upstream of the start codon in the intervening region between the IRES and the translation start site, and partially overlap the end of the IRES element. ODNs C2, D2, and E2 target a XIAP region upstream of the minimal IRES element, providing further evidence that the minimal IRES region is a highly structured region of RNA which is not readily accessible to antisense ODNs in vivo. All the other antisense ODN hits fall within the coding region, including a cluster of activity at positions 856–916 of the HIAP sequence of FIG. 15 (ODNs E4, F4, and G4) and smaller separate areas, as demonstrated by ODNs C5 and D5, for example.

EXAMPLE 6

XIAP Antisense Oligonucleotides Increase Cytotoxicity and Chemosensitization

We also investigated if XIAP antisense ODNs could chemosensitize the highly drug resistant T24 cells to traditional chemotherapeutic drugs, such as adriamycin or cisplatin. Antisense ODNs were chosen to represent some of the different XIAP target regions and were tested for their cytotoxic effects, alone or in combination with other ODNs or drugs. Five of the ten best XIAP antisense oligonucleotides were tested for their ability to kill or chemosensitize T24 bladder carcinoma cells, and were compared to the effects of three corresponding scrambled control ODNs.

Figure 9A:
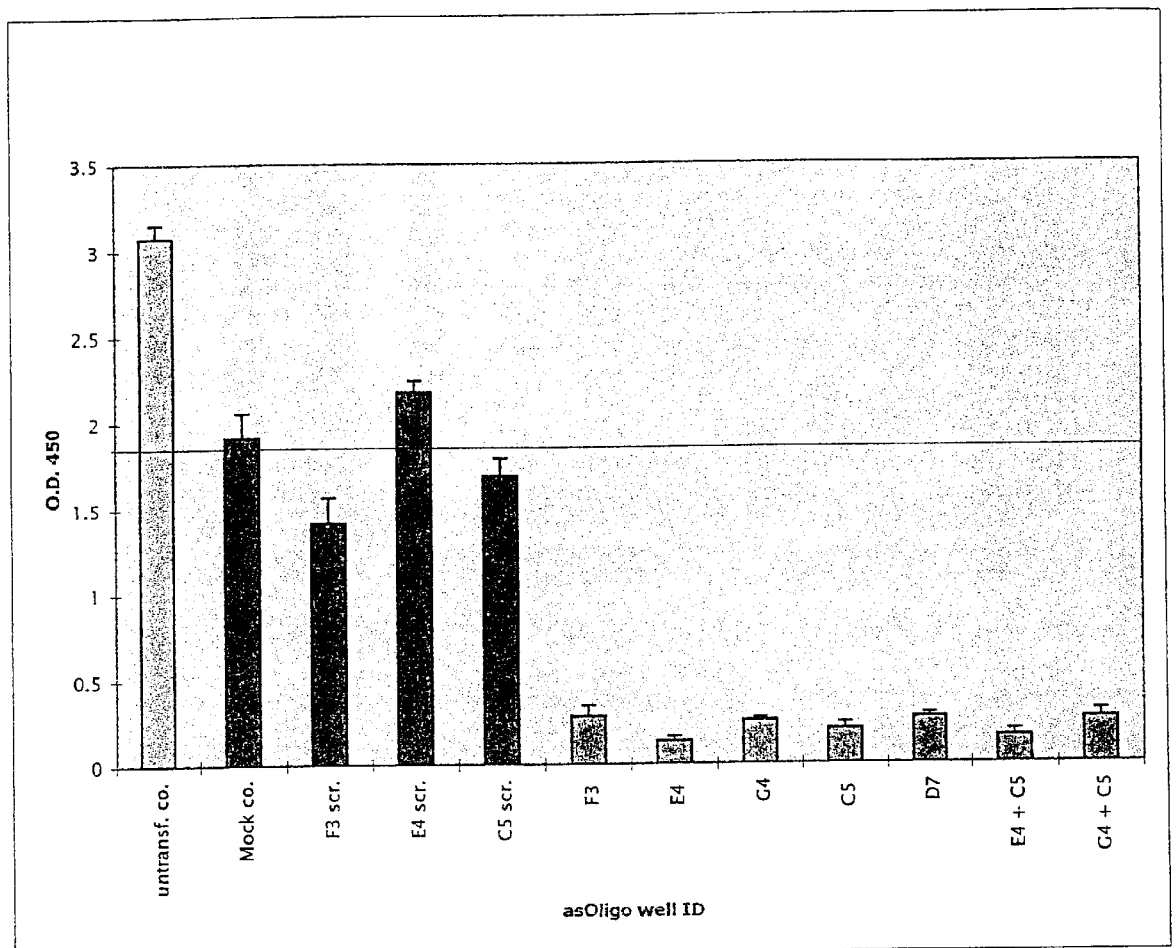

T24 cells were transfected with XIAP antisense oligonucleotides, scrambled oligonucleotides, no oligonucleotides (mock transfected), or were left untreated. The cells were tested for viability 20 hours after transfection (with the exception of the untreated control) using the WST-1 tetrazolium dye assay in which WST-1 tetrazolium dye is reduced to a colored formazan product in metabolically active cells (FIG. 9A). Alternatively, cell viability is tested using any one of the above described apoptosis methods.

The occurrence of cytotoxicity induced by the antisense XIAP ODN E4 was examined by visually inspecting T24 cells that were left untreated, mock transfected, or transfected with E4 antisense ODNs, E4 scrambled ODNs, E4 reverse polarity, or E4 mismatched ODNs. Twenty hours after transfection, the cells were examined for morphology (FIG. 9D). Only the cell transfected with antisense E4 ODNs showed signs of toxicity.

Figure 9B:
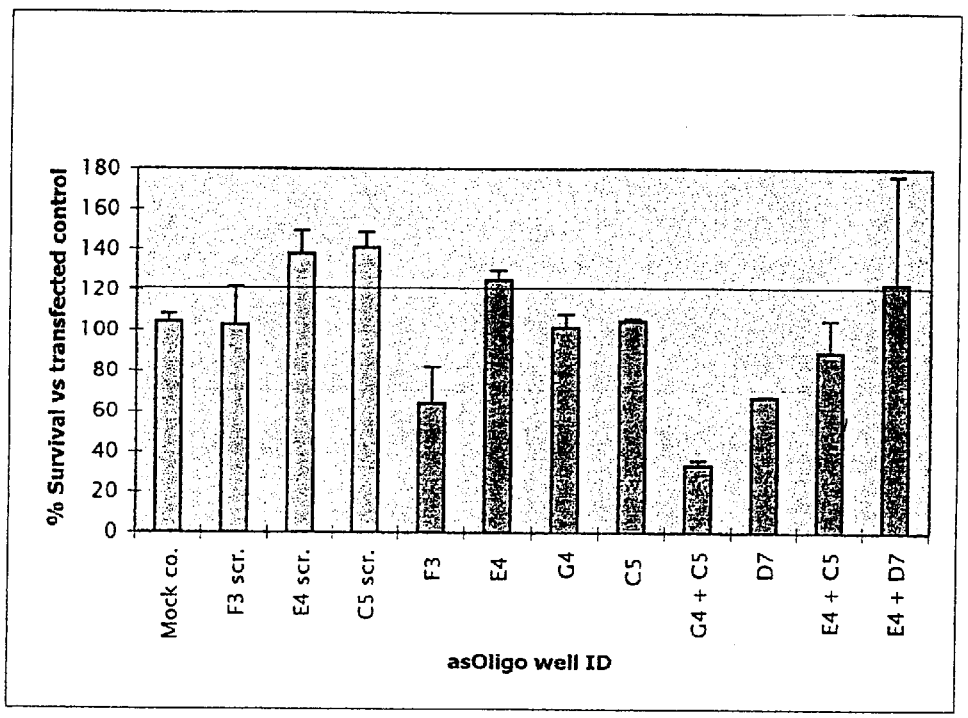
Figure 9C:
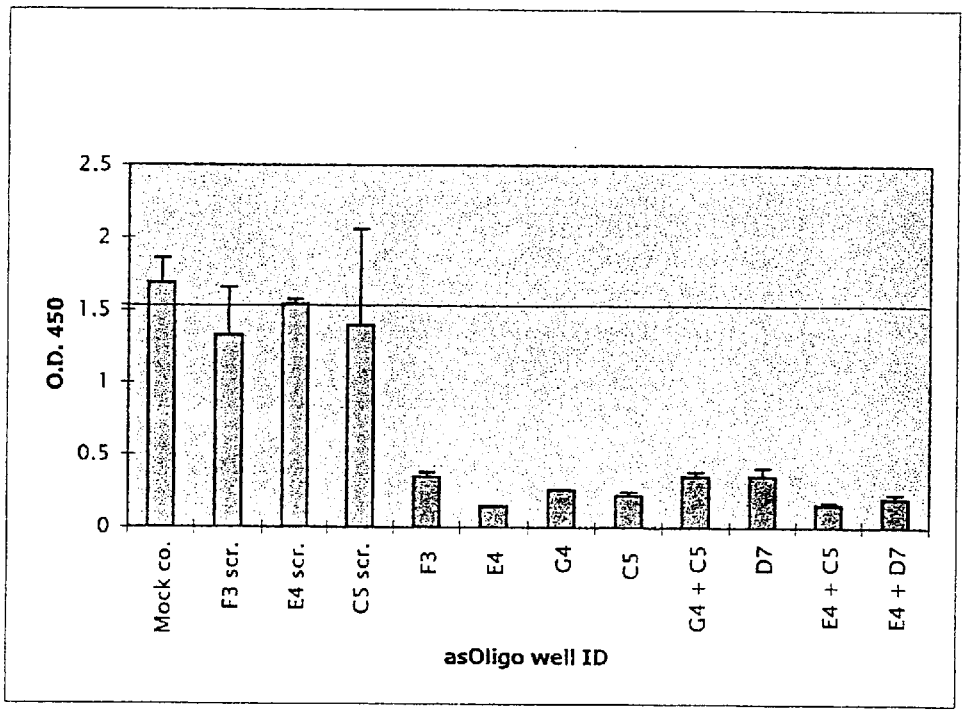

To examine the effects of the oligonucleotides on the chemosensitization of the T24 cells to cisplatin or adriamycin, oligonucleotides were tested for their ability to further kill T24 cells in the presence of a fixed dose of adriamycin (0.5 $\mu$g/ml). Cells were first transfected with the oligonucleotides, then adriamycin was added for another 20 hours. Viability was measured by WST-1 at the end of the 20 hour drug treatment (FIG. 9B). Values are shown as percentage viability compared to their ODN treatment alone results shown in FIG. 9C. FIG. 9C is essentially a repeat of FIG. 9A, but with the actual corresponding values used in calculating the results for the chemosensitization experiment in FIG. 9B.

All 5 oligonucleotides tested (ODNs F3, E4, G4, C5, D7, or the combinations of E4+C5, or G4+C5) killed the T24 cells, leaving only 10–15% surviving cells after 24 hours, as compared to the mock (no ODN) transfected cells, or to cells transfected with 3 corresponding scrambled controls to F3 (mCmAmG AGA TTT CAT TTA AmCmG mU; SEQ ID NO: 209), E4 (mCmUmA CgC TCg CCA TCg TmUmC mA; SEQ ID NO: 210) and C5 (mUmGmC CCA AGA ATA CTA GmUmC mA; SEQ ID NO: 211)(FIGS. 9A and C). Therefore, the toxicity is sequence-specific to those ODNs that reduce XIAP levels, and not to a non-sequence specific toxicity due to ODNs of this chemistry in general, as three scrambled controls did not show any more toxicity compared to the mock transfected control. This cytotoxicity may result from the combined effect of XIAP protein knockdown (and the expected loss of anti-apoptotic protection afforded by XIAP) and the cytotoxicity of the transfection itself. Both mock (no ODN) and scrambled ODN transfections resulted in an approximately 40% decrease in survival as compared to untreated cells (FIG. 9A). This is not unexpected, as the opposite is true (i.e., overexpression of IAPs protect insect cells from cytofectin-mediated cell death, a liposomal transfection agent similar to the ones used in these studies (Jones et al., J. Biol. Chem. 275:22157–22165, 2000)

The addition of a fixed dose of adriamycin or cisplatin at the end of the 3 hour transfection period resulted in a further decrease in survival for some of the tested oligonucleotides, a further 40% drop in survival after 20 hours for ODNs F3, D7 and G4+C5 combination (FIG. 9B), compared to their corresponding ODNs treated values (FIG. 9C). Note that the values in FIG. 9B (ODN plus drug) are compared to their corresponding ODN survival (ODN alone) in FIG. 9C, which is set a 100% for each ODN. Only the results for adriamycin chemosensitization are shown; however, similar results were obtained when the cells were chemosensitized with cisplatin. At the fixed doses used, the mock and scrambled control transfections did not show any increased loss of survival when either treated with adriamycin (FIG. 9B). Chemosensitization is only seen when XIAP levels are decreased by a specific antisense ODN.

EXAMPLE 7

Antisense HIAP1 Oligonucleotides Decrease HIAP1 RNA and Polypeptide Expression

The smaller library of 15 HIAP1 antisense oligonucleotides was screened for protein knock-down by Western and for RNA knock-down by TaqMan, using the primers and probes described above, under two different conditions. Alternatively, HIAP1 RNA levels may be detected using standard Northern blot analyses or RT-PCR techniques. The antisense oligonucleotides were administered to cells under basal conditions or under cycloheximide-induction conditions (24 hour treatment with sub-toxic doses). We have discovered that cycloheximide (CHX) can lead to a 10- to 200-fold induction of HIAP1 mRNA depending on the cell line treated. This in turn leads to an increase in HIAP1 protein, as seen on a Western blot (70 kDa band). We have also discovered that this effect of CHX is via two distinct mechanisms of action. First, CHX activates NFkB, a known transcriptional inducer of HIAP1, by blocking the de novo synthesis of a labile protein, IkB, which is an inhibitor of NFkB. This effect is mimicked by puromycin, another protein synthesis inhibitor, and by TNF-alpha, which induces a signaling cascade leading to the phosphorylation, ubiquination, and degradation of IkB. However, only CHX leads to a further stabilization of the HIAP1 mRNA, as seen by the decreased rate of disappearance of HIAP1 message in the presence of actinomycin D, to block de novo transcription, and CHX, as opposed to actinomycin D and puromycin or TNF-alpha combined.

SF295 glioblastoma cells were transfected with lipofectin and ODN (scrambled survivin, no oligo or mock, antisense APO1 to APO15) or left untreated. RNA was isolated from the cells 6 hours after transfection and the level of HIAP1 mRNA was measured by quantitative PCR (TaqMan analysis), normalized for GAPDH mRNA, with the value for the scrambled survivin ODN transfection set as 1.0.

Figure 10:
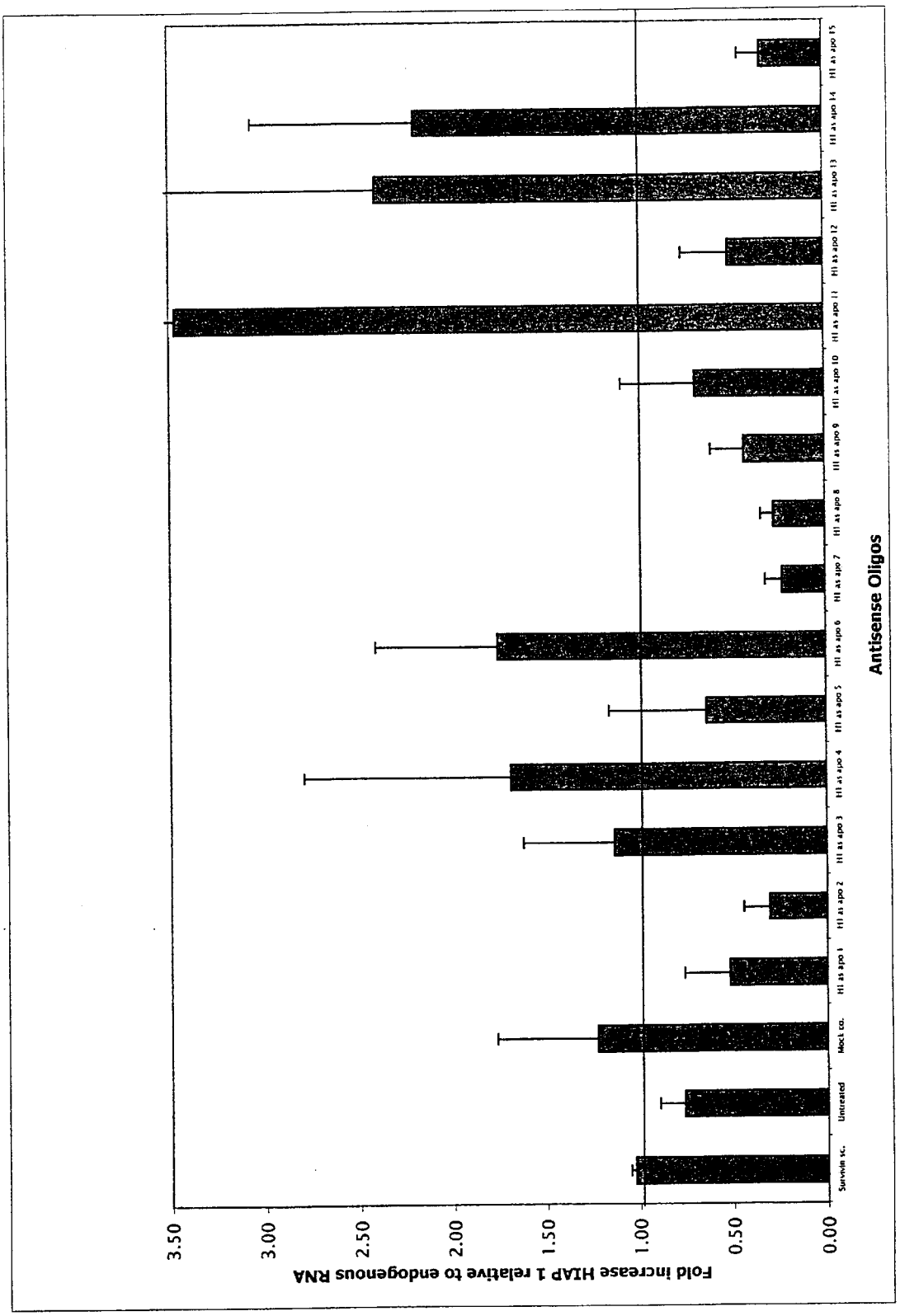
FIG. 10 is a graph showing the effects of HIAP1 antisense oligonucleotides on HIAP1 RNA levels.

The results of this experiment, a compilation of three separate experiments, are shown in FIG. 10. The scrambled survivin ODN, the mock transfection, and untreated (non-transfected) cells, all showed similar HIAP1 mRNA levels. Of the 15 antisense ODNs, 7 oligonucleotides (ODNs APO 1, −2, −7, −8, −9, −12, −15) showed an almost 50% decrease when compared to mock transfection or survivin scrambled control (mUmAmA GCT GTT CTA TGT GmUmU mC; SEQ ID NO: 212) ODN transfection (FIG. 10). Some of the ODNs led to an induction in HIAP1 mRNA, which may be a stress response to a non-specific toxic ODN. The antisense ODN, however, may still be effective at knocking down HIAP1 protein levels even if the message is increased if the ODN is able to interfere with the translation process.

Figure 11A:
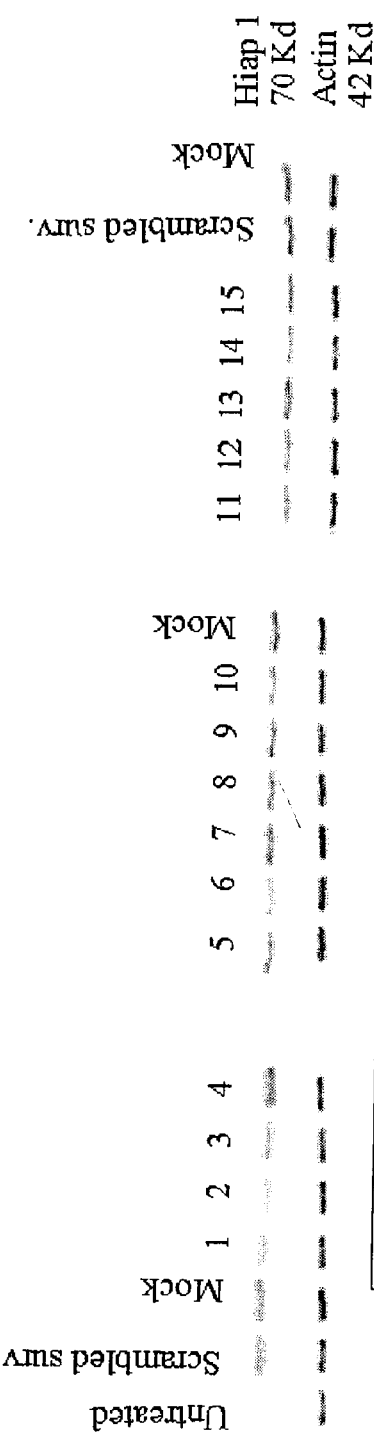
FIG. 11A is a densitometric scan of a Western blot showing the effects of HIAP1 antisense oligonucleotides on a cell's ability to block cycloheximide-induced upregulation of HIAP1 protein.

The effect of HIAP1 antisense oligonucleotides on HIAP1 protein and mRNA expression was also examined in cells induced to express HIAP1. SF295 cells were transfected with ODNs, or were mock transfected. The transfected cells were then treated with 10 $\mu$g/ml cycloheximide for 24 hours to induce 70 kDa HIAP1 mRNA and protein. Protein levels were measured by Western immunoblot analysis with an anti-RIAP1 polyclonal antibody, and normalized against actin protein in a re-probing of the same blots. Scans of the Western blot results are shown in FIG. 11A. The densitometric scan results were plotted against the mock results (set at 100%) in FIG. 11B. A line is drawn at 50% to easily identify the most effective antisense ODNs. The transfection process itself (e.g., mock or scrambled survivin) induces HIAP1 protein compared to the untreated sample as shown on the Western immunoblot.

Figure 12:
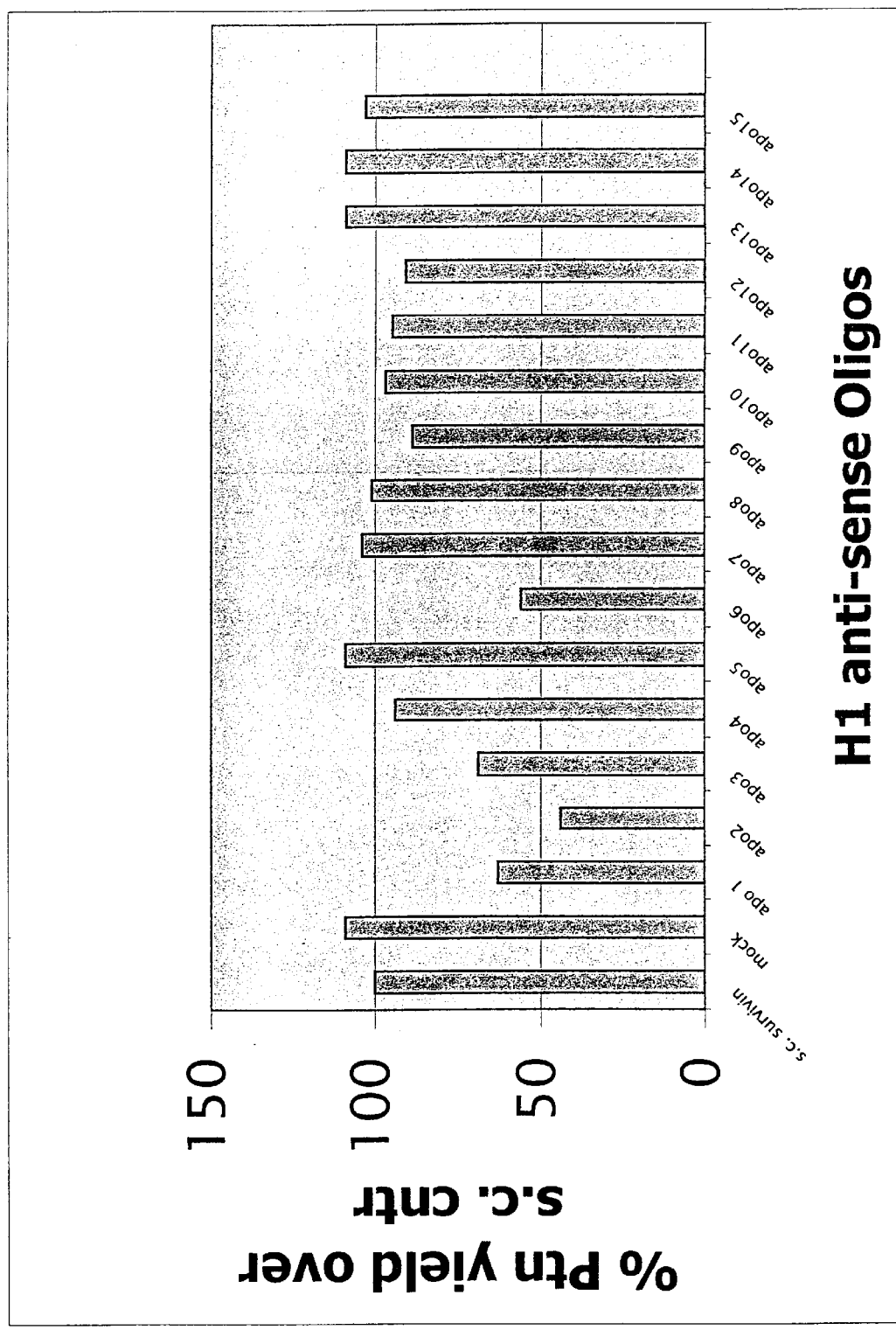
FIG. 12 is a graph showing the effects of HIAP1 antisense oligonucleotides on cytotoxicity, as measured by total protein.
Figure 13:
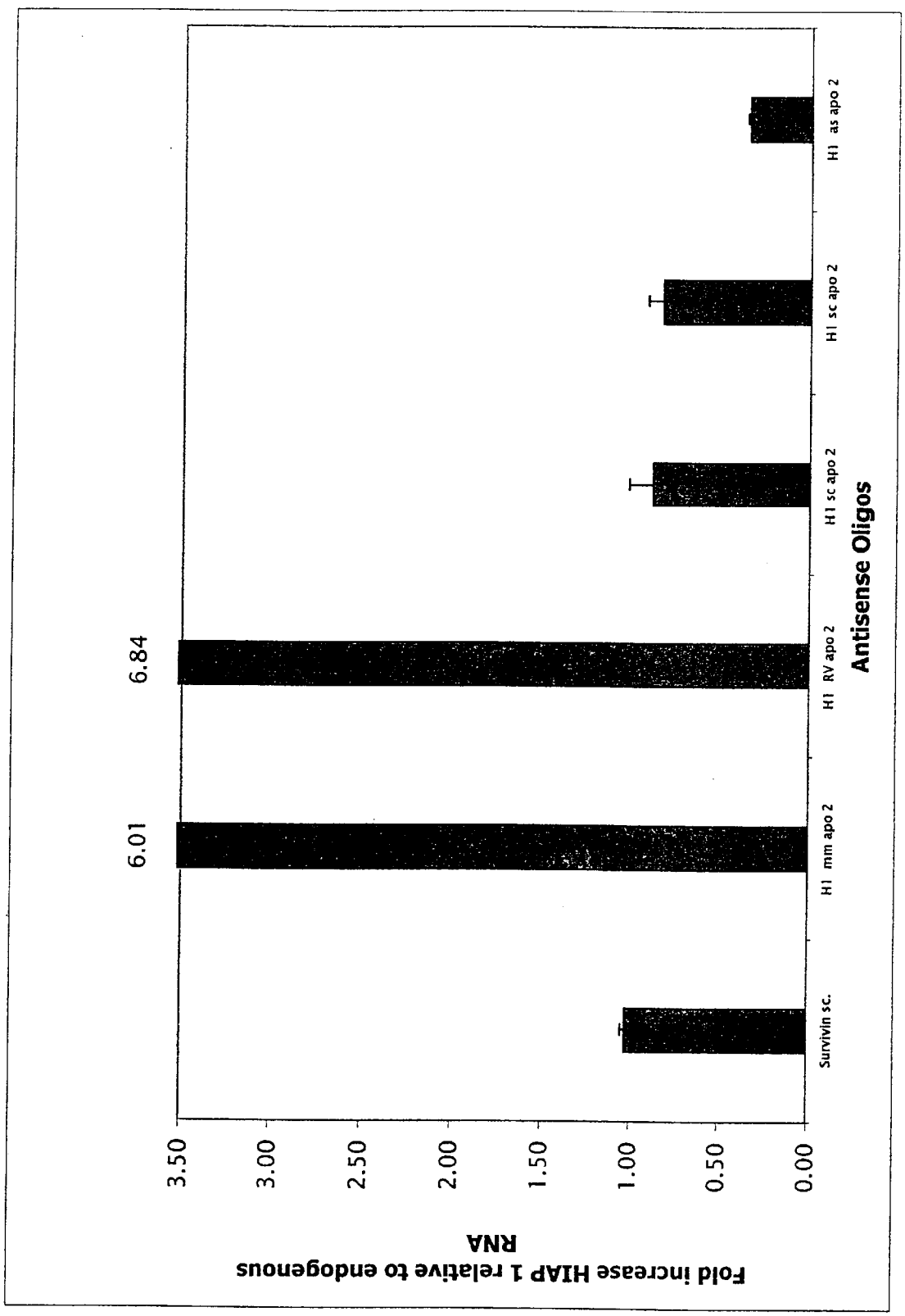
FIG. 13 is a graph showing the validation of the sequence specificity for HIAP1 antisense oligonucleotide APO 2.

Of the 15 tested ODNs, 6 of them (APO 1, −2, −7, −8, −12, and −15) showed the strongest activity, or had significant activity in both the protein and mRNA assays, and did not cause a stress-induced increase in HIAP1 mRNA, such as that seen with ODNs APO 4, −6, −11, −13, −14 (FIG. 10), and by control ODNs to APO 2 (mismatch or reverse polarity, see text below and FIGS. 12 and 13). Note that APO 6 also showed evidence of toxicity as seen by the general decrease in total protein (FIG. 12).

To further investigate the efficacy of HIAP1 antisense oligonucleotides under cycloheximide induction conditions, changes in HIAP1 mRNA were measured by TaqMan real time PCR 6 hours after transfection with ODN APO 2, which targets an Alu repeat within an intron of HIAP1 and results in the greatest block of CHX-induced upregulation of HIAP1 mRNA and protein. Controls for this experiment were three ODNs for APO 2: one scrambled sequence (same base composition but random order, AAG GGC GGC GGA GTG AGA C; SEQ ID NO: 213), one reverse polarity (same base composition, same sequential order but in the opposite direction, AGA GGA CGG AGT CGG AGG C; SEQ ID NO: 214), and one mismatch sequence (containing 4 base mismatches out of 19 bases, CGG AGC GTG AGG ATG GAG A; SEQ ID NO: 215).

Transfection of the APO 2 antisense into cells resulted in a 50% decrease in mRNA compared to a scrambled survivin control and matched perfectly with the protein results, while the scrambled control for APO 2 (H1 sc apo 2 in FIG. 13) did not change HIAP1 mRNA levels at all (repeated twice here, and in two different experiments). However, the mismatch control ODN (H1 mm apo 2) and the reverse polarity control ODN (H1 RV apo 2) showed an induction of 6 to 7 fold in HIAP1 mRNA at 6 hours. These ODNs no longer targeted HIAP1, as expected, but may still target Alu repeats because of the degeneracy and repeat nature of these sequences. Therefore, it is possible that these two controls are toxic to the cell and cause a stress response that leads to the induction of HIAP1. This effect may also occur with the antisense APO 2 ODN, but in this case, the APO 2 ODN also causes the degradation of the induced HIAP1 mRNA which results in a relative decrease of HIAP1 mRNA, compared to a scrambled survivin control, as well as decreasing the relative fold induction of HIAP1 protein after transfection and CHX treatment, compared to scrambled survivin control ODN.

The 6 optimal antisense HIAP1 ODNs include two very effective antisense ODNs against an intronic sequence (APO 1, and −2; with APO 2 demonstrating the best activity). These oligonucleotides have some interesting properties that could be of great use therapeutically for cancer or autoimmune disorders. The oligonucleotides against an intronic sequence would likely only target pre-mRNA (very short-lived target) and not the mature, processed form of HIAP1. Typically, introns are not targeted for antisense except when one wants to alter splicing by targeting the intron-exon boundaries or the branching point. These usually result in the skipping of an exon rather than RNase-mediated degradation of the message. Both mechanisms would likely be favorable for the enhancement of apoptosis, as the skipping would result in the loss of the exon encoding the first two important BIR domains of HIAP1. The APO-2 antisense oligo also targets an intron of survivin for 18 consecutive bases out of 19, but we did not see any loss of survivin protein; only HIAP1 was decreased after the oligo treatment, demonstrating the specificity of the HIAP1 antisense oligonucleotide. These antisense oligonucleotides hit Alu sequences in the HIAP1 intron and potentially in many other genes, and induce the cancer cells to die (see below), which may be as a result of down regulating HIAP1 and some other critical genes, and thus of therapeutic value if it is not too toxic to normal cells.

Cancer cells have reportedly more Alu-containing transcripts and may therefore be more sensitive to apoptosis induction with an Alu targeting antisense ODN. Furthermore, this killing effect of APO 1 and APO 2 ODNs may be due to the combined effect of both targeting Alu sequences and HIAP1 simultaneously. This dual effect would result in an effective way to prevent the normal stress response of HIAP1 induction through the NFkB pathway, when the cell is exposed to certain toxic agents. This stress response is most likely part of the cancer cell's anti-apoptotic program. By blocking HIAP1 expression, we counter this anti-apoptotic stress response and precipitate the cancer cell's demise.

EXAMPLE 8

HIAP1 Antisense Oligonucleotides Increase Cytotoxicity and Chemosensitization

The effect of HIAP1 antisense oligonucleotides on the chemosentization of SF295 cells was also evaluated. Cells were transfected with one of 3 different antisense ODNs (APO 7, APO 15, and Scrambled APO 2 (control)). Twenty-four hours after tranfection with the ODNs, the cells were incubated with adriamycin for an additional 24 hours before assaying by for cell survival by assaying WST-1.

Figure 14:
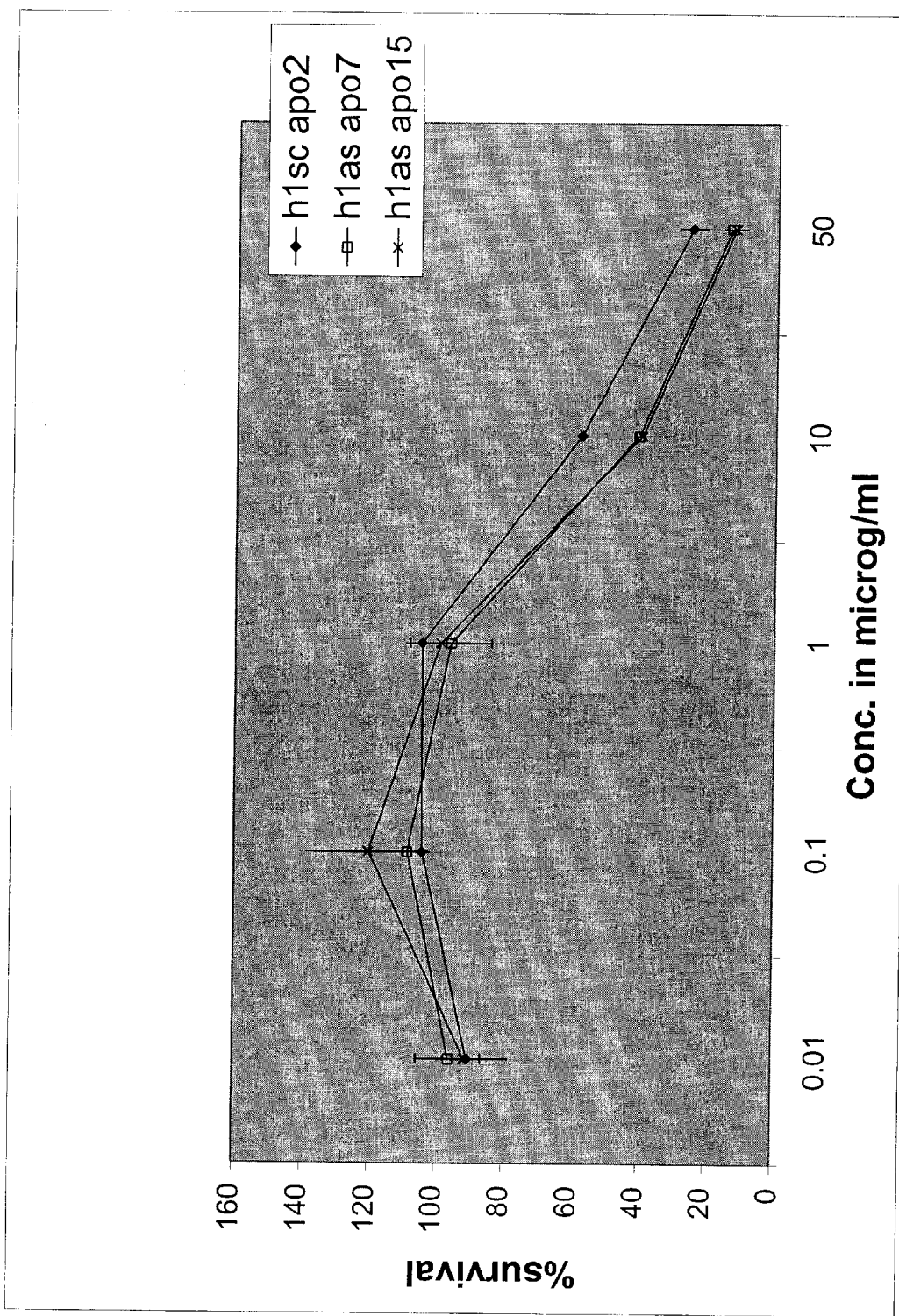
FIG. 14 is a graph showing the effect of HIAP1 antisense oligonucleotides on the chemosensitization of drug-resistant SF295 glioblastomas.

The WST-1 survival curves for SF295 cells transfected with the above-described HIAP1 ODNs and then treated with increasing concentrations of adriamycin are shown in FIG. 14. The two ODNs that resulted in a decrease in HIAP1 mRNA also showed a decrease in survival when treated with adriamycin compared to cells treated with an ODN which did not reduce HIAP1 mRNA levels. Therefore, reducing HIAP1 levels by antisense, or other means, can chemosensitize a glioblastoma cell line that is highly resistant to the cytotoxic action of many chemotherapeutic drugs.

EXAMPLE 9

In Vivo Analyses of IAP Antisense Oligonucleotides

Antisense oligonucleotides that decrease expression of IAP in cell culture models can be tested in animals. For example, the antisense oligonucleotide can be tested in mice according to the method of Lopes de Menezes et al. (Clin. Cancer Res. 6: 2891–2902, 2000) or Klasa et al. (Clin. Cancer Res. 6: 2492–2500, 2000). Antisense and control ODNs are tested, for example, in sub-cutaneous human xenografts of breast cancer, colon cancer, lung cancer, squamous cell carcinoma or prostate cancer in SCID mice. The antisense oligonucleotides are also tested in an orthotopic model for the prostate, as well as in a disseminated non-Hodgkin's lymphoma model. The mouse's tolerance to cisplatin, taxol, doxorubicin, and cyclophosphamide is known for each of these models.

In vivo testing of the antisense oligonucleotides involves 15 intraperitoneal injections (once a day, on days 3 through 7, 10 through 14, and 17 through 21) of naked ODN of (5 mg/kg), with or without a chemotherapeutic drug.

Alternatively, liposomal type carriers for the ODNs may also be employed. Oligos are injected shortly after tumors cells have been seeded in the mouse, or when the tumor has established and grown to a size of 0.1–0.15 g. Tumor size is then monitored to determine if the ODN treatments or ODN plus drug treatments reduce the growth rate of the tumor, lead to regression, or have no effect at all. In another alternative, ODNs in liposomal formulation are injected directly into the tumors.

EXAMPLE 10

Anti-IAP Antibodies

In order to generate IAP-specific antibodies, an IAP coding sequence (e.g., amino acids 180–276) can be expressed as a C-terminal fusion with glutathione S-transferase (GST; Smith et al., Gene 67:31–40, 1988). The fusion protein can be purified on glutathione-Sepharose beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titres are monitored by Western blot and immunoprecipitation analyses using the thrombin-cleaved IAP fragment of the GST-IAP fusion protein. Immune sera are affinity-purified using CNBr-Sepharose-coupled IAP protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of IAP may be generated and coupled to keyhole limpet hemocyanin (KLH) through an introduced C-terminal lysine. Antiserum to each of these peptides is similarly affinity-purified on peptides conjugated to BSA, and specificity is tested by ELISA and Western blotting, using peptide conjugates, and by Western blotting and immunoprecipitation using IAP expressed as a GST fusion protein.

Alternatively, monoclonal antibodies may be prepared using the IAP proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas*, Elsevier, New York, N.Y., 1981; Ausubel et al., *Current Protocols in Molecular Biology*, John Wiley & Sons, New York, N.Y., 1994). Once produced, monoclonal antibodies are also tested for specific IAP recognition by Western blot or immunoprecipitation analysis (by the methods described in Ausubel et al., supra).

Antibodies that specifically recognize IAPs or fragments of IAPs, such as those described in U.S. Ser. No. 08/800, 929, incorporated herein by reference, containing one or more BIR domains (but not a ring zinc finger domain), or that contain a ring zinc finger domain (but not a BIR domain) are considered useful in the invention. They may, for example, be used in an immunoassay to monitor IAP expression levels or to determine the subcellular location of an IAP or IAP fragment produced by a mammal. Antibodies that inhibit the 26 kDa IAP cleavage product described herein (which contains at least one BIR domain) may be especially useful in inducing apoptosis in cells undergoing undesirable proliferation.

Preferably antibodies of the invention are produced using IAP sequence that does not reside within highly conserved regions, and that appears likely to be antigenic, as analyzed by criteria such as those provided by the Peptide structure program (Genetics, Computer Group Sequence Analysis Package, Program Manual for the GCG Package, Version 7, 1991) using the algorithm of Jameson and Wolf (CABIOS 4:181, 1988). Specifically, these regions, which are found between BIR1 and BIR2 of all IAPs, are: from amino acid 99 to amino acid 170 of HIAP1, from amino acid 123 to amino acid 184 of HIAP2, and from amino acid 116 to amino acid 133 of either XIAP or m-XIAP. These fragments can be generated by standard techniques, e.g., by the PCR, and cloned into the pGEX expression vector (Ausubel et al., supra). Fusion proteins are expressed in *E. coli* and purified using a glutathione agarose affinity matrix as described in Ausubel et al. (supra). In order to minimize the potential for obtaining antisera that is non-specific, or exhibits low-affinity binding to IAP, two or three fusions are generated for each protein, and each fusion is injected into at least two rabbits. Antisera are raised by injections in series, preferably including at least three booster injections.

EXAMPLE 11

Comparison of Cell Survival Following Transfection With Full Length vs. Partial IAP Constructs In order to investigate the mechanism whereby human IAPs, including XIAP, HIAP1, and HIAP2, afford protection against cell death, expression vectors were constructed that contained either: (1) full-length IAP cDNA (as described in U.S. Ser. No. 08/800,929), (2) a portion of an IAP gene that encodes the BIR domains, but not the RZF, or (3) a portion of an IAP gene that encodes the RZF, but not the BIR domains. Human and murine XIAP cDNAs were tested by transient or stable expression in HeLa, Jurkat, and CHO cell lines. Following transfection, apoptosis was induced by serum withdrawal, application of menadione, or application of an anti-Fas antibody. Cell death was then assessed by trypan blue exclusion. As a control for transfection efficiency, the cells were co-transfected with a Beta-gal expression construct. Typically, approximately 20% of the cells were successfully transfected.

When CHO cells were transiently transfected, constructs containing full-length human or mouse XIAP cDNAs conferred modest but definite protection against cell death. In contrast, the survival of CHO cells transfected with constructs encoding only the BIR domains (i.e., lacking the RZF domain) was markedly enhanced 72 hours after serum deprivation. Furthermore, a large percentage of cells expressing the BIR domains were still viable after 96 hours, at which time no viable cells remained in the control, i.e. non-transfected, cell cultures, and less than 5% of the cells transfected with the vector only, i.e., lacking a cDNA insert, remained viable. Deletion of any of the BIR domains results in the complete loss of apoptotic suppression, which is reflected by a decrease in the percentage of surviving CHO cells to control levels within 72 hours of serum withdrawal.

Stable pools of transfected CHO cells, which were maintained for several months under G418 selection, were induced to undergo apoptosis by exposure to 10 $\mu$M menadione for 2 hours. Among the CHO cells tested were those that were stably transfected with: (1) full-length murine XIAP cDNA (miap), (2) full-length XIAP cDNA (XIAP), (3) full-length bcl-2 cDNA (Bcl-2), (4) cDNA encoding the three BIR domains (but not the RZF) of murine XIAP (BIR), and (5) cDNA encoding the RZF (but not BIR domains) of m-XIAP (RZF). Cells that were non-transfected (CHO) or transfected with the vector only (pcDNA3), served as controls for this experiment. Following exposure to 10 μM menadione, the transfected cells were washed with phosphate buffered saline (PBS) and cultured for an additional 24 hours in menadione-free medium. Cell death was assessed, as described above, by trypan blue exclusion. Less than 10% of the non-transfected or vector-only transfected cells remained viable at the end of the 24 hour survival period. Cells expressing the RZF did not fare significantly better. However, expression of full-length murine XIAP, human XIAP, or bcl-2, and expression of the BIR domains, enhanced cell survival. When the concentration of menadione was increased from 10 μM to 20 μM (with all other conditions of the experiment being the same as when 10 μM menadione was applied), the percentage of viable CHO cells that expressed the BIR domain cDNA construct was higher than the percentage of viable cells that expressed either full-length murine XIAP or bcl-2.

EXAMPLE 12

Analysis of the Subcellular Location of Expressed RZF and BIR Domains

The assays of cell death described above indicate that the RZF acts as a negative regulator of the anti-apoptotic function of IAPs. One way in which the RZF, and possibly other IAP domains, may exert their regulatory influence is by altering the expression of genes, whose products function in the apoptotic pathway.

In order to determine whether the subcellular locations of expressed RZF and BIR domains are consistent with roles as nuclear regulatory factors, COS cells were transiently transfected with the following four constructs, and the expressed polypeptide was localized by immunofluorescent microscopy: (1) pcDNA3–6myc-xiap, which encodes all 497 amino acids of SEQ ID NO: 219, (2) pcDNA3–6myc-m-xiap, which encodes all 497 amino acids of mouse XIAP (SEQ ID NO: 225), (3) pcDNA3–6myc-mxiap-BIR, which encodes amino acids 1 to 341 of m-xiap (SEQ ID NO: 225), and (4) pcDNA3–6myc-mxiap-RZF, which encodes amino acids 342–497 of murine xiap (SEQ ID NO: 225). The cells were grown on multi-well tissue culture slides for 12 hours, and then fixed and permeabilized with methanol. The constructs used (here and in the cell death assays) were tagged with a human Myc epitope tag at the N-terminus. Therefore, a monoclonal anti-Myc antibody and a secondary goat anti-mouse antibody, which was conjugated to FITC, could be used to localize the expressed products in transiently transfected COS cells. Full-length XIAP and MIAP were located in the cytoplasm, with accentuated expression in the peri-nuclear zone. The same pattern of localization was observed when the cells expressed a construct encoding the RZF domain (but not the BIR domains). However, cells expressing the BIR domains (without the RZF) exhibited, primarily, nuclear staining. The protein expressed by the BIR domain construct appeared to be in various stages of transfer to the nucleus.

Other Embodiments

All publications and patent applications mentioned in this specification, including U.S. Pat. No. 5,919,912 and U.S. Ser. Nos. 08/576,956 and 08/800,929 are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

What is claimed is:

1. A nucleic acid that inhibits XIAP biological activity, wherein said nucleic acid consists of DNA and/or RNA residues corresponding to any one of the sequences of SEQ ID NOS: 6, 16, 26, 27, 31, 41, 47, 51, 63, and 93.

2. The nucleic acid of claim 1, wherein said nucleic acid consists of DNA and/or RNA residues corresponding to the sequence of SEQ ID NO: 6.

3. The nucleic acid of claim 1, wherein said nucleic acid consists of DNA and/or RNA residues corresponding to the sequence of SEQ ID NO: 16.

4. The nucleic acid of claim 1, wherein said nucleic acid consists of DNA and/or RNA residues corresponding to the sequence of SEQ ID NO: 26.

5. The nucleic acid of claim 1, wherein said nucleic acid consists of DNA and/or RNA residues corresponding to the sequence of SEQ ID NO: 27.

6. The nucleic acid of claim 1, wherein said nucleic acid consists of DNA and/or RNA residues corresponding to the sequence of SEQ ID NO: 31.

7. The nucleic acid of claim 1, wherein said nucleic acid consists of DNA and/or RNA residues corresponding to the sequence of SEQ ID NO: 41.

8. The nucleic acid of claim 1, wherein said nucleic acid consists of DNA and/or RNA residues corresponding to the sequence of SEQ ID NO: 47.

9. The nucleic acid of claim 1, wherein said nucleic acid consists of DNA and/or RNA residues corresponding to the sequence of SEQ ID NO: 51.

10. The nucleic acid of claim 1, wherein said nucleic acid consists of DNA and/or RNA residues corresponding to the sequence of SEQ ID NO: 63.

11. The nucleic acid of claim 1, wherein said nucleic acid consists of DNA and/or RNA residues corresponding to the sequence of SEQ ID NO: 93.

12. The nucleic acid of claim 1, wherein said XIAP biological activity is inhibition of apoptosis.

13. The nucleic acid of claim 1, wherein said XIAP biological activity is inhibition of XIAP polypeptide expression.

14. The nucleic acid of claim 1, wherein said nucleic acid comprises at least one modified internucleoside linkage.

15. The nucleic acid of claim 14, wherein said modified internucleoside linkage is selected from the group consisting of phosphorothioate, methylphosphonate, phosphotriester, phosphorodithioate, and phosphoselenate linkages.

16. The nucleic acid of claim 1, wherein said nucleic acid comprises at least one modified sugar moiety.

17. The nucleic acid of claim 16, wherein said modified sugar moiety is a 2'-O methoxyethyl or a 2'-O methyl group.

18. The nucleic acid of claim 1, wherein said nucleic acid is a chimeric nucleic acid.

19. The nucleic acid of claim 18, wherein said chimeric nucleic acid comprises DNA residues linked together by phosphorothioate linkages, said DNA residues flanked on each side by at least one 2'-O methoxyethyl RNA residue or 2'-O methyl RNA residue linked together by phosphorothioate linkages.

20. The nucleic acid of claim 19, wherein said DNA residues are flanked on each side by at least three residues selected from the group consisting of 2'-O methoxyethyl RNA residues and 2'-O methyl RNA residues.

21. The nucleic acid of claim 1, wherein said nucleic acid is a ribozyme.

22. The nucleic acid of claim 1, wherein the three most 5' and the three most 3' nucleobases are RNA residues.

* * * * *

UNITED STATES PATENT AND TRADEMARK OFFICE
CERTIFICATE OF CORRECTION

PATENT NO. : 6,673,917 B1
DATED : January 6, 2004
INVENTOR(S) : Robert G. Korneluk et al.

Figure 11B:
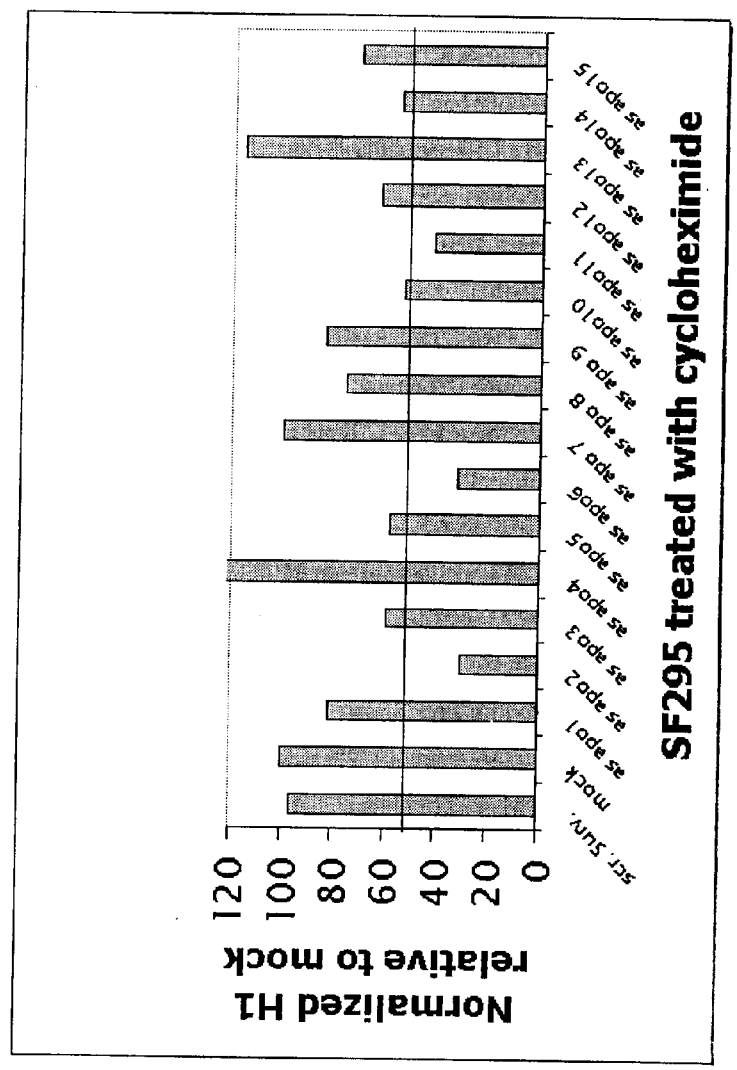
FIG. 11 is a graph showing the effects of HIAP1 antisense oligonucleotides on a cell's ability to block cycloheximide-induced upregulation of HIAP1 protein.

It is certified that error appears in the above-identified patent and that said Letters Patent is hereby corrected as shown below:

Column 11,
Line 16, "Fig. 11" should be -- Fig. 11B --.

Signed and Sealed this

Fourth Day of May, 2004

JON W. DUDAS
*Acting Director of the United States Patent and Trademark Office*